United States Patent
Thompson et al.

(10) Patent No.: US 7,560,586 B2
(45) Date of Patent: Jul. 14, 2009

(54) ACID AND ESTER COMPOUNDS AND METHODS OF USING THE SAME

(75) Inventors: Scott K. Thompson, King of Prussia, PA (US); Lara S. Kallander, King of Prussia, PA (US); Chun Ma, Edgewater, NJ (US); Joseph Marino, King of Prussia, PA (US); Dennis Lee, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 478 days.

(21) Appl. No.: 10/508,893

(22) PCT Filed: Mar. 26, 2003

(86) PCT No.: PCT/US03/09278

§ 371 (c)(1), (2), (4) Date: Jan. 26, 2005

(87) PCT Pub. No.: WO03/082802

PCT Pub. Date: Oct. 9, 2003

(65) Prior Publication Data

US 2006/0041164 A1 Feb. 23, 2006

Related U.S. Application Data

(60) Provisional application No. 60/368,426, filed on Mar. 27, 2002.

(51) Int. Cl.
C07C 229/00 (2006.01)
(52) U.S. Cl. ...................................... 560/42
(58) Field of Classification Search ................ 560/155, 560/42; 546/297
See application file for complete search history.

(56) References Cited

U.S. PATENT DOCUMENTS

| | | | |
|---|---|---|---|
| 2003/0153541 A1 | 8/2003 | Dudley et al. | 514/171 |
| 2003/0162758 A1 | 8/2003 | Schwartz et al. | 514/172 |
| 2003/0229062 A1 | 12/2003 | Schwartz et al. | 514/177 |
| 2004/0072868 A1* | 4/2004 | Collins et al. | 514/318 |
| 2004/0266663 A1 | 12/2004 | Schwartz et al. | 514/2 |
| 2005/0036992 A1 | 2/2005 | Saez et al. | 424/93.21 |
| 2005/0107444 A1 | 5/2005 | Thompsom et al. | 514/345 |
| 2005/0113580 A1 | 5/2005 | Thompson et al. | 546/268.1 |
| 2005/0131014 A1 | 6/2005 | Collini et al. | 514/311 |
| 2005/0171084 A1 | 8/2005 | Cairns et al. | 514/210.21 |
| 2005/0282750 A1 | 12/2005 | Schwartz et al. | 514/12 |
| 2005/0282908 A1 | 12/2005 | Collins et al. | 514/620 |

FOREIGN PATENT DOCUMENTS

| | | |
|---|---|---|
| EP | 0 394 440 | 10/1990 |
| GB | 1538775 | 1/1979 |
| WO | WO 02/24632 | 3/2002 |
| WO | WO 03/082192 | 10/2003 |
| WO | WO 03/082205 | 10/2003 |
| WO | WO 2004/043939 | 5/2004 |
| WO | WO 2004/058819 A2 | 7/2004 |
| WO | WO 2004/110368 A2 | 12/2004 |
| WO | WO 2004/110375 A2 | 12/2004 |
| WO | WO 2005/009383 A2 | 2/2005 |
| WO | WO 2005/013946 A2 | 2/2005 |
| WO | WO 2005/055998 A1 | 6/2005 |
| WO | WO 2006/000576 A2 | 1/2006 |
| WO | WO 2006/000577 A2 | 1/2006 |
| WO | WO 2006/004030 A1 | 1/2006 |

OTHER PUBLICATIONS

Grefhorst et al. *Am. J. Physiol. Endocrinol. Metab.*, 289: E829-E838 (2005).
Groot et al. *J. Lipid Res.*, 46: 2182-2191 (2005).
Jaye et al. *J. Med. Chem.*, 48: 5419-5422 (2005).
Ogawa et al. *Circ. Res.*, 96: e59-e67 (2005).
Quinet et al. *J. Lipid Res.*, 45: 1929-1942 (2004).
Miao et al. *J. Lipid Res.*, 45: 1410-1417 (2004).
Schmuth et al. *J. Invest. Dermatol.* 123: 41-48 (2004).
Farnegardh et al. *J. Biol. Chem.*, 278(40): 38821-38828 (2003).
Wang et al. *J. Molec. Graphics and Modelling*, 22: 173-181 (2003).
Fowler et al. *J. Invest. Dermatol.*, 120: 246-255 (2003).
Joseph et al. *PNAS USA*, 99(11): 7604-7609 (2002).
Fluhr et al. *J. Invest. Dermatol.*, 125: 1206-1214 (2005).
Naik et al. *Circulation*, 113: 90-97 (2006).
Kruit et al. *Gastroenterology*, 128: 147-156 (2005).
Laffitte et al. *PNAS USA*, 100(9): 5419-5424 (2003).
Castrillo et al. *J. Biol. Chem.*, 278(12): 10443-10449 (2003).

(Continued)

*Primary Examiner*—Taylor Victor Oh
(74) *Attorney, Agent, or Firm*—Kathryn L. Sieburth; Charles M. Kinzig

(57) ABSTRACT

Disclosed is a compound of having the formula:

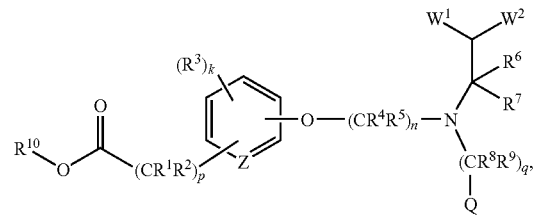

pharmaceutically acceptable salts or solvates thereof and pharmaceutical compositions containing the same, wherein the structural variables are as defined herein. The compounds, salts and solvates of this invention are useful as LXR agonists.

27 Claims, No Drawings

OTHER PUBLICATIONS

Laffitte et al. *Mol & Cell. Biol.*, 23(6): 2182-2191 (2003).
Collins et al. *J. Med. Chem.*, 45: 1963-1966 (2002).
Terasaka et al. *FEBS Journal*, 272: 1546-1556 (2005).
Collins et al. *Abstracts of Papers, 230th ACS National Meeting, Washington, DC*. Aug. 28-Sep. 1, 2005. MEDI-237. Publisher: American Chemical Society, Washington, DC.
Rao et al. *Abstracts of Papers, 229th ACS National Meeting, San Diego, CA*. Mar. 13-17, 2005. COMP-258. Publisher: American Chemical Society, Washington, DC.
Jon L. Collins. *Abstracts of Papers, 225th ACS National Meeting, New Orleans, LA*. Mar. 23-27, 2003. MEDI-152. Publisher: American Chemical Society, Washington, DC.
Collins et al. *Abstracts of Papers, 223rd ACS National Meeting, Orlando, FL*. Apr. 7-11, 2002. MEDI-123. Publisher: American Chemical Society, Washington, DC.
Angelo Gavezzotti. Acc. Chem. Res., 27: 309-314 (1994).
Vippagunta et al. Advanced Drug Delivery Reviews, 48: 3-26 (2001).
Office Action: U.S. Appl. No. 10/508,849, filed Feb.5, 2007.
U.S. Appl. No. 60/499,659, filed Sep. 3, 2003, Hoang et al.
U.S. Appl. No. 60/500,295, filed Sep. 4, 2003, Hoang et al.
U.S. Appl. No. 60/499,779, filed Sep. 3, 2003, Kallander et al.
U.S. Appl. No. 60/500,296, filed Sep. 4, 2003, Kallander et al.
U.S. Appl. No. 60/499,762, filed Sep. 3, 2003, Hoang et al.

* cited by examiner

ACID AND ESTER COMPOUNDS AND METHODS OF USING THE SAME

This application is a 371 of International Application No. PCT/US03/09278, filed 26 Mar. 2003, which claims the benefit of U.S. Provisional Application No. 60/368,426, filed 27 Mar. 2002.

FIELD OF THE INVENTION

The present invention relates to compounds useful as modulating agents for liver X receptors (LXR). Additionally, the present invention relates to pharmaceutical formulations comprising such compounds, and the therapeutic use of the same.

BACKGROUND OF THE INVENTION

LXR is a transcription factor. The orphan nuclear receptors, LXRα and LXRβ (collectively LXR) play a role in the maintenance of cholesterol balance. Peet et al., *Curr. Opin. Genet. Dev.* 8:571-575 (1998). In addition, LXR binds to the ATP Binding Cassette Transporter-1 (ABCA1) gene and increases expression of the gene to result in increased ABCA1 protein. ABCA1 is a membrane bound transport protein which is involved in the regulation of cholesterol efflux from extrahepatic cells onto nascent HDL particles. Mutations in the ABCA1 gene are responsible for genetic diseases that result in the complete absence or low levels of HDL cholesterol and a concomitant highly increased risk of cardiovascular disease. See Brooks-Wilson et al., *Nat. Genet.* 22:336-345 (1999); Bodzioch et al., *Nat. Genet.* 22: 347-351 (1999); and Rust et al., *Nat. Genet.* 22:352-355 (1999). ABCA1 knockout mice homozygous for the mutation in the ABCA1 gene have virtually no plasma HDL, whereas the heterozygotes produce 50% of the HDL of wild type animals. See, Orso et al., *Nat. Genet.* 24:192-196 (2000) and McNeish et al., *Proc. Natl. Acad. Sci. USA* 97:4245-4250 (2000). ABCA1 knockout mice also show increased cholesterol absorption. See, McNeish et al., *Proc. Natl. Acad. Sci. USA* 97:4245-4250 (2000). Increased expression of ABCA1 results in increased HDL cholesterol, decreased absorption of cholesterol, and increased removal of excess cholesterol from extrahepatic tissues, including macrophages. LXR agonists also upregulate macrophage expression of apolipoprotein E and ABCG1, both of which contribute to the efflux of cellular cholesterol. By stimulating macrophage cholesterol efflux through upregulation of ABCA1, ABCG1, and apoE expression, as well as increasing the expression of other target genes including cholesteryl ester transfer protein and lipoprotein lipase, LXR agonists influence plasma lipoproteins.

Accordingly, compounds which function as LXR modulating agents, and particularly as LXR agonists, would be useful in methods of increasing ABCA1, ABCG1, and apolipoprotein E expression, increasing cholesterol efflux from peripheral cells, and treating LXR mediated diseases and conditions such as cardiovascular disease and inflammation.

SUMMARY OF THE INVENTION

This invention is directed to a compound of Formula I:

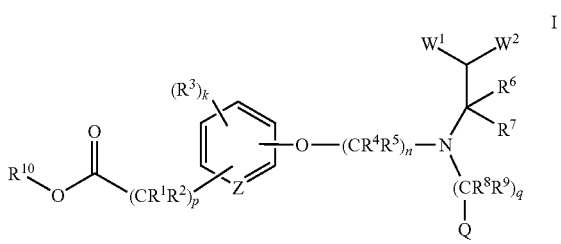

wherein:

Z is CH, $CR^3$ or N; wherein when Z is CH or $CR^3$, k is 0-4 and when Z is N, k is 0-3;

p is 0-8;

n is 2-8;

q is 0 or 1;

Q is selected from $C_3$-$C_8$ cycloalkyl, phenyl, and monocyclic Het; wherein said $C_3$-$C_8$ cycloalkyl, phenyl and monocyclic Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, $C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-OC(O)$NR^{12}R^{13}$, —$C_0$-$C_6$ alkyl-OC(O)$OR^{14}$, —$C_0$-$C_6$ alkyl-$NR^{12}$C(O)$OR^{14}$, —$C_0$-$C_6$ alkyl-$NR^{12}$C(O)$NR^{12}R^{13}$, and —$C_0$-$C_6$ alkyl-$NR^{12}COR^{14}$, where said $C_1$-$C_6$ alkyl is optionally unsubstituted or substituted by one or more halo substituents;

$W^1$ and $W^2$ are each independently $C_3$-$C_8$ cycloalkyl or aryl;

each $R^1$ and $R^2$ is independently selected from H, $C_1$-$C_6$ alkyl, —OH, —O—$C_1$-$C_6$ alkyl, —SH, and —S—$C_1$-$C_6$ alkyl;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, —$C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-OC(O)$NR^{12}R^{13}$, —$C_0$-$C_6$ alkyl-OC(O)$OR^{14}$, —$C_0$-$C_6$ alkyl-$NR^{12}$C(O)$OR^{14}$, —$C_0$-$C_6$ alkyl-$NR^{12}$C(O)$NR^{12}R^{13}$, and —$C_0$-$C_6$alkyl-$NR^{12}COR^{14}$, wherein said $C_1$-$C_6$ alkyl is optionally unsubstituted or substituted by one or more halo substituents;

each $R^4$ and $R^5$ is independently H or $C_1$-$C_4$ alkyl;

$R^6$ and $R^7$ are each independently H or $C_1$-$C_4$ alkyl;

$R^8$ and $R^9$ are each independently H or $C_1$-$C_4$ alkyl;

$R^{10}$ is selected from H, $C_1$-$C_8$ alkyl, $C_3$-$C_8$ alkenyl, $C_3$-$C_8$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{11}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{12}$ and each $R^{13}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{14}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

provided that $R^{10}$ is not H or methyl when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;

or a pharmaceutically acceptable salt or solvate thereof.

This invention is also directed to methods for the prevention or treatment of an LXR mediated disease or condition comprising administering a therapeutically effective amount of a compound having Formula I-A:

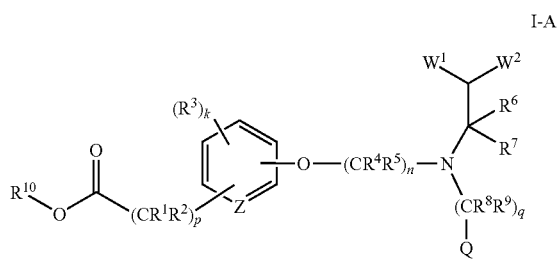

I-A wherein:

Z is CH, $CR^3$ or N; wherein when Z is CH or $CR^3$, k is 0-4 and when Z is N, k is 0-3;

p is 0-8;

n is 2-8;

q is 0 or 1;

Q is selected from $C_3$-$C_8$ cycloalkyl, phenyl, and monocyclic Het; wherein said $C_3$-$C_8$ cycloalkyl, phenyl and monocyclic Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, —$C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-$OC(O)NR^{12}R^{13}$, —$C_0$-$C_6$ alkyl-$OC(O)OR^{14}$, —$C_0$-$C_6$ alkyl-$NR^{12}C(O)OR^{14}$, —$C_0$-$C_6$ alkyl-$NR^{12}C(O)NR^{12}R^{13}$, and —$C_0$-$C_6$ alkyl-$NR^{12}COR^{14}$, where said $C_1$-$C_6$ alkyl is optionally unsubstituted or substituted by one or more halo substituents;

$W^1$ and $W^2$ are each independently $C_3$-$C_8$ cycloalkyl or aryl;

each $R^1$ and $R^2$ is independently selected from H, $C_1$-$C_6$ alkyl, —OH, —O—$C_1$-$C_6$ alkyl, —SH, and —S—$C_1$-$C_6$ alkyl;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, —$C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-$OC(O)NR^{12}R^{13}$, —$C_0$-$C_6$ alkyl-$OC(O)OR^{14}$, —$C_0$-$C_6$ alkyl-$NR^{12}C(O)OR^{14}$, —$C_0$-$C_6$ alkyl-$NR^{12}C(O)NR^{12}R^{13}$, and —$C_0$-$C_6$ alkyl-$NR^{12}COR^{14}$, wherein said $C_1$-$C_6$ alkyl is optionally unsubstituted or substituted by one or more halo substituents;

each $R^4$ and $R^5$ is independently H or $C_1$-$C_4$ alkyl;

$R^6$ and $R^7$ are each independently H or $C_1$-$C_4$ alkyl;

$R^8$ and $R^9$ are each independently H or $C_1$-$C_4$ alkyl;

$R^{10}$ is selected from H, $C_1$-$C_8$ alkyl, $C_3$-$C_8$ alkenyl, $C_3$-$C_8$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{11}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{12}$ and each $R^{13}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{13}$ and $R^{14}$ together with the nitrogen to which they are attached form a 4-7 membered heterocyclic ring which optionally contains one or more additional heteroatoms selected from N, O, and S; and $R^{14}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

provided that $R^{10}$ is not H when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;

or a pharmaceutically acceptable salt or solvate thereof.

Also included within the scope of this invention are methods for preparing compounds of this invention, or pharmaceutically acceptable salts or solvates thereof.

Unless otherwise provided, each alkyl, alkoxy, alkenyl, alkynyl, cycloalkyl, aryl or Het (including any 3-5-membered, 4-7-membered, 5-6-membered or 5-7-membered carbocyclic or heterocyclic rings or ring moieties) herein is independently unsubstituted or substituted with one ore more substituents defined hereinbelow.

LXR mediated diseases or conditions include inflammation, cardiovascular disease and atherosclerosis. Accordingly, the methods of this invention further comprise methods for increasing reverse cholesterol transport, inhibiting cholesterol absorption, and decreasing inflammation. The present invention also provides pharmaceutical compositions comprising a compound of this invention, or a pharmaceutically acceptable salt or solvate thereof.

DETAILED DESCRIPTION OF THE INVENTION

As used herein, the term "alkyl" represents a straight-or branched-chain saturated hydrocarbon, containing 1 to 10 carbon atoms, unless otherwise provided, which may be unsubstituted or substituted by one or more of the substituents described below. Exemplary alkyls include, but are not limited to methyl (Me), ethyl (Et), n-propyl, isopropyl, n-butyl, isobutyl, t-butyl, n-pentyl, neopentyl and hexyl and structural isomers thereof. Any "alkyl" herein may be optionally substituted by one or more of the substituents independently selected from the group halo, —OH, —SH, —$NH_2$, —NH (unsubstituted $C_1$-$C_6$ alkyl), —N(unsubstituted $C_1$-$C_6$ alkyl) (unsubstituted $C_1$-$C_6$ alkyl), unsubstituted —$OC_1$-$C_6$ alkyl, and —$CO_2H$.

When combined with another substituent term (e.g., aryl or cycloalkyl as in -alkyl-Ar or -alkyl-cycloalkyl), the "alkyl" term therein refers to an alkylene moiety, that is, an unsubstituted divalent straight-or branched-chain saturated hydrocarbon moiety, containing 1 to 10 carbon atoms, unless otherwise provided. For example, the term "—$C_0$-$C_6$ alkyl-Ar", where C is 1-6 is intended to mean the radical -alkyl-aryl (e.g., —$CH_2$-aryl or —$CH(CH_3)$-aryl) and is represented by the bonding arrangement present in a benzyl group. The term "$C_0$ alkyl" in a moiety, such as —$C_0$-$C_6$ alkyl-Ar or —O—($C_0$-$C_6$ alkyl)-Ar, provides for no alkyl/alkylene group being present in the moiety. Thus, when C is zero, —$C_0$-$C_6$ alkyl-Ar is equivalent to —Ar and —O—($C_0$-$C_6$ alkyl)-Ar is equivalent to —O—Ar.

As used herein, the term "alkenyl" represents a straight-or branched-chain hydrocarbon, containing 2 to 10 carbon atoms, unless otherwise provided, and one or more carbon-carbon double bonds. Alkenyl groups may be unsubstituted or substituted by one or more of the substituents described below. Exemplary alkenyls include, but are not limited ethenyl, 1-propenyl, 2-propenyl, 1-butenyl, 2-butenyl, isobutenyl, butadienyl, pentenyl and hexenyl and structural isomers thereof. Both cis (Z) and trans (E) isomers of each double bond that may be present in the compounds of this invention are included within the scope of this invention. Any "alkenyl" herein may be optionally substituted by one or more of the substituents independently selected from the group halo, —OH, —SH, —$NH_2$; —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, and —$CO_2H$.

As used herein, the term "alkynyl" represents a straight-or branched-chain hydrocarbon, containing 2 to 10 carbon atoms, unless otherwise provided, and one or more carbon-carbon triple bonds and, optionally, one or more carbon-carbon double bonds. Both cis (Z) and trans (E) isomers of each double bond that may be present in the compounds of this invention are included within the scope of this invention. Exemplary alkynyls include, but are not limited ethynyl, propynyl (propargyl, isopropynyl), 1-butynyl, 2-butynyl-3-butynyl, pentynyl and hexynyl and structural isomers thereof. Any "alkynyl" herein may be optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, and —$CO_2H$.

For the purposes of this invention, when an alkenyl or alkynyl group is a substituent on an oxygen, nitrogen or sulfur atom (e.g., as in oxy (—OR), thio (—SR), ester (—$CO_2R$ or —C(O)SR), amino (—NRR) or amido (—CONRR) moieties and the like), it is understood that a double or triple bond of the alkenyl or alkynyl group is not located on carbons that are α,β to the oxygen, nitrogen or sulfur atom. Compounds containing ene-amino or enol-type moieties (—NR—CR=CR— or —O—CR=CR—) are not intended to be included within the scope of this invention.

"Cycloalkyl" represents a non-aromatic monocyclic, bicyclic, or tricyclic hydrocarbon containing from 3 to 10 carbon atoms which may be unsubstituted or substituted by one or more of the substituents described below and may be saturated or partially unsaturated. Exemplary cycloalkyls include monocyclic rings having from 3-7, preferably 3-6, carbon atoms, such as cyclopropyl, cyclobutyl, cyclopentyl, cyclopentenyl, cyclopentadienyl, cyclohexyl, cyclohexenyl and cycloheptyl. Any "cycloalkyl" herein may be optionally substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC$, —$C_6$ alkenyl, —$C_0$-$C_6$ alkyl-COR', —$C_0$-$C_6$ alkyl-$CO_2R'$, —$C_0$-$C_6$ alkyl-CONR'R", —$OC_0$-$C_6$ alkyl-$CO_2H$, —$OC_2$-$C_6$ alkyl-NR'R", and —$C_0$-$C_6$ alkyl-$SO_2$NR'R", wherein each R' and R" are independently selected from H and unsubstituted $C_1$-$C_6$ alkyl.

The terms "Ar" or "aryl" as used herein interchangeably at all occurrences mean a substituted or unsubstituted carbocyclic aromatic group, which may be optionally fused to another carbocyclic aromatic group moiety or to a cycloalkyl group moiety, which may be optionally substituted or unsubstituted. Examples of suitable Ar or aryl groups include phenyl, naphthyl indenyl, 1-oxo-1H-indenyl and tetrahydronaphthyl. Any "Ar", "aryl" or "phenyl" herein may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, —$OC_1$-$C_6$ alkyl, —$OC_1$-$C_6$ alkenyl, —$C_0$-$C_6$ alkyl-COR', —$C_0$-$C_6$ alkyl-$CO_2R'$, —$C_0$-$C_6$ alkyl-CONR'R", —$OC_0$-$C_6$ alkyl-$CO_2H$, —$OC_2$-$C_6$ alkyl-NR'R", —$C_0$-$C_6$ alkyl-C(=NR')NR'R", and —$C_0$-$C_6$ alkyl-$SO_2$NR'R", wherein each R' and R" are independently selected from H and unsubstituted $C_1$-$C_6$ alkyl.

The term "Het" as used herein means a stable 5- to 7-membered monocyclic, a stable 7- to 10-membered bicyclic, or a stable 11- to 18-membered tricyclic heterocyclic ring group, all of which are saturated, unsaturated or aromatic, and consist of carbon atoms and from one to three heteroatoms selected from N, O and S, and which includes bicyclic and tricyclic rings containing one or more fused cycloalkyl, aryl (e.g., phenyl) or heteroaryl (aromatic Het) ring moieties. As used herein the term "Het" is also intended to encompass heterocyclic groups containing nitrogen and/or sulfur where the nitrogen or sulfur heteroatoms are optionally oxidized or the nitrogen heteroatom is optionally quaternized. The heterocyclic group may be attached at any heteroatom or carbon atom that results in the creation of a stable structure. Any "Het" herein may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$ alkyl, —$OC_1$-$C_6$ alkenyl, —$C_0$-$C_6$ alkyl-COR', —$C_0$-$C_6$ alkyl-$CO_2R'$, —$C_0$-$C_6$ alkyl-CONR'R", —$OC_0$-$C_6$ alkyl-$CO_2H$, —$OC_2$-$C_6$ alkyl-NR'R", —$C_0$-$C_6$ alkyl-C(=NR')NR'R" and —$C_0$-$C_6$ alkyl-$SO_2$NR'R", wherein each R' and R" are independently selected from H and unsubstituted $C_1$-$C_6$ alkyl.

Examples of such heterocyclic groups include, but are not limited to piperidinyl, piperazinyl, 2-oxopiperazinyl, 2-oxopiperidinyl, 2-oxopyrrolodinyl, 2-oxoazepinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, 1,3-benzodioxolyl (e.g., methylenedioxy-substituted phenyl), 1,4-benzodioxolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, benzofuranyl, benzothienyl, dihydrobenzofuranyl, dihydrobenzothienyl, dihydroindolyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable.

Examples of the 4-7 membered heterocyclic rings (which include 5-7 membered heterocyclic groups) useful in the compounds of this invention, include, but are not limited to azetidinyl, piperidinyl, piperazinyl, 2-oxopiperazinyl, 2-oxopiperidinyl, 2-oxopyrrolodinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 4-7 membered heterocyclic group may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$—$C_6$ alkyl, —$OC_1$-$C_6$ alkenyl, —$C_0$-$C_6$ alkyl-COR', —$C_0$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", —$C_0$-$C_6$ alkyl-C(=NR')NR'R" and —$C_0$-$C_6$ alkyl-$SO_2$NR'R", wherein each R' and R" are independently selected from H and unsubstituted $C_1$-$C_6$ alkyl.

The terms "halogen" and "halo" represent chloro, fluoro, bromo or iodo substituents. "Alkoxy" is intended to mean the radical —$OR_a$, where $R_a$ is an alkyl group, wherein alkyl is as defined above, provided that —O—$C_1$ alkyl may be optionally substituted by one or more of the substituents independently selected from the group halo and —$CO_2$H. Exemplary alkoxy groups include methoxy, ethoxy, propoxy, and the like. "Phenoxy" is intended to mean the radical —$OR_{ar}$, where $R_{ar}$ is a phenyl group. "Acetoxy" is intended to mean the radical —O—C(=O)-methyl. "Benzoyloxy" is intended to mean the radical —O—C(=O)-phenyl. "Oxo" is intended to mean the keto diradical =O, such as present on a pyrrolidin-2-one ring.

If a substituent described herein is not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful as an intermediate compound in the methods of this invention or is a desired substituent in a target compound.

The term "pharmaceutically acceptable salt" is intended to describe a salt that retains the biological effectiveness of the free acid or base of a specified compound and is not biologically or otherwise undesirable.

If an inventive compound is a base, a desired salt may be prepared by any suitable method known in the art, including treatment of the free base with an inorganic acid, such as hydrochloric acid, hydrobromic acid, sulfuric acid, sulfamic acid, nitric acid, phosphoric acid, metaphosphoric acid and the like, or with an organic acid, such as acetic acid, trifluoroacetic acid, formic acid, maleic acid, lactic acid, succinic acid, mandelic acid, fumaric acid, malonic acid, malic acid, pyruvic acid, oxalic acid, glycolic acid, citric acid, tartaric acid, gluconic acid, glutaric acid, lactobionic, orotic, cholic, a pyranosidyl acid, such as glucuronic acid or galacturonic acid, an amino acid, such as aspartic acid or glutamic acid, an aromatic acid, such as benzoic acid, salicylic acid, cinnamic acid, pamoic acid or 1-hydroxy-2-naphthoic acid, a sulfonic acid, such as benzenesulfonic acid, p-toluenesulfonic acid, naphthalenesulfonic acid, methanesulfonic acid, ethanesulfonic acid or the like. Additional examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates. Embodiments of a pharmaceutically acceptable salt (e.g., the hydrochloride salt) of the compounds of this invention are provided in the Examples.

If an inventive compound is an acid, a desired salt may be prepared by any suitable method known to the art, including treatment of the free acid with an excess of an inorganic or organic alkaline reagent. Illustrative examples of suitable salts include salts derived from ammonia; primary, secondary, tertiary amines (including secondary and tertiary cyclic amines), such as ethylene diamine, dicyclohexylamine, ethanolamine, piperidine, morpholine, and piperazine; salts derived from amino acids such as glycine and arginine; as well as salts derived from an alkali metal, alkaline earth metal, or ammonium hydroxide, carbonate, alkoxide or sulfate, such as sodium hydroxide, sodium carbonate, sodium bicarbonate, sodium sulfate, etc., and corresponding alkaline salts containing, for example, $Li^+$, $K^+$, $Ca^{++}$, $Mg^{++}$ and $NH_4^+$ cations.

The term "solvate" is intended to mean a pharmaceutically acceptable solvate form of a specified compound of this invention, or a salt thereof, that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, or solvates may exist in different crystal forms, all of which are intended to be within the scope of the present invention and specified formulas.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a mesylate salt or a sodium salt.

Also included within the scope of this invention are prodrugs of the compounds of this invention. The ester compounds of this invention, wherein X is other than —OH, may be considered prodrugs. Such ester compounds may be converted to compounds that are active as LXR modulators and may be, themselves, active as LXR modulators. The term "prodrug" is intended to mean a compound that is converted under physiological conditions, e.g., by solvolysis or metabolically, to a compound according to this invention that is pharmaceutically active. A prodrug may be a derivative of one of the compounds of this invention that contains a carboxylic or phosphoric acid ester or amide moiety that may be cleaved under physiological conditions. A prodrug containing such a moiety may be prepared according to conventional procedures, for example, by treatment of a compound of this invention containing an amino, amido or hydroxyl moiety with a suitable derivatizing agent, for example, a carboxylic or phosphoric acid halide or acid anhydride, or by converting a carboxyl moiety of a compound of this invention to an ester or amide. Prodrugs of the compounds of this invention may be determined using techniques known in the art, for example, through metabolic studies. See, e.g., "Design of Prodrugs," (H. Bundgaard, Ed.) 1985, Elsevier Publishers B.V., Amsterdam, The Netherlands.

The compounds of this invention may contain at least one chiral center and may exist as single stereoisomers (e.g., single enantiomers), mixtures of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that are at least 90% enantiomerically pure. Where the stereochemistry of the chiral carbons present in the chemical structures illustrated herein is not specified, the chemical structure is intended to encompass compounds containing either stereoisomer of each chiral center present in the compound. Such compounds may be obtained synthetically, according to the procedures described herein using optically pure (enantiomerically pure) or substantially optically pure materials. Alternatively, these compounds may be obtained by resolution/separation of a mixture of stereoisomers, including racemic mixtures, using conventional procedures. Exemplary methods that may be useful for the resolution/separation of mixtures of stereoisomers include chromatography and crystallization/re-crystallization. Other useful methods may be found in "Enantiomers, Racemates, and Resolutions," J. Jacques et al., 1981, John Wiley and Sons, New York, N.Y., the disclosure of which is incorporated herein by reference.

In one embodiment of this invention, the group $R^{10}OC(=O)(CR^1R^2)_p$— is located on the

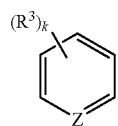

moiety in a position that is meta or para to the —$O(CR^4R^5)_n$— moiety. Preferably, the group $R^{10}OC(=O)(CR^1R^2)_p$— is located in a position that is meta to the —$O(CR^4R^5)_n$— moiety.

In another embodiment, this invention is directed to a compound of Formula II:

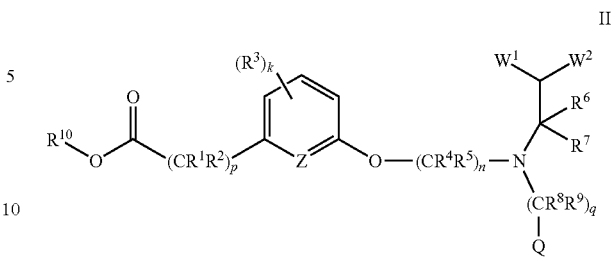

wherein:
Z is CH or N;
Q is phenyl or monocyclic Het; wherein said phenyl and monocyclic Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{11}$, —$C_0$-$C_4$ alkyl-$C(O)SR^{11}$, —$C_1$-$C_4$ alkyl-$CONR^{12}R^{13}$, —$C_0$-$C_4$ alkyl-$COR^{14}$, —$C_0$-$C_4$ alkyl-$NR^{12}R^{13}$, —$C_0$-$C_4$ alkyl-$SR^{11}$, —$C_0$-$C_4$ alkyl-$OR^{11}$, —$C_0$-$C_4$ alkyl-$SO_3H$, —$C_0$-$C_4$ alkyl-$SO_2NR^{12}R^{13}$, —$C_0$-$C_4$ alkyl-$R^{12}R^{13}$, —$C_0$-$C_4$ alkyl-$SOR^{14}$, —$C_0$-$C_4$ alkyl-$OCOR^{14}$, —$C_0$-$C_4$ alkyl-$OC(O)NR^{12}R^{13}$, —$C_0$-$C_4$ alkyl-$OC(O)OR^{14}$, —$C_0$-$C_4$ alkyl-$NR^{12}C(O)OR^{14}$, —$C_0$-$C_4$ alkyl-$NR^{12}C(O)NR^{12}R^{13}$, and —$C_0$-$C_4$ alkyl-$NR^{12}COR^{14}$, where said $C_1$-$C_6$ alkyl is optionally unsubstituted or substituted by one or more halo substituents,
p is 0-4;
k is 0, 1 or 2;
n is 2-4;
q is 0 or 1;
$W^1$ and $W^2$ are each independently $C_3$-$C_6$ cycloalkyl or aryl;
each $R^1$ and $R^2$ is independently selected from H, $C_1$-$C_4$ alkyl, —OH, —O—$C_1$-$C_4$ alkyl, —SH, and —S—$C_1$-$C_4$ alkyl;
each $R^3$ is the same or different and is independently selected from halo, cyano, $C_1$-$C_6$ alkyl, —$C_0$-$C_4$ alkyl-$NR^{12}R^{13}$, —$C_0$-$C_4$ alkyl-$OR^{11}$, —$C_0$-$C_4$ alkyl-$SO_2NR^{12}R^{13}$, and —$C_0$-$C_4$ alkyl-$CO_2H$, wherein said $C_1$-$C_6$ alkyl is optionally unsubstituted or substituted by one or more halo substituents;
each $R^4$ and $R^5$ is independently H or $C_1$-$C_4$ alkyl;
$R^6$ and $R^7$ are each independently H or $C_1$-$C_4$ alkyl;
$R^8$ and $R^9$ are each independently H or $C_1$-$C_4$ alkyl;
$R^{10}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_6$ cycloalkyl;
$R^{11}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;
each $R^{12}$ and each $R^{13}$ are independently selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{12}$ and $R^{13}$ together with the nitrogen to which they are attached form a 4-7 membered heterocyclic ring which optionally contains one or more additional heteroatoms selected from N, O, and S; and
$R^{14}$ is selected from $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;
provided that $R^{10}$ is not H or methyl when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;
or a pharmaceutically acceptable salt or solvate thereof.

In another embodiment, this invention is directed to methods for the prevention or treatment of an LXR mediated disease or condition comprising administering a therapeutically effective amount of a compound having Formula II-A:

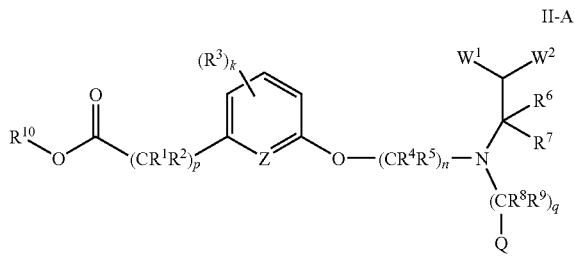

II-A wherein:

Z is CH or N;

Q is phenyl or monocyclic Het; wherein said phenyl and monocyclic Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{11}$, —$C_0$-$C_4$ alkyl-C(O)$SR^{11}$, —$C_0$-$C_4$ alkyl-$CONR^{12}R^{13}$, —$C_0$-$C_4$ alkyl-$COR^{14}$, —$C_0$-$C_4$ alkyl-$NR^{12}R^{13}$, —$C_0$-$C_4$ alkyl-$SR^{11}$, —$C_0$-$C_4$ alkyl-$OR^{11}$, —$C_0$-$C_4$ alkyl-$SO_3H$, —$C_0$-$C_4$ alkyl-$SO_2NR^{12}R^{13}$, —$C_0$-$C_4$ alkyl-$SR_2R^{11}$, —$C_0$-$C_4$ alkyl-$SOR^{14}$, —$C_0$-$C_4$ alkyl-$OCOR^{14}$, —$C_0$-$C_4$ alkyl-$OC(O)NR^{12}R^{13}$, —$C_0$-$C_4$ alkyl-$OC(O)OR^{14}$, —$C_0$-$C_4$ alkyl-$NR^{12}C(O)OR^{14}$, —$C_0$-$C_4$ alkyl-$NR^{12}C(O)NR^{12}R^{13}$, and —$C_0$-$C_4$ alkyl-$NR^{12}COR^{14}$, where said $C_1$-$C_6$ alkyl is optionally unsubstituted or substituted by one or more halo substituents, p is 0-4;

k is 0, 1 or 2;

n is 2-4;

q is 0 or 1;

$W^1$ and $W^2$ are each independently $C_3$-$C_6$ cycloalkyl or aryl;

each $R^1$ and $R^2$ is independently selected from H, $C_1$-$C_4$ alkyl, —OH, —O—$C_1$-$C_4$ alkyl, —SH, and —S—$C_1$-$C_4$ alkyl;

each $R^3$ is the same or different and is independently selected from halo, cyano, $C_1$-$C_6$ alkyl, —$C_0$-$C_4$ alkyl-$NR^{12}R^{13}$, —$C_0$-$C_4$ alkyl-$OR^{11}$, —$C_0$-$C_4$ alkyl-$SO_2NR^{12}R^{13}$, and —$C_0$-$C_4$ alkyl-$CO_2H$, wherein said $C_1$-$C_6$ alkyl is optionally unsubstituted or substituted by one or more halo substituents;

each $R^4$ and $R^5$ is independently H or $C_1$-$C_4$ alkyl;

$R^6$ and $R^7$ are each independently H or $C_1$-$C_4$ alkyl;

$R^8$ and $R^9$ are each independently H or $C_1$-$C_4$ alkyl;

$R^{10}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_6$ cycloalkyl;

$R^{11}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

each $R^{12}$ and each $R^{13}$ are independently selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{12}$ and $R^{13}$ together with the nitrogen to which they are attached form a 4-7 membered heterocyclic ring which optionally contains one or more additional heteroatoms selected from N, O, and S; and $R^{14}$ is selected from $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

provided that $R^{10}$ is not H when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;

or a pharmaceutically acceptable salt or solvate thereof.

Unless otherwise provided, each alkyl, alkoxy, alkenyl, alkynyl, cycloalkyl, aryl or Het herein is independently unsubstituted or substituted with one ore more substituents defined hereinabove.

In one embodiment of the compounds of this invention, $R^1$ and $R^2$ are each independently H or $C_1$-$C_6$ alkyl. Other embodiments comprise compounds wherein at least one of $R^1$ and $R^2$ is $C_1$-$C_4$ alkyl. In specific embodiments of the compounds of this invention, $R^1$ and $R^2$ are each H, or one of $R^1$ or $R^2$ is H and the other of $R^1$ or $R^2$ is $C_1$-$C_4$ alkyl, or both $R^1$ and $R^2$ are $C_1$-$C_3$ alkyl. In more specific embodiments of the compounds of this invention, $R^1$ and $R^2$ are each H, or one of $R^1$ or $R^2$ is H and the other of $R^1$ or $R^2$ is methyl, ethyl, propyl, butyl, or sec-butyl, or $R^1$ and $R^2$ are both methyl or ethyl.

The group

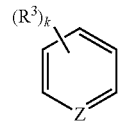

describes a 6-membered aromatic ring, specifically, a phenyl or pyridyl ring, which may be unsubstituted (k=0) or substituted by one or more substituents $R^3$. In a preferred embodiment, the compounds of this invention are defined where Z is CH. The total number of $R^3$ substituents that may be present in a compound of this invention is represented by "k". When Z is $CR^3$, k is 0-4, meaning that there can be up to four $R^3$ substituents on the 6-membered aromatic ring. When Z is CH or N, k is 0-3, meaning that there can be up to three $R^3$ substituents on the 6-membered aromatic ring. Preferably, k is 0 or 1.

In the embodiments wherein k is 1 or more, each $R^3$ may be the same or different. In specific embodiments of this invention, each $R^3$ is independently selected from halo, $C_1$-$C_4$ alkyl and $C_1$-$C_4$ alkoxy. By virtue of the definitions given above for the term "alkyl", this definition of $R^3$ also encompasses alkyl groups that are optionally substituted with the substituents specified in the definitions above. More specifically, each $R^3$ is independently selected from F, Cl, Br, methyl and methoxy. In specific embodiments, when k is 1, $R^3$ is halo or $C_1$-$C_4$ alkyl, specifically, Cl, Br or methyl.

In one embodiment, the compounds of this invention are defined wherein p is 0-3. In another embodiment, p is 0 or 1. In a specific embodiment, p is 0 or 1.

In another embodiment, the compounds of this invention are defined wherein n is 2-4. In specific embodiments, n is 3.

In another embodiment of the compounds this invention, $R^4$ and $R^5$ are independently selected from H and $C_1$-$C_3$ alkyl. By virtue of the definition given above for the term "alkyl", $R^4$ and $R^5$ also encompasses the alkyls optionally substituted with the substituents specified in the definition above. In specific embodiments of this invention, each $R^4$ and $R^5$ are H or one $R^4$ or $R^5$ is methyl.

In specific embodiments of the compounds this invention, q is 1 and $R^8$ and $R^9$ are both H.

In yet another embodiment of the compounds of this invention, $R^{10}$ is selected from H, $C_1$-$C_4$ alkyl, —$C_0$-$C_4$ alkyl-Ar, —$C_0$-$C_4$ alkyl-Het and —$C_0$-$C_4$ alkyl-$C_3$-$C_6$ cycloalkyl. In other embodiments of this invention, $R^{10}$ is H or $C_1$-$C_4$ alkyl. In specific embodiments, $R^{10}$ is H or methyl.

Group Q is selected from $C_3$-$C_7$ cycloalkyl, phenyl and monocyclic Het. By virtue of the definitions given above for the terms "cycloalkyl", "aryl" (which includes phenyl) and "Het" (which includes monocyclic Het), this definition of Q also encompasses cycloalkyl, phenyl and monocyclic Het groups that are optionally substituted from 1 to 4 times, more preferably, from 1 to 3 times with the substituents specified in the definitions above. In one embodiment, Q is a phenyl group. In one embodiment, Q is a substituted phenyl group containing one, two, or three substituents selected from halo, $C_1$-$C_4$ alkoxy and $C_1$-$C_4$ alkyl; specifically including $C_1$-$C_4$ haloalkyl, or Q is substituted pyridyl group containing one $C_1$-$C_4$ alkyl substituent. In another embodiment, Q is a substituted phenyl group containing one, two, or three substituents selected from —F, —Cl, —$CF_3$, —$OCH_3$, and —CH($CH_3$)$_2$, or Q is 6-methyl-pyridin-2-yl. In preferred embodiments, Q is a 2-chloro-3-(trifluoromethyl)phenyl group.

In another embodiment of this invention, $W^1$ and $W^2$ are the same or different and are either $C_3$-$C_8$ cycloalkyl or aryl. By virtue of the definitions given above for the terms "cycloalkyl" and "aryl" $W^1$ and $W^2$ also encompasses the foregoing rings optionally independently substituted with the substituents specified in the definitions above. In one embodiment of this invention, $W^1$ and $W^2$ are each aryl or one of $W^1$ or $W^2$ is aryl and the other of $W^1$ or $W^2$ is cyclopentyl. In another embodiment, $W^1$ and $W^2$ are each independently selected from unsubstituted phenyl and substituted phenyl comprising 1 to 3 substituents. In yet another embodiment, $W^1$ and $W^2$ are each independently selected from unsubstituted cyclopentyl, unsubstituted phenyl and mono-substituted phenyl, where the phenyl is substituted by halo. In specific, non-limiting embodiments, $W^1$ and $W^2$ are both unsubstituted phenyl, or one of $W^1$ or $W^2$ is unsubstituted phenyl and the other of $W^1$ or $W^2$ is cyclopentyl, or $W^1$ and $W^2$ are both fluoro-substituted phenyl or one of $W^1$ or $W^2$ is unsubstituted phenyl and the other of $W^1$ or $W^2$ is chloro-substituted phenyl.

When the moiety —O($CR^4R^5$)$_n$— is substituted and $R^4$ and $R^5$ are different on at least one ($CR^4R^5$) moiety (e.g., when one of $R^4$ or $R^5$ is methyl and the other of $R^4$ and $R^5$ is hydrogen) a chiral compound is obtained. Such chiral compounds preferably possess at least one $R^4$ or $R^5$ substituent having the following stereochemistry:

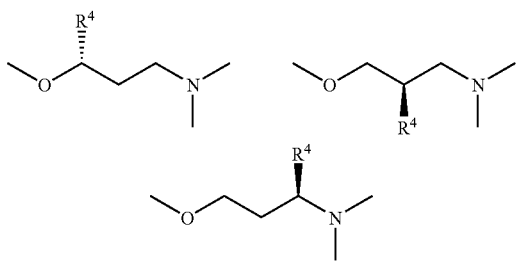

where the substituent $R^4$ is used merely to illustrate the stereochemical orientation of a non-hydrogen substituent (e.g., methyl).

In other embodiments of this invention, the —$C_0$-$C_6$ alkyl- and —$C_0$-$C_4$ alkyl-moieties of the substituents defined herein are unsubstituted —$C_0$-$C^6$ alkyl- and unsubstituted —$C_0$-$C_4$ alkyl-moieties, respectively.

It is to be understood that the present invention covers all combinations of particular and preferred groups described herein above.

Particular embodiments of this invention comprise compounds of this invention wherein $R^6$, $R^7$, $R^8$ and $R^9$ are each H; at least one $R^1$ or $R^2$ is $C_1$-$C_4$ alkyl and/or at least one $R^4$ or $R^5$ is $C_1$-$C_3$ alkyl and/or $W^1$ and $W^2$ are each independently selected from unsubstituted cyclopentyl, unsubstituted phenyl and mono-substituted phenyl, where the phenyl is substituted by halo; $R^{10}$ is H or $C_1$-$C_4$ alkyl; Q is a substituted phenyl group containing one, two, or three substituents selected from halo, $C_1$-$C_4$ alkoxy and $C_1$-$C_4$ alkyl; specifically including $C_1$-$C_4$ haloalkyl, or Q is substituted pyridyl group containing one $C_1$-$C_4$ alkyl substituent; Z is CH; p is 0, 1 or 2; n is 3; q is 1; and k is 0 or 1; $R^3$ is halo or $C_1$-$C_4$ alkyl; or a pharmaceutically acceptable salt or solvate thereof.

Other specific embodiments of this invention comprise compounds of this invention wherein $R^4$, $R^5$, $R^6$, $R^7$, $R^8$ and $R^9$ are each H; at least one of $R^1$ or $R^2$ is methyl, ethyl, propyl butyl or sec-butyl or both of $R^1$ and $R^2$ are methyl or ethyl; $R^{10}$ is H or methyl; Q is 2-chloro-3-(trifluoromethyl)phenyl; $W^1$ and $W^2$ are both unsubstituted phenyl, or one of $W^1$ or $W^2$ is unsubstituted phenyl and the other of $W^1$ or $W^2$ is cyclopentyl, or $W^1$ and $W^2$ are both fluoro-substituted phenyl or one of $W^1$ or $W^2$ is unsubstituted phenyl and the other of $W^1$ or $W^2$ is chloro-substituted phenyl; Z is CH; p is 0, 1 or 2; n is 3; q is 1; k is 0 or 1 and $R^3$ is Cl, Br or methyl; or a pharmaceutically acceptable salt or solvate thereof.

Specific embodiments of this invention comprise compounds of this invention wherein $R^6$, $R^7$, $R^8$ and $R^9$ are each H; $R^1$ and $R^2$ are each independently H or methyl; at least one $R^4$ or $R^5$ is methyl; $R^{10}$ is H or methyl; Q is a substituted phenyl group containing one, two, or three substituents selected from —F, —Cl, —$CF_3$, —$OCH_3$, and —CH($CH_3$)$_2$; $W^1$ and $W^2$ are unsubstituted phenyl; Z is CH; p is 1; n is 3; q is 1; and k is 0; or a pharmaceutically acceptable salt or solvate thereof.

A particular embodiment of this invention is directed to a compound of Formula I, II, I-A or II-A, as defined above, wherein at least one of $R^4$, $R^5$, $R^6$, $R^7$, $R^8$ or $R^9$ is defined as follows: wherein at least one $R^4$ or $R^5$ is $C_1$-$C_4$ alkyl; or at least one of $R^6$ of $R^7$ is $C_1$-$C_4$ alkyl; or both of $R^8$ or $R^9$ are independently $C_1$-$C_4$ alkyl. Other embodiments of this invention are directed to a compound of Formula I, II, I-A or II-A, as defined above, wherein at least one $R^4$ or $R^5$ is $C_1$-$C_4$ alkyl, specifically, wherein at least one $R^4$ or $R^5$ is methyl.

Another particular embodiment of this invention is directed to a compound of Formula I, I-A, II or II-A, as defined above, wherein any one of $R^4$ or $R^5$ is not H or any one of $R^6$ or $R^7$ is not H or $R^8$ and $R^9$ are each $C_1$-$C_4$ alkyl when Z is CH or $CR^3$ and k is 0-4 or Z is N and k is 0-3;

p is 0-8;

n is 2-8;

q is 0 or 1;

Q is selected from optionally unsubstituted or substituted $C_3$-$C_8$ cycloalkyl, phenyl and monocyclic Het;

$W^1$ and $W^2$ are each independently optionally unsubstituted or substituted $C_3$-$C_8$ cycloalkyl or aryl;

each $R^1$ and $R^2$ is independently selected from H, $C_1$-$C_6$ alkyl, —OH, —O—$C_1$-$C_6$ alkyl, —SH, and —S—$C_1$-$C_6$ alkyl;

each $R^3$ is the same or different and is independently selected from halo, cyano, nitro, —$CONR^{12}R^{13}$, —$COR^{14}$, —$SR^{11}$, —$SO_2R^{11}$, —$SOR^{14}$, —$OCOR^{14}$ and optionally unsubstituted or substituted $C_1$-$C_6$ alkyl, $C_3$-$C_6$ alkenyl, -5-6 membered-Het, —$C_0$-$C_6$ alkyl-$CO_2R^{11}$, or —$C_0$-$C_6$ alkyl-$NR^{12}R^{13}$, where the optionally unsubstituted or substituted $C_3$-$C_8$ cycloalkyl, phenyl and monocyclic Het; optionally unsubstituted or substituted $C_1$-$C_6$ alkyl, $C_3$-$C_6$ alkenyl, 5-6 membered-Het, —$C_0$-$C_6$ alkyl-$CO_2R^{11}$, or —$C_0$-$C_6$ alkyl-$NR^{12}R^{13}$, $R^{11}$, $R^{12}$ and $R^{13}$ and $R^{14}$ are as defined herein.

Compounds according to this invention include:
(R)-2-(3-{3-[[2-chloro-3-(trifluoromethyl)benzyl](2,2-diphenylethyl)amino]-2-methyl-propoxy}-phenyl)acetic acid methyl ester;
(R)-2-(3-{3-[[2-chloro-3-(trifluoromethyl)benzyl](2,2-diphenylethyl)amino]-2-methyl-propoxy}-phenyl)acetic acid;
(S)-2-(3-{3-[[2-chloro-3-(trifluoromethyl)benzyl](2,2-diphenylethyl)amino]-2-methyl-propoxy}-phenyl)acetic acid;
(R)-2-(3-{3-[[2-chloro-3-(trifluoromethyl)benzyl](2,2-diphenylethyl)amino]-1-methyl-propoxy}-phenyl)acetic acid methyl ester;
(R)-2-(3-{3-[[2-chloro-3-(trifluoromethyl)benzyl](2,2-diphenylethyl)amino]-1-methyl-propoxy}-phenyl)acetic acid;
(S)-2-(3-{3-[[2-chloro-3-(trifluoromethyl)benzyl](2,2-diphenylethyl)amino]-1-methyl-propoxy}-phenyl)acetic acid;
(R)-2-(3-{3-[[2-chloro-3-(trifluoromethyl)benzyl](2,2-diphenylethyl)amino]-3-methyl-propoxy}-phenyl)acetic acid;
(S)-2-(3-{3-[[2-chloro-3-(trifluoromethyl)benzyl](2,2-diphenylethyl)amino]-3-methyl-propoxy}-phenyl)acetic acid;
(R)-2-(3{3-[[2-fluoro-3-(trifluoromethyl)benzyl](2,2-diphenylethyl)amino]-2-methyl-propoxy}-phenyl)acetic acid;
(R)-2-(3-{3-[[3-(trifluoromethyl)-4-fluoro-benzyl](2,2-diphenylethyl)amino]-2-methyl-propoxy}-phenyl)acetic acid;
(R)-2-(3-{3-[[6-methyl-pyridin-2-ylmethyl](2,2-diphenylethyl)amino]-2-methyl-propoxy}-phenyl)acetic acid;
(R)-2-(3-{3-[[2,4-dimethoxy-benzyl](2,2-diphenylethyl)amino]-2-methyl-propoxy}-phenyl)acetic acid;
(R)-2-(3-{3-[[4-methoxy-benzyl](2,2-diphenylethyl)amino]-2-methyl-propoxy}-phenyl)acetic acid;
(R)-2-(3-{3-[[2-fluoro-4-methoxy-benzyl](2,2-diphenylethyl)amino]-2-methyl-propoxy}-phenyl)acetic acid;
(R)-2-(3-{3-[[3-fluoro-4-methoxy-benzyl](2,2-diphenylethyl)amino]-2-methyl-propoxy}-phenyl)acetic acid;
(R)-2-(3-{3-[[2,4-dimethoxybenzyl](2,2-diphenylethyl)amino]-1-methyl-propoxy}-phenyl)acetic acid;
(R)-2-(3-{3-[[4-methoxybenzyl](2,2-diphenylethyl)amino]-1-methyl-propoxy}-phenyl)acetic acid;
(R)-2-(3-{3-[[2-fluoro-4-methoxybenzyl](2,2-diphenylethyl)amino]-1-methyl-propoxy}-phenyl)acetic acid;
(R)-2-(3-{3-[[3-trifluoromethylbenzyl](2,2-diphenylethyl)amino]-1-methyl-propoxy}-phenyl)acetic acid;
(R)-2-(3-{3-[[2-fluoro-3-(trifluoromethyl)benzyl](2,2-diphenylethyl)amino]-5-methyl-propoxy}-phenyl)acetic acid;
(R)-2-(3-{3-[[3-(trifluoromethyl)-4-fluoro-benzyl](2,2-diphenylethyl)amino]-1-methyl-propoxy}-phenyl)acetic acid;
(R)-2-(3-{3-[[3-fluoro-4-methoxybenzyl](2,2-diphenyl-ethyl)amino]-1-methyl-propoxy}-phenyl)acetic acid;
(R)-2-(3-{3-[[2-chlorobenzyl](2,2-diphenylethyl)amino]-3-methyl-propoxy}-phenyl)acetic acid;
(R)-2-(3-{3-[[3-trifluoromethylbenzyl](2,2-diphenylethyl)amino]-3-methyl-propoxy}-phenyl)acetic acid;
(R)-2-(3-{3-[[2-fluoro-(3-trifluoromethyl)benzyl](2,2-diphenylethyl)amino]-3-methyl-propoxy}-phenyl)acetic acid;
(R)-2-(3-{3-[[3-trifluoromethyl-4-fluoro-benzyl](2,2-diphenylethyl)amino]-3-methyl-propoxy}-phenyl)acetic acid;
(R)-2-(3{3-[[2,4-dimethoxybenzyl](2,2-diphenylethyl)amino]-3-methyl-propoxy}-phenyl)acetic acid;
(R)-2-(3-{3-[[4-methoxybenzyl](2,2-diphenylethyl)amino]-3-methyl-propoxy}-phenyl)acetic acid;
(R)-2-(3-{3-[[2-fluoro-4-methoxybenzyl](2,2-diphenylethyl)amino]-3-methyl-propoxy}-phenyl)acetic acid;
(R)-2-(3-{3-[[2-chloro-3,4-dimethoxybenzyl](2,2-diphenylethyl)amino]-3-methyl-propoxy}-phenyl)acetic acid;
(R)-2-(3-{3-[[3-fluoro-4-methoxybenzyl](2,2-diphenylethyl)amino]-3-methyl-propoxy}-phenyl)acetic acid;
(3-{(R)-[(2,2-diphenyl-ethyl)-(4-isopropyl-benzyl)-amino]-methyl-propoxy}-phenyl)-acetic acid;

and pharmaceutically acceptable salts and solvates thereof.

Other compounds according to this invention include:
3-{3-[[2-chloro-3-(trifluoromethyl)benzyl](2,2-diphenylethyl)amino]-propoxy}-4-methyl-benzoic acid;
(3-{3-[[2,2-bis-(4-fluoro-phenyl)-ethyl]-(2-chloro-3-(trifluoromethyl)-benzyl)-amino]-propoxy}-phenyl)-acetic acid;
(3-{3-[[2,2-bis-(3-fluoro-phenyl)-ethyl]-(2-chloro-3-(trifluoromethyl)-benzyl)-amino]-propoxy}-phenyl)-acetic acid;
rac-(3-{3-[[2-phenyl-2-(o-chloro-phenyl)-ethyl]-(2-chloro-3-(trifluoromethyl)-benzyl)-amino]-propoxy}-phenyl)-acetic acid;
2-(3-{3-[(2-chloro-3-trifluoromethyl-benzyl)-2,2-diphenyl-ethyl-amino]-propoxy}-phenyl)-butyric acid;
2-(3-{3-[(2-chloro-3-trifluoromethyl-benzyl)-2,2-diphenyl-ethyl-amino]-propoxy}-phenyl)-pentanoic acid;
2-(3-{3-[(2-chloro-3-trifluoromethyl-benzyl)-2,2-diphenyl-ethyl-amino]-propoxy}-phenyl)-hexanoic acid;
2-(3-{3-[(2-chloro-3-trifluoromethyl-benzyl)-2,2-diphenyl-ethyl-amino]-propoxy}phenyl)-4-methyl-pentanoic acid;
2-(3-{3-[(2-chloro-3-trifluoromethyl-benzyl)-2,2-diphenyl-ethyl-amino]-propoxy}-phenyl)-2-ethyl-butyric acid methyl ester;
2-(3-{3-[(2-chloro-3-trifluoromethyl-benzyl)-2,2-diphenyl-ethyl-amino]-propoxy}-phenyl)-2-ethyl-butyric acid;
2-(3-{(R)-3-[(2-chloro-3-trifluoromethyl-benzyl)-2,2-diphenylethyl-amino]-butoxy}-phenyl)-2-methyl-propionic acid;
3-{3-[(2-chloro-3-trifluoromethyl-benzyl)-2,2-diphenyl-ethyl-amino]-propoxy}-benzoic acid methyl ester;
3-{3-[(2-chloro-3-trifluoromethyl-benzyl)-2,2-diphenyl-ethyl-amino]-propoxy}-benzoic acid;
2-bromo-5-{3-[(2-chloro-3-trifluoromethyl-benzyl)-2,2-diphenylethyl-amino]-propoxy}-benzoic acid;
(2-bromo-5-{3-[(2-chloro-3-trifluoromethyl-benzyl)-2,2-diphenylethyl-amino]-propoxy}-phenyl)-acetic acid;
N-(2-phenyl-2-cyclopentylethyl)-N-(2-chloro-3-trifluoromethylbenzyl)-3-(3-carboxymethylenephenoxy)propylamine;
N-(2,2-diphenylethyl)-N-(2-chloro-3-trifluoromethylbenzyl)-3-(3-carboxyphenoxy)propylamine;
N-(2,2-diphenylethyl)-N-(2-chloro-3-trifluoromethylbenzyl)-2,2-dimethyl-3-(3-aminopropoxy)phenylpropionic acid;

(3-chloro-4-{3-[(2-chloro-3-trifluoromethyl-benzyl)-2,2-diphenylethyl-amino]-propoxy}-phenyl)-acetic acid methyl ester;
(3-chloro-4-{3-[(2-chloro-3-trifluoromethyl-benzyl)-2,2-diphenylethyl-amino]-propoxy}-phenyl)-acetic acid;
2-(3-{3-[(2-chloro-3-trifluoromethyl-benzyl)-2,2-diphenyl-ethyl-amino]-propoxy}-phenyl)-2-methyl-propionic acid;
2-(3-{3-[(2-chloro-3-trifluoromethyl-benzyl)-2,2-diphenyl-ethyl-amino]-propoxy}-phenyl)-propionic acid;

and a stereoisomer, a stereoisomeric mixture or racemate thereof and a pharmaceutically acceptable salt or solvate thereof.

Preferred compounds of this invention include: (R)-2-(3-{3-[[2-chloro-3-(trifluoromethyl)benzyl](2,2-diphenylethyl)amino]-2-methyl-propoxy}-phenyl)acetic acid; (R)-2-(3-{3-[[2-chloro-3-(trifluoromethyl)benzyl](2,2-diphenylethyl)amino]-1-methyl-propoxy}-phenyl)acetic acid; (R)-2-(3-{3-[[2-chloro-3-(trifluoromethyl)benzyl](2,2-diphenylethyl)amino]-3-methyl-propoxy}-phenyl)acetic acid; (S)-2-(3-{3-[[2-chloro-3-(trifluoromethyl)benzyl](2,2-diphenylethyl)amino]-3-methyl-propoxy}-phenyl)acetic acid; 3-{3-[[2-chloro-3-(trifluoromethyl)benzyl](2,2-diphenylethyl)amino]-propoxy}-4-methyl-benzoic acid; 2-(3-{3-[(2-chloro-3-trifluoromethyl-benzyl)-2,2-diphenylethyl-amino]-propoxy}-phenyl)-propionic acid; (3-{3-[[2,2-(bis-(3-fluoro-phenyl)-ethyl]-(2-chloro-3-(trifluoromethyl)-benzyl)-amino]-propoxy}-phenyl)-acetic acid hydrochloride salt; rac-(3-{3-[[2-phenyl-2-(o-chloro-phenyl)-ethyl]-(2-chloro-3-(trifluoromethyl)-benzyl)-amino]-propoxy}-phenyl)-acetic acid hydrochloride salt; (3-chloro-4-{3-[(2-chloro-3-trifluoromethyl-benzyl)-2,2-diphenylethyl-amino]-propoxy}-phenyl)-acetic acid methyl ester; (R)-2-(3-{3-[[2,4-dimethoxybenzyl](2,2-diphenylethyl)amino]-3-methyl-propoxy}-phenyl)acetic acid; (R)-2-(3-{3-[[4-methoxybenzyl](2,2-diphenylethyl)amino]-3-methyl-propoxy}-phenyl)acetic acid; (R)-2-(3-{3-[[2-fluoro-4-methoxybenzyl](2,2-diphenylethyl)amino]-3-methyl-propoxy}-phenyl)acetic acid; (3-{(R)-[(2,2-diphenyl-ethyl)-(4-isopropyl-benzyl)-amino]-methyl-propoxy}-phenyl)-acetic acid; and 2-(3-{3-[(2-chloro-3-trifluoromethyl-benzyl)-2,2-diphenylethyl-amino]-propoxy}-phenyl)-2-methyl-propionic acid hydrochloride salt; and a stereoisomer, a stereoisomeric mixture or racemate thereof and a pharmaceutically acceptable salt or solvate thereof.

The term "LXR modulator," as used herein, means a small molecule that modulates the biological activities of LXRα and/or LXRβ. More specifically, such an LXR modulator either enhances or inhibits the biological activities of LXR. If such a modulator partially or completely enhances the biological activities of LXR, it is a partial or complete LXR agonist, respectively. If such a modulator partially or completely inhibits the biological activities of LXR, it is a partial or complete LXR agonist, respectively. Preferably, the LXR modulator compounds of this invention are LXR agonists. As used herein, the term "LXR agonist" refers to compounds which achieve at least 20% activation of LXR relative to 24(S),25-epoxycholesterol, the appropriate positive control in the HTRF assay described below in Test Method 1. It should be noted that to show activity in the specific Test Methods described herein, the LXR modulator compound must bind to the LXR nuclear receptor and recruit the specific peptide derived from the coactivator protein, SRC1, to the modulator compound-bound LXR complex. The compounds of this invention that form an LXR-modulator compound-complex and recruit SRC1, may also recruit at least one or more of the other >80 known different nuclear receptor cofactors. Recruiter peptides derived from any of these other nuclear receptor cofactors may be similarly prepared and assayed according to known procedures.

Compounds that are closely structurally related to the compounds of Examples 1-53 have been prepared that do not demonstrate at least 20% recruitment of the SRC1-derived peptide. It is anticipated, however, that such compounds do bind to LXR. It is further anticipated that such an LXR-modulator compound-complex will recruit at least one or more of the other >80 known different nuclear receptor cofactors. Examples of such compounds include: (3-[(R)-3-(2,2-diphenylethylamino)-1-methyl-propoxy]-phenyl}-acetic acid having a Q-$(CR^8R^9)_q$— group consisting of Q-$(CH_2)$— wherein Q is 2-chlorophenyl, 2-chloro-pyridin-3-yl, 6-methyl-pyridin-2-yl, 2-fluoro-5-trifluoromethylphenyl, 2-chloro-5-trifluoromethylphenyl, and 2-chloro-3,4-dimethoxyphenyl; {3-[(R)-3-[(2,2-diphenylethylamino)-2-methyl-propoxy]-phenyl}acetic acid having a Q-$(CR^8R^9)_q$— group consisting of Q-$(CH_2)$— wherein Q is 2-fluoro-5-trifluoromethylphenyl, 2-chloro-3,4-dimethoxyphenyl, 2-chloro-4-trifluoromethylphenyl, 3-bromo-4-methoxyphenyl, 2-fluoro-5-methoxyphenyl, 2,6-difluorophenyl, 3,5-dimethylphenyl, 2-bromophenyl, 3-iodophenyl, 4-(methylthio)phenyl, 3-furyl, 2-chloro-pyridin-3-yl, 2-benzyloxyphenyl, 3-methoxy-4-benzyloxyphenyl, 4-(N,N-dimethylamino-prop-1-yloxy)phenyl, and 4-acetylaminophenyl; {3-(R)-3-(2,2-diphenylethylamino)-butoxy]-phenyl}-acetic acid having a Q-$(CR^8R^9)_q$— group consisting of Q-$(CH_2)$— wherein Q is 2-chloro-pyridin-3-yl, 6-methyl-pyridin-2-yl, 2-fluoro-5-trifluoromethylphenyl, and 2-chloro-5-trifluoromethylphenyl; and (racemic)-{3-[3-[(2,2-diphenylethylamino)-hexyloxy]-phenyl}-acetic acid having a Q-$(CR^8R^9)_q$— group consisting of Q-$(CH_2)$— wherein Q is 2-fluoro-5-trifluoromethylphenyl and 2-fluoro-3-trifluoromethylphenyl.

The compounds of this invention are useful for a variety of medicinal purposes. The compounds of this invention may be used in methods for the prevention or treatment of LXR mediated diseases and conditions. This invention further provides compounds of this invention for use in the preparation of a medicament for the prevention or treatment of an LXR mediated disease or condition. LXR mediated diseases or conditions include inflammation, cardiovascular disease including atherosclerosis, arteriosclerosis, hypercholesteremia, and hyperlipidemia. In particular, the compounds of this invention are useful in the treatment and prevention of inflammation, cardiovascular disease including atherosclerosis and hypercholesteremia.

The present invention also provides a method for increasing reverse cholesterol transport, compounds of this invention for increasing reverse cholesterol transport and the use of compounds of this invention for the preparation of a medicament for increasing reverse cholesterol transport. Lipoprotein metabolism is a dynamic process comprised of production of triglyceride rich particles from the liver (as VLDL), modification of these lipoprotein particles within the plasma (VLDL to IDL to LDL) and clearance of the particles from the plasma, again by the liver. This process provides the transport of triglycerides and free cholesterol to cells of the body. Reverse cholesterol transport is the proposed mechanism by which peripheral cholesterol is returned to the liver from extra-hepatic tissue. The process is carried out by HDL cholesterol. The combination of lipoprotein production (VLDL, HDL) from the liver, modification of particles (all) within the plasma and subsequent clearance back to the liver, accounts for the steady state cholesterol concentration of the plasma. Without wishing to be bound by any particular theory, it is currently believed that the compounds of this invention increase reverse cholesterol transport by increasing cholesterol efflux from the arteries.

Additionally, this invention provides a method for inhibiting cholesterol absorption, compounds of this invention for inhibiting cholesterol absorption and the use of compounds of this invention for the preparation of a medicament for inhibiting cholesterol absorption. This invention also provides a method for increasing reverse cholesterol transport, compounds of this invention for increasing reverse cholesterol transport and the use of compounds of this invention for the preparation of a medicament for increasing reverse cholesterol transport.

The compounds of this invention may also be useful for the prevention or treatment of inflammation and neurodegenerative diseases or neurological disorders. Accordingly, this invention also provides a method for preventing or treating inflammation (See A. J. Fowler et al., J. Invest. Dermatol., 2003 February, 120 (2): 246-255 and S. B. Joseph, et al. Nat. Med., 2003 February, 9 (2): 213-219) and a method for preventing or treating neurodegenerative diseases or neurological disorders, particularly neurodegenerative diseases or disorders characterized by neuron degeneration, neuron injury or impaired plasticity or inflammation in the CNS (as disclosed in U.S. Provisional Patent Application No. 60/368, 424, filed 27 Mar. 2002). Particular diseases or conditions that are characterized by neuron degeneration and inflammation, and thus benefiting from the growth and/or repair of neurons include stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis. Diseases or conditions that are characterized by neuron degeneration and/or impaired plasticity include psychiatric disorders such as schizophrenia and depression. Particular diseases or conditions that are characterized by neuronal injury include those conditions associated with brain and/or spinal cord injury, including trauma.

The methods of the present invention are useful for the treatment of animals including mammals generally and particularly humans. The present invention further provides the use of compounds of this invention for the preparation of a medicament for increasing reverse cholesterol transport.

The methods of the present invention comprise the step of administering a therapeutically effective amount of a compound of this invention. As used herein, the term "therapeutically effective amount" refers to an amount of a compound of this invention which is sufficient to achieve the stated effect. Accordingly, a therapeutically effective amount of a compound of this invention used in the method for the prevention or treatment of LXR mediated diseases or conditions will be an amount sufficient to prevent or treat the LXR mediated disease or condition. Similarly, a therapeutically effective amount of a compound of this invention for use in the method of increasing reverse cholesterol transport will be an amount sufficient to increase reverse cholesterol transport.

The amount of a compound of this invention or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of LXR mediated diseases and conditions in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including increasing reverse cholesterol transport, and inhibiting cholesterol absorption.

In another embodiment, the present invention provides pharmaceutical compositions comprising a compound of this invention or a pharmaceutically acceptable salt or solvate thereof, as the active ingredient, and at least one pharmaceutical carrier or diluent. These pharmaceutical compositions may be used in the prophylaxis and treatment of the foregoing diseases or conditions and in cardiovascular therapies as mentioned above. The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of LXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

Suitable formulations for administration by inhalation include fine particle dusts or mists which may be generated by means of various types of metered dose pressurized aerosols, nebulisers, or insufflators.

For pulmonary administration via the mouth, the particle size of the powder or droplets is typically in the range 0.5-10 μM, preferably 1-5 μM, to ensure delivery into the bronchial tree. For nasal administration, a particle size in the range 10-500 μM is preferred to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 μL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insulator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

General Methods

In one embodiment of this invention, the method for the preparation of compounds of Formulas I, II, I-A and II-A comprises the steps of:

(a) reacting an alcohol having the formula: HO—$(CR^4R^5)_n$-L, where L is a leaving group, such as a halogen (iodide, bromide or chloride), sulfonate (tosylate, mesylate, triflate, etc.) or is a group that is converted to a leaving group (e.g., an alcohol) with a phenol having the formula:

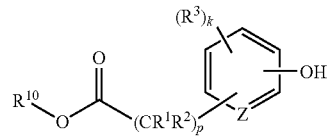

to form an aryl ether having the formula:

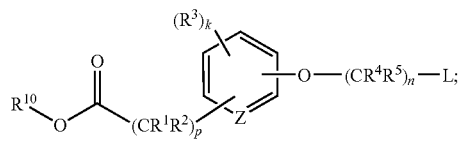

(b) reacting an amine having the formula

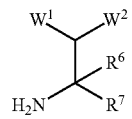

with and an aldehyde having the formula Q-CHO or a ketone to form a secondary amine having the formula:

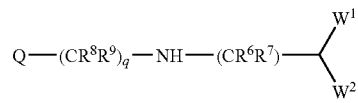

(c) reacting the ether formed in step (a) with the secondary amine formed in step (b) to form a compound of this invention having the formula:

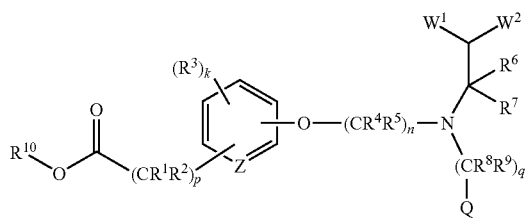

(d) when $R^{10}$ is other than H, optionally converting the compound formed in step (c) to the compound of this invention, wherein $R^{10}$ is H.

In another embodiment, the method for the preparation of compounds of Formulas I, II, I-A and II-A comprises the steps of:

(a) reacting an alcohol having the formula: HO—$(CR^4R^5)_n$-L, where L is a leaving group, such as a halogen (iodide, bromide or chloride), sulfonate (tosylate, mesylate, triflate, etc.) or is a group that is converted to a leaving group (e.g., an alcohol), with an amine having the formula:

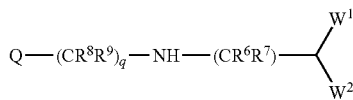

to form a tertiary amine having the formula:

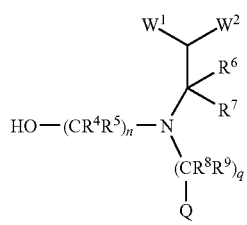

(b) reacting the tertiary amine formed in step (a) with a phenol having the formula:

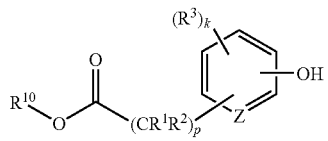

to form a compound of this invention having the formula:

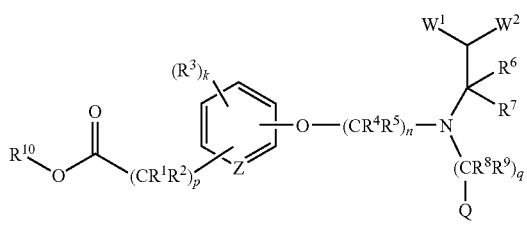

(c) when $R^{10}$ is other than H, optionally converting the compound formed in step (b) to the compound of this invention, wherein $R^{10}$ is H.

In another embodiment, the method for the preparation of compounds of Formulas I, II, I-A and II-A comprises the steps of:

(a) reacting an alcohol having the formula: HO—$(CR^4R^5)_n$-L, where L is a leaving group, such as a halogen (iodide, bromide or chloride) or sulfonate (tosylate, mesylate, triflate, etc.), with a phenol having the formula:

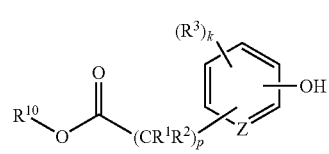

to form an ether-alcohol having the formula:

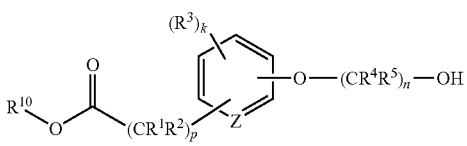

(b) converting alcohol moiety of the ether-alcohol formed in step (a) into L', where L' is a leaving group such as a halogen (iodide, bromide or chloride), sulfonate (tosylate, mesylate, triflate, etc.) or is a group that is converted to a leaving group (e.g., an alcohol) and treating the resulting compound with an amine having the formula:

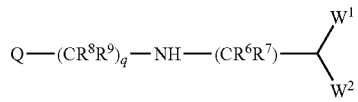

to form a compound of this invention having the formula:

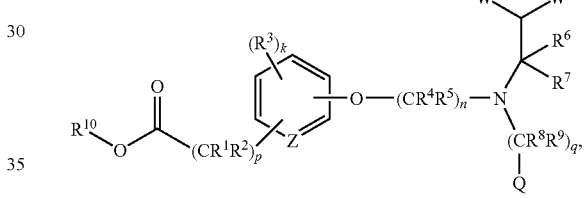

and (c) when $R^{10}$ is other than H, optionally converting the compound formed in step (b) to the compound of this invention, wherein $R^{10}$ is H.

Specific Methods

Compounds of Formulas I, II, I-A and II-A of this invention with alkyl substitution at the 2-propoxy position were prepared by methods analogous to those described in Scheme 1.

Scheme 1

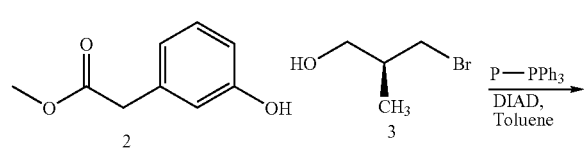

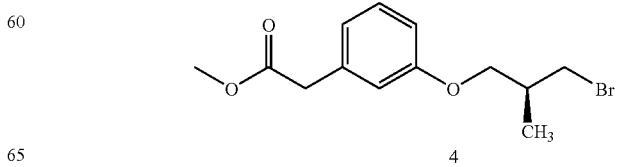

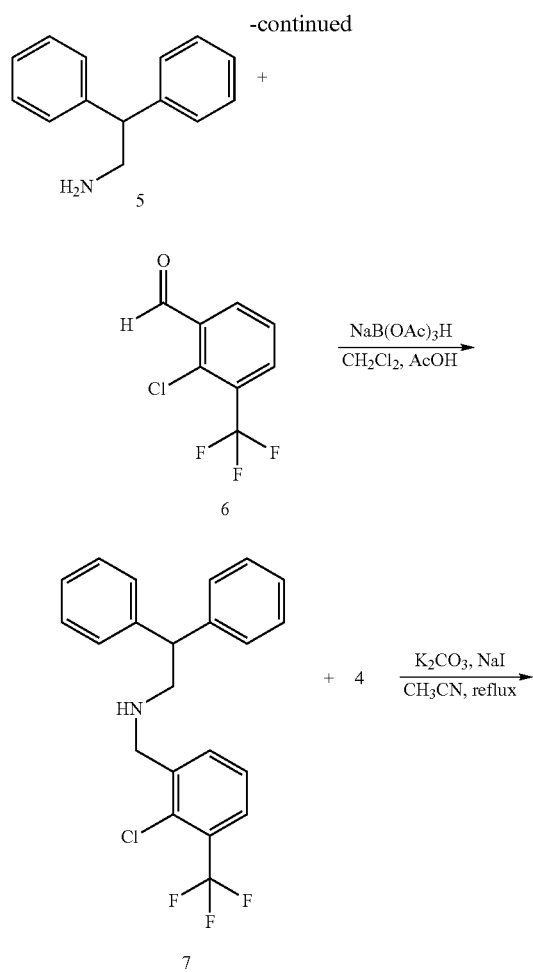
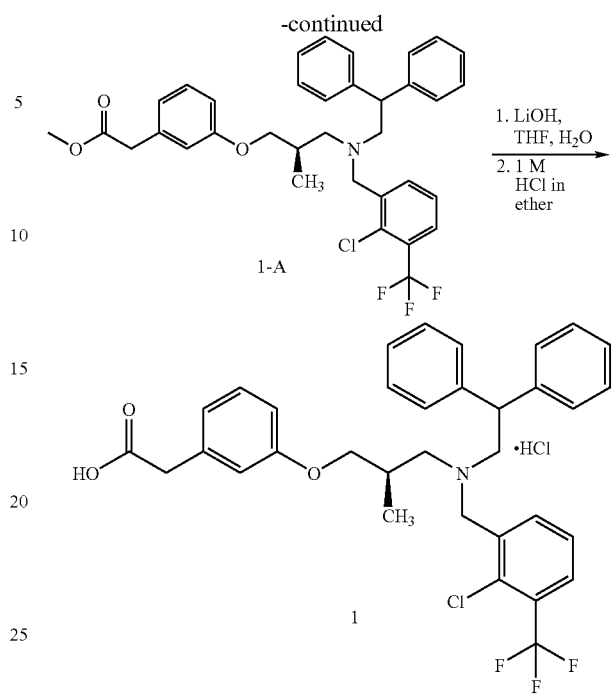

A phenol (2) was coupled to an alcohol (3) to give an aryl ether (4). A secondary amine (7) was prepared by reductive amination of a primary amine (5) with an aldehyde (6). The secondary amine (7) then displaced the alkyl bromine (4) to form a tertiary amine (1-A). The ester of this product was hydrolyzed, if desired, under the reaction conditions in Scheme 1 to afford the acid (1).

Compounds of Formulas I, II, I-A and II-A of this invention with alkyl substitution at the 1-propoxy or 3-propoxy positions were prepared by methods analogous to those described in Scheme 2.

Scheme 2

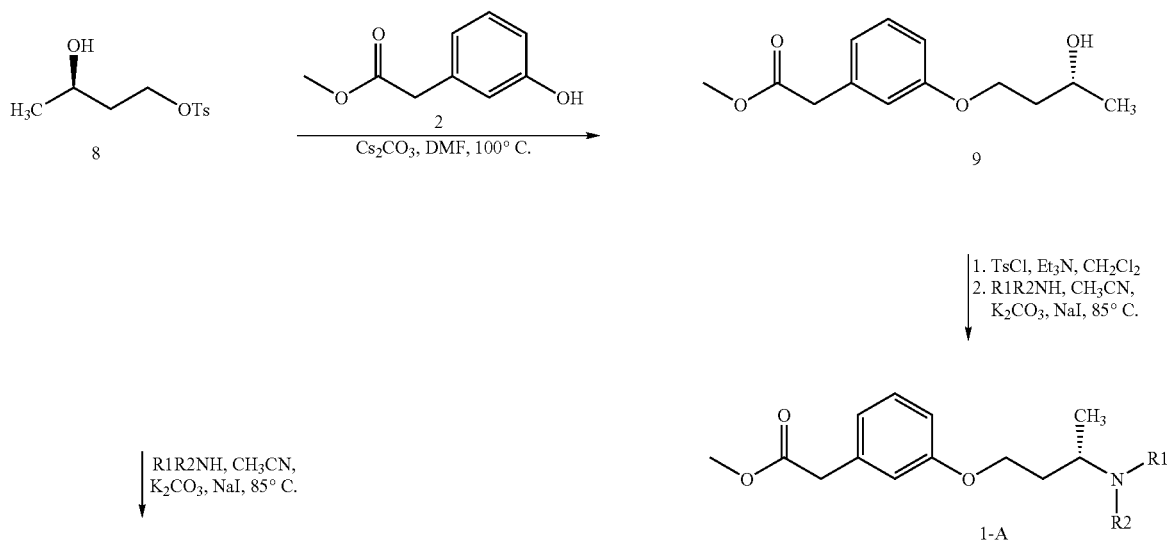

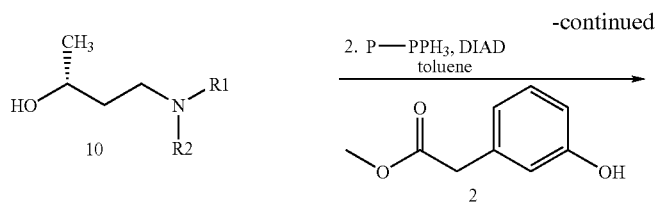
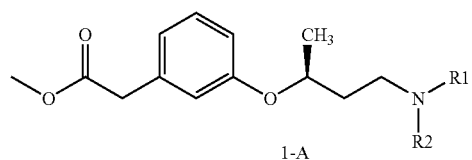

A common intermediate for both classes of compounds was the tosylate alcohol (8). The tosylate was displaced by a phenol (2) to give an aryl ether (9). A second tosyl group was introduced at the secondary alcohol and that was then displaced by a secondary amine to form a tertiary amine (1-A). Alternatively, the tosylate (8) could be displaced by the secondary amine to give a tertiary amine (10). Then, the phenol (2) was coupled to the secondary alcohol (10) to give an aryl ether (1-A). The ester product was hydrolyzed, if desired, under the identical reaction conditions given in Scheme I to afford the acid (1).

Compounds of Formulas I, II, I-A and II-A of this invention with an alkyl substituent on the aryl benzoic acid were prepared by methods analogous to those described in Scheme 3.

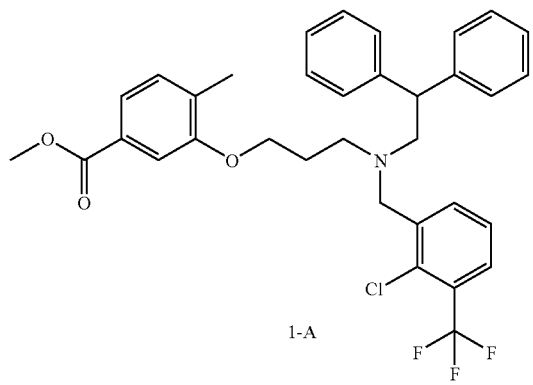

The secondary amine (7) displaced the bromine (11) to form a tertiary amine (12). This compound was then coupled to a phenol (13) to give an aryl ether (1-A). The ester of these products may be hydrolyzed, if desired, under the identical reaction conditions given in Scheme 1 to afford the corresponding acid (1).

In cases where a desired amine (5) was not commercially available, it may be prepared by methods analogous to those described Scheme 4.

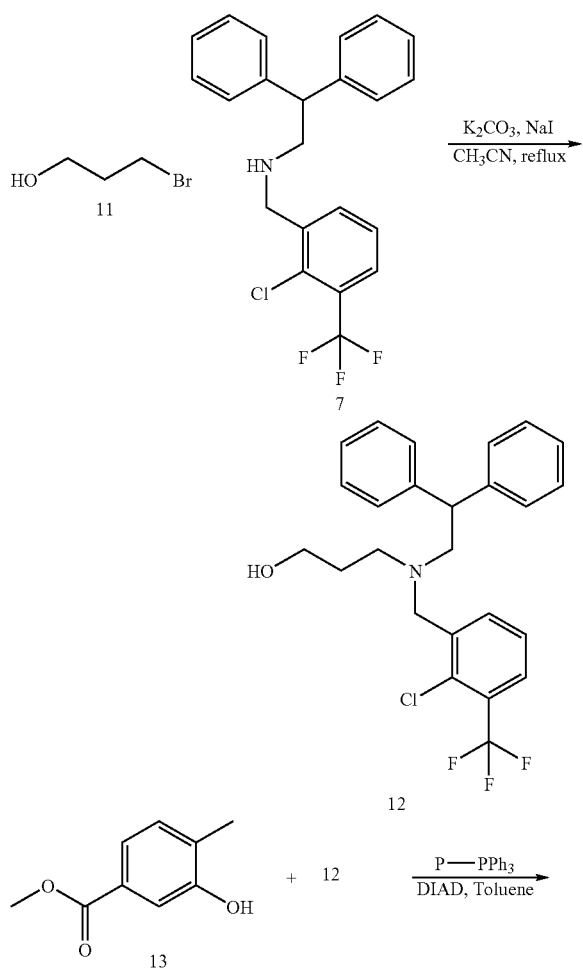
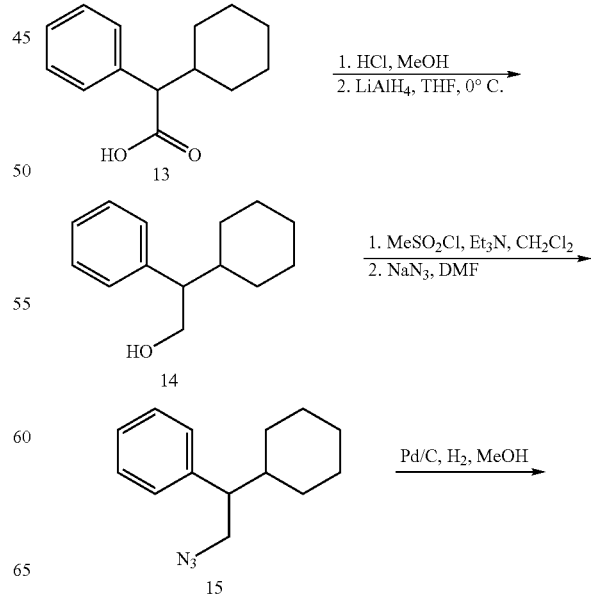

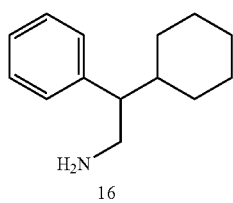

The methyl ester of a commercially available acid (13) may be formed under acidic conditions and reduced to an alcohol (14). The alcohol may be converted to a mesylate group which can be displaced by azide (15). Reduction of the azide can gave the primary amine (16) that may be used as a substitute for amine compound (5) in any of the other schemes outlined herein.

Compounds of Formulas I, II, I-A and II-A of this invention containing phenyl substitution in the $W^1$ and/or $W^2$ groups were prepared by methods analogous to those described in Scheme 5.

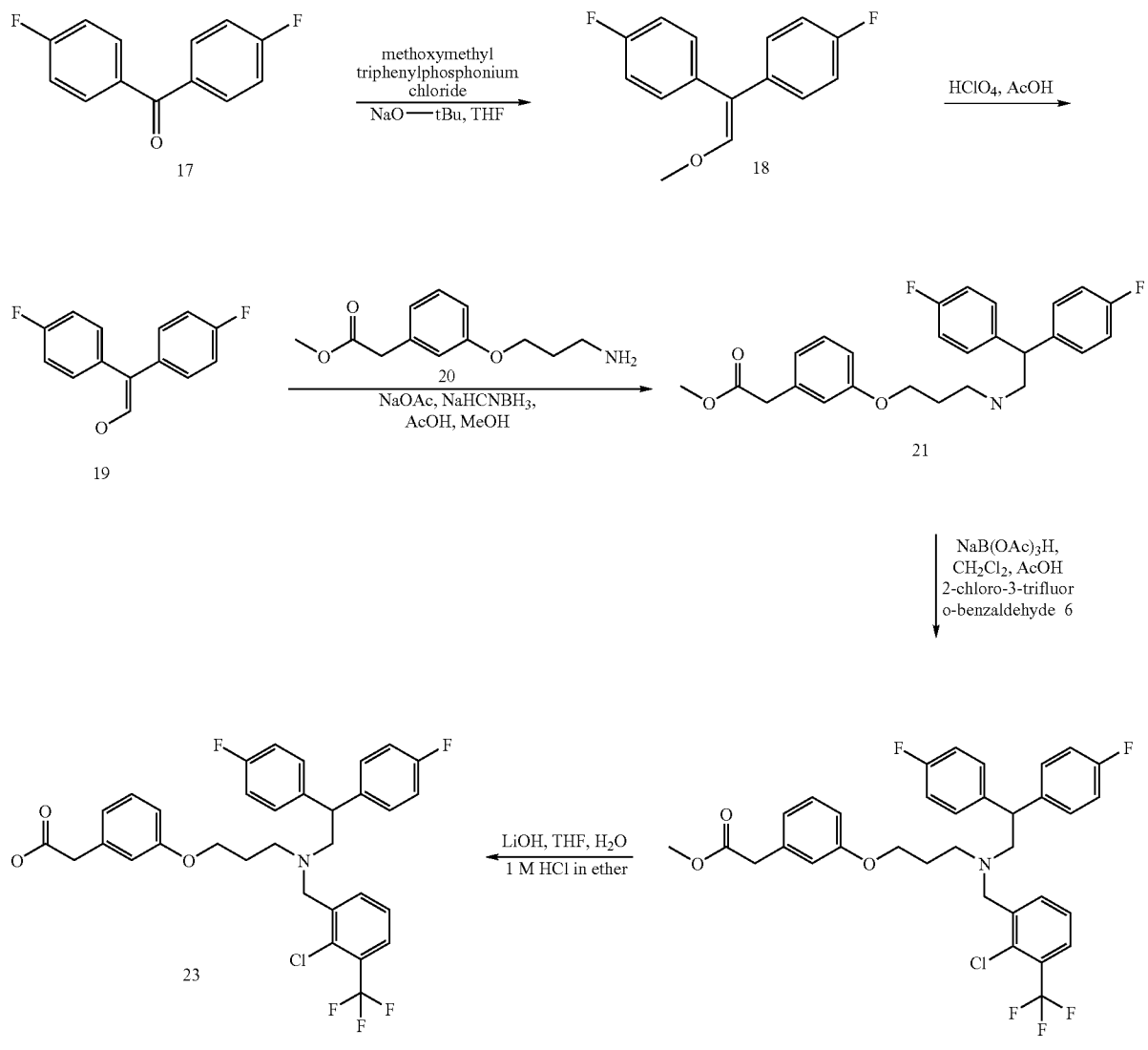

Treatment of ketone (17) under Wittig conditions formed the enol (18) which upon hydrolysis was transformed to the aldehyde (19) (Scheme 5). Reductive amination of (19) with the amine (20) yielded the secondary amine (21). Another reductive amination of (21) with aldehyde 6 formed the ester (22) which upon hydrolysis provided the acid (23).

Compounds of Formulas I, II, I-A and II-A of this invention containing substitution at positions $R^1$ and/or $R^2$ were prepared by methods analogous to those described in Scheme 6.

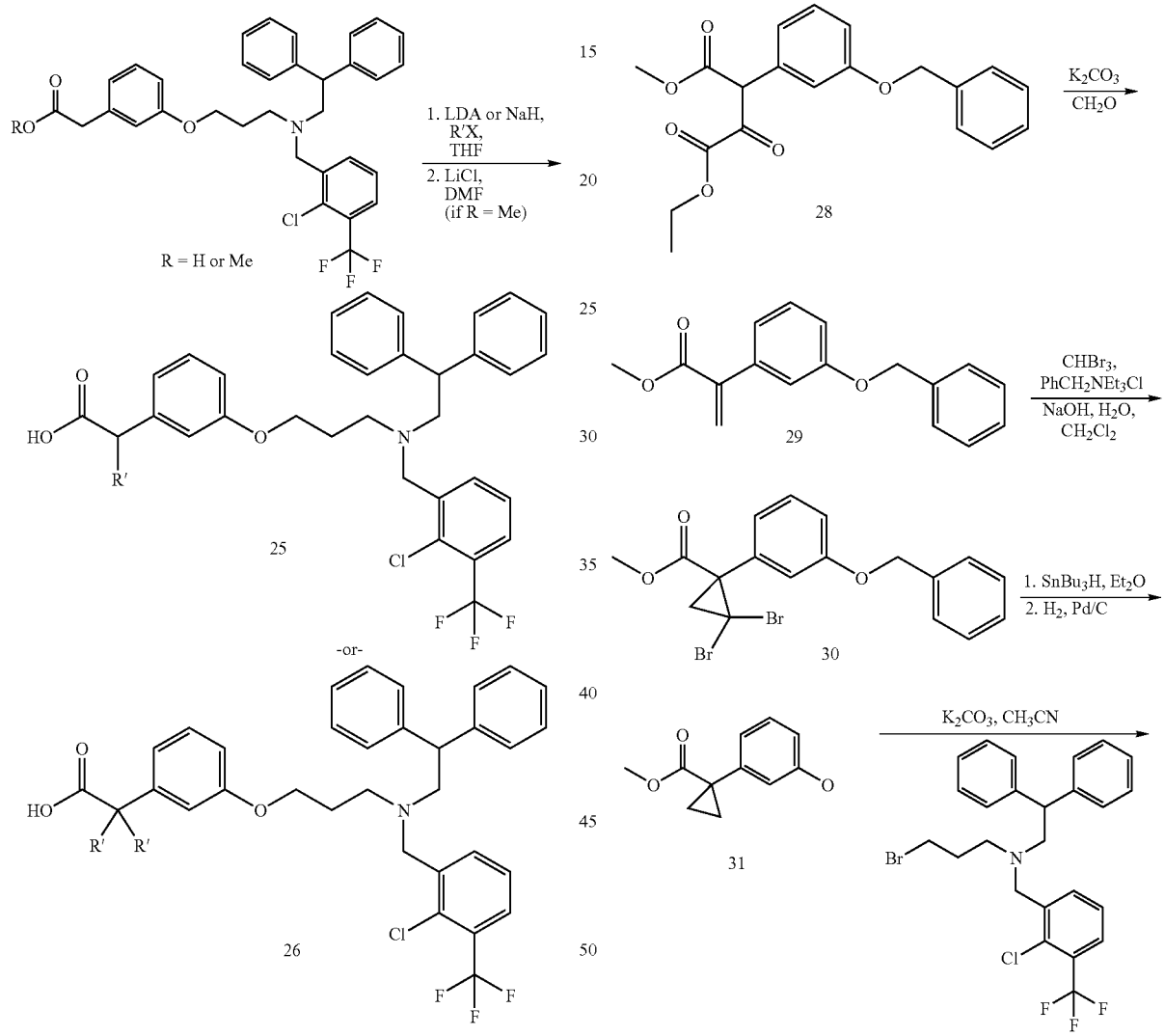

The alpha alkyl analogs of the carboxylic acids or esters (24) could be synthesized by treatment of (24) with base (either lithium diisopropylamine or sodium hydride) to form the anion and then subsequent addition of different alkyl halides to form either the mono alkylated compound (25) or the dialkylated compound (26) (Scheme 6). Subsequent hydrolysis of the ester (when R=Me) to the acid was achieved by treatment of the esters with lithium chloride in DMF.

Compounds of Formulas I, II, I-A and II-A of this invention containing spiro-ring substitution at positions $R^1$ and $R^2$ were prepared by methods analogous to those described in Scheme 7.

-continued

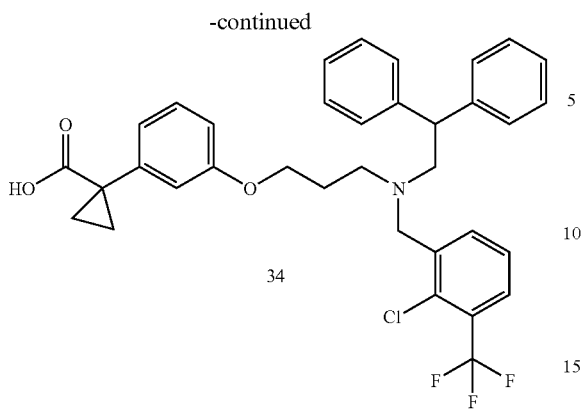

34

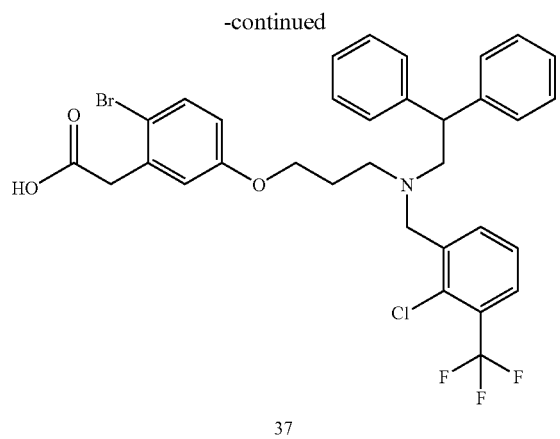

37

Treatment of the sodium anion of (27) with diethyl oxylate formed the tricarbonyl (28) (Scheme 7). Next, reaction of (28) with base and aqueous formaldehyde formed the alkene (29). Cyclopropanation of (29) led to the dibromide (30) which was converted to alcohol (31) through a two step process. Alkylation of (31) with the bromide (32) occurred smoothly to form the ester (33) which underwent a hydrolysis to form the acid (34). The bromide (32) was synthesized via alkylation of (7) with dibromopropane.

Selected compounds of Formulas I, II, I-A and II-A of this invention wherein p is 1, were prepared by methods analogous to those described in Scheme 8.

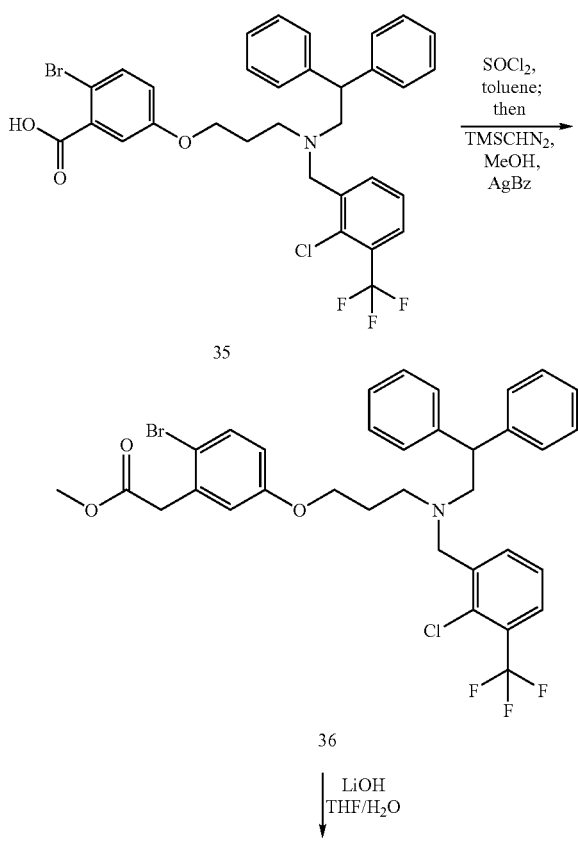

The acid (35) was converted to the acyl chloride which underwent an Arndt-Eistert reaction to form the ester (36) (Scheme 8). Hydrolysis of (36) with LiOH provided the acid (37).

Each of the above-described methods further include the optional step(s) of forming a pharmaceutically acceptable salt of a compound of this invention, and/or of forming a pharmaceutically acceptable solvate of a compound of this invention or a pharmaceutically acceptable salt thereof. The following intermediates are useful in the methods described herein to make the compounds of Formulas I, I-A, II and II-A:

(S)-[3-(2-Methyl-3-bromopropoxy)phenyl]acetic acid methyl ester;
(R)-[3-(2-Methyl-3-bromopropoxy)phenyl]acetic acid methyl ester;
(S)-4-[N-(2,2-Diphenylethyl)-N-(2-chloro-3-trifluoromethyl)amino]-butan-2-ol;
(R)-4-[N-(2,2-Diphenylethyl)-N-(2-chloro-3-trifluoromethyl)amino]-butan-2-ol;
(S)-[3-(3-Hydroxy-butoxy)-phenyl]-acetic acid methyl ester;
(R)-[3-(3-Hydroxy-butoxy)-phenyl]-acetic acid methyl ester;
(S)-2-(3-(3-[(2,2-Diphenylethyl)amino]-3-methyl-propoxy)-phenyl)acetic acid methyl ester;
(R)-2-(3-3-[(2,2-Diphenylethyl)amino]-3-methyl-propoxy)-phenyl)acetic acid methyl ester; and
N-(2,2-Diphenylethyl)-N-(3-hydroxy-propyl)-N-(2-chloro-3-trifluoromethyl-benzyl)amine, or pharmaceutically acceptable salts or solvates thereof.

The following Test Methods and Examples are intended for illustration only and are not intended to limit the scope of the invention in any way; the present invention being defined by the appended claims.

In the Test Methods and Examples, the following terms have the designated meaning: "pRSETa" is a known expression vector available from Invitrogen; "IPTG" means isopropyl β-D-thiogalactopyranoside; "PO$_4$" means phosphate; "PBS" means phosphate buffered saline; "TBS" means tris-buffered saline; EDTA means ethylenediamine tetraacetic acid; "DTT" means dithiothreitol; "FAF-BSA" means fatty-acid free bovine serum albumin; "SRC-1" means steroid receptor coactivator 1; "CS" means charcoal stripped; "nM" means nanomolar; "µM" means micromolar; "pM" means picomolar; "mM" means millimolar; "mmol" means millimoles; "g" means grams; "ng" means nanograms; "mg/ml" means milligram per milliliter; "µL" or "µl": means microliters; and "mL" or "ml" means milliliter.

Test Method 1: Ligand Sensing Assay (LiSA) for LXRβ Agonist Activity

This assay measures the recruitment of a peptide derived from the coactivator protein, SRC1, to the agonist-bound LXRβ. Peptides derived from other nuclear receptor cofactors may be similarly prepared and assayed.

To generate the human LXRβ ligand binding domain suitable for LiSA, a modified polyhistidine tag (MKKGHHHH-HHG) (SEQ ID No. 1) was fused in frame to the human LXRβ ligand binding domain (amino acids 185461 of Genbank accession number U07132) and subcloned into the expression vector pRSETa (Invitrogen) under the control of an IPTG inducible T7 promoter. The human LXRβ ligand binding domain was expressed in $E.\ coli$ strain BL21(DE3). Ten-liter fermentation batches were grown in Rich $PO_4$ media with 0.1 mg/mL Ampicillin at 25° C. for 12 hours, cooled to 9° C. and held at that temperature for 36 hours to a density of OD600=14. At this cell density, 0.25 mM IPTG was added and induction proceeded for 24 hours at 9° C., to a final OD600=16. Cells were harvested by centrifugation (20 minutes, 3500 g, 4° C.), and concentrated cell slurries were stored in PBS at −80° C.

Typically 25-50 g of cell paste is resuspended in 250-500 mL TBS, pH 8.0 (25 mM Tris, 150 mM NaCl). Cells are lysed by passing 3 times through an APV Rannie MINI-lab homogenizer and cell debris is removed by centrifugation (30 minutes, 20,000 g, 4° C.). The cleared supernatant is filtered through coarse pre-filters, and TBS, pH 8.0, containing 500 mM imidazole is added to obtain a final imidazole concentration of 50 mM. This lysate is loaded onto a column (XK-26, 10 cm) packed with Sepharose [Ni++ charged] Chelation resin (available from Pharmacia) and pre-equilibrated with TBS pH 8.0/50 mM imidazole. After washing to baseline absorbance with equilibration buffer, the column is washed with approximately one column volume of TBS pH −8.0 containing 95 mM imidazole. LXRβLBD(185-461) is eluted with a gradient from 50 to 500 mM imidazole. Column peak fractions are pooled immediately and diluted 5 fold with 25 mM Tris pH 8.0, containing 5% 1,2-propanediol, 0.5 mM EDTA and 5 mM DTT. The diluted protein sample is then loaded onto a column (XK-16, 10 cm) packed with Poros Ho resin (anion exchange). After washing to baseline absorbance with the dilution buffer the protein is eluted with a gradient from 50-500 mM NaCl. Peak fractions are pooled and concentrated using Centri-prep 10K (Amicon) filter devices and subjected to size exclusion, using a column (XK-26, 90 cm) packed with Superdex-75 resin (Pharmacia) pre-equilibrated with TBS, pH 8.0, containing 5% 1,2-propanediol, 0.5 mM EDTA and 5 mM DTT.

LXRβ protein was diluted to approximately 10 μM in PBS and five-fold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000× molar excess of Tris-HCl, pH 8. The modified LXRβ protein was dialyzed against 4 buffer changes, each of at least 50 volumes, PBS containing 5 mM DTT, 2 mM EDTA and 2% sucrose. The biotinylated LXRβ protein was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

The biotinylated protein was incubated for 20-25 minutes at a concentration of 5 nM in assay buffer (50 mM NaF, 50 mM MOPS-pH 7.5, 0.1 mg/ml FAF-BSA, 0.05 mM CHAPS, 10 mM DTT) with equimolar amounts of streptavidin-Allo-PhycoCyanin (APC, Molecular Probes). At the same time, the biotinylated peptide comprising amino acids 676-700 of SRC-1 (CPSSHSSLTERHKILHRLLQEGSPS-CONH2) (SEQ ID No. 2) at a concentration of 10 nM was incubated in assay buffer with a ½ molar amount of streptavidin-labelled Europium (Wallac) for 20-25 minutes. After the initial incubations are completed, a 20 molar excess of biotin was added to each of the solutions to block the unattached streptavidin reagents. After 20 min at room temp, the solutions were mixed yielding a concentration of 5 nM for the dye-labeled LXR protein and 10 nM for SRC-1 peptide.

49 μL of the protein/peptide mixture was added to each well of an assay plate containing 1 ul of test compound serial diluted in 100% DMSO. The final volume in each well was 0.05 mL, and the concentration in the well for the dye-labeled protein and peptide was 5 nM protein and 10 nM SRC1-peptide. The final test compound concentrations were between 33 pM and 20 μL. The plates were incubated at room temp 2-hours and then counted on a Wallac Victor V fluorescent plate reader.

In this assay 1 μM 24(S), 25-epoxycholesterol gave a reading of 20000 fluorescence units over a background reading of 10000 fluorescence units.

Test Method 2: Ligand Sensing Assay for LXRα Agonist Activity

The assay for LXRα was run according to the procedures of Test Method 1, above using his-tagged LXRα ligand binding domain (amino acids 183447 of Genbank accession number U22662, with the $14^{th}$ amino acid corrected to A from R). In this assay 1 μM 24(S), 25-epoxycholesterol gave a reading of 20000 fluorescence units over a background reading of 10000 fluorescence units.

EXAMPLE 1

(R)-2-(3-{3-[[2-Chloro-3-(trifluoromethyl)benzyl](2, 2-diphenylethyl)amino]-2-methyl-propoxy}-phenyl) acetic acid methyl ester

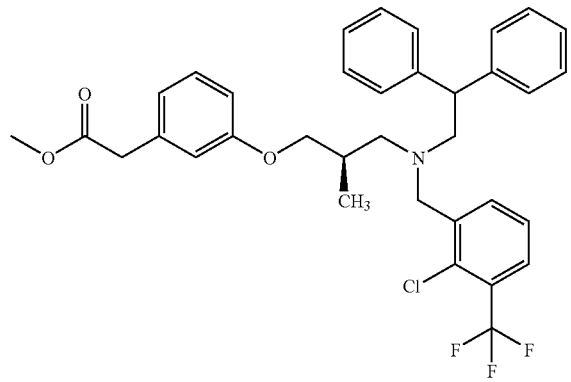

a) (3-Hydroxy-phenyl)-acetic acid methyl ester

To a stirring solution of (3-hydroxy-phenyl)-acetic acid (4.3 g, 0.028 mole) in methanol (30 mL) was added $H_2SO_4$ (1 mL) and the mixture was heated to reflux for 2 hours. The solvent was removed, the residue was washed with $H_2O$, and extracted three times with EtOAc (ethyl acetate). The combined organic layers were dried over $Na_2SO_4$, filtered, and concentrated to give 4.7 g (99% yield) of the title compound as an oil. MS (ESI) 167.0(M+H$^+$).

b) (S)-[3-(2-Methyl-3-bromopropoxy)phenyl]acetic acid methyl ester

To a stirring solution of (3-hydroxy-phenyl)-acetic acid methyl ester (0.75 g, 0.0045 mole) in anhydrous toluene (30 mL) was added (S)-(+)-3-bromo-2-methyl-1-propanol (0.90 g, 0.0059 mole). Polymer bound triphenylphosphine (2.4 g, 0.0072 mole, 3 mmol/g, Fluka Chemie) was then added, and the mixture was stirred for 15 minutes. The reaction mixture was then cooled to 0° C. and diisopropylazodicarboxylate (1.1 g, 0.00560 mole) was added in a dropwise fashion. After stirring at room temperature overnight, the crude reaction mixture was filtered, and the solid washed with toluene. After concentration of the filtrate in vacuo, the crude product was purified by column chromatography over silica gel (silica gel 60, EM Science) using 15% EtOAc:hexane as eluent to afford 0.86 g (63% yield) of the title compound as an oil: MS (ESI) 303.0 (M+2H$^+$).

c) N-(2,2-Diphenylethyl)-N-(2-chloro-3-trifluoromethyl-benzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36 g, 0.011 mole) and acetic acid (2.0 mL). The reaction mixture was stirred overnight. Solvent was removed, the residue was washed with saturated NaHCO$_3$, and extracted three times with EtOAc. The organic extracts were dried over Na$_2$SO$_4$, filtered, and concentrated. The crude mixture was subjected to column chromatography over silica gel (silica gel 60, EM Science) using 30% EtOAc: hexane as eluent to afford 3.0 g (76% yield) of the title compound as a yellow oil: MS (ESI) 390.0 (M+H$^+$).

d) (R)-2-(3-{3-[[2-Chloro-3-(trifluoromethyl)benzyl](2,2-diphenylethyl)amino]-2-methyl-propoxy}-phenyl)acetic acid methyl ester To a stirring solution of (S)-[3-(2-methyl-3-bromopropoxy)phenyl]acetic acid methyl ester (100 mg, 0.33 mmol) and N-(2,2-diphenylethyl)-N-(2-chloro-3-trifluoromethyl)amine (130 mg, 0.33 mmol) in acetonitrile (5 mL) was added solid K$_2$CO$_3$ (138 mg, 1.0 mmol) and NaI (149 mg, 1.0 mmol). The reaction was heated to reflux and stirred overnight. Upon cooling to room temperature, the reaction was filtered, washed with acetonitrile, and the filtrate was concentrated. The crude product was purified by preparative HPLC (TMC CombiPrep PDS, 75×30 mm, 25 mL/min, acetonitrile: H$_2$O, UV detection at 254 nm) to give 29 mg (14% yield) of title compound as a viscous oil. MS(ESI) 610.2(M$^+$).

EXAMPLE 2

(R)-2-(3-{3-[[2-Chloro-3-(trifluoromethyl)benzyl](2,2-diphenylethyl)amino]-2-methyl-propoxy}-phenyl) acetic acid hydrochloride salt

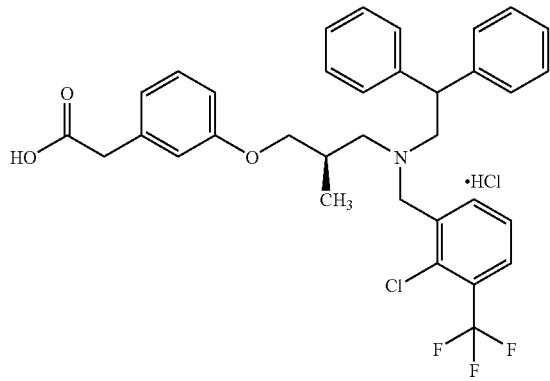

To a stirring solution of (R)-2-(3-{3-[[2-chloro-3-(trifluoromethyl)benzyl](2,2-diphenylethyl)amino]-2-methyl-propoxy}-phenyl)acetic acid methyl ester (22 mg, 0.0361 mmol) in THF (0.75 ml) and water (0.25 ml) was treated with LiOH (3.0 mg, 0.072 mmol). The reaction mixture was stirred overnight at RT. The reaction mixture was concentrated and 3 N HCl (aq.) was added until the pH was less than two. The aqueous layer was extracted three times with EtOAc, the combined organic layers were dried over sodium sulfate, filtered, and concentrated. The resulting amine/carboxylic acid was dissolved in Et$_2$O (diethylether) and acidified with 1.0 M HCl/Et$_2$O. The reaction mixture was concentrated in vacuo and dried under reduced pressure to give 18 mg (78% yield) of the title compound as a white solid. MS(ESI) 596.0 (M$^+$).

EXAMPLE 3

(S)-2-(3-{3-[[2-Chloro-3-(trifluoromethyl)benzyl](2,2-diphenylethyl)amino]-2-methyl-propoxy}-phenyl) acetic acid hydrochloride salt

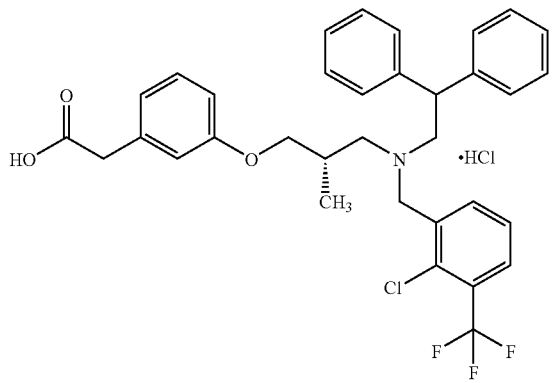

Following the procedure of Example 1 and 2 except (R)-(−)-3-bromo-2-methyl-1-propanol was used in step 1(b) instead of (S)-(+)-3-bromo-2-methyl-1-propanol, the title compound was isolated to give 37 mg (12%) of a white solid. MS(ESI) 596.0(M$^+$).

EXAMPLE 4

(R)-2-(3-{3-[[2-Chloro-3-(trifluoromethyl)benzyl](2,2-diphenylethyl)amino]-1-methyl-propoxy}-phenyl) acetic acid methyl ester

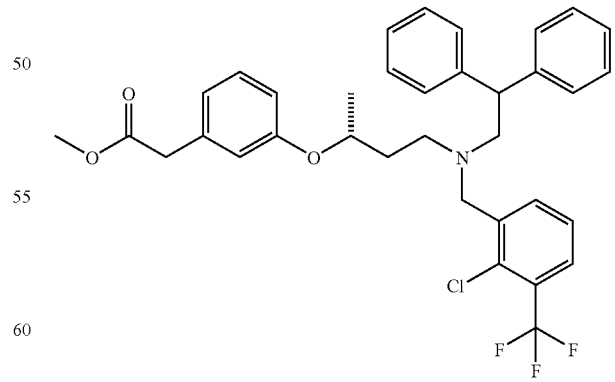

a) Toluene-4-sulfonic acid-(S)-3-hydroxy-butyl ester

To a stirring solution of (S)-1,3-butanediol (1.0 g, 0.01 mmol) and triethylamine (1.39 g, 0.014 mmol) in dichloromethane (10 mL) at −20° C. was added dropwise p-toluenesulfonyl chloride and the mixture was stirred for 2 h. The reaction mixture was then warmed to RT and stirred overnight. The reaction mixture was poured into cold H₂O (20 mL), and extracted three times with dichloromethane. The organic extracts were then washed with brine. The organic layer was dried over sodium sulfate, filtered, and concentrated in vacuo to give 2.6 g (96% yield) of title compound as an oil. MS(ESI) 244.8(M⁺). The crude tosylate was used without further purification.

b) (S)-4-[N-(2,2-Diphenylethyl)-N-(2-chloro-3-trifluoromethyl)amino]-butan-2-ol

To a stirring solution of N-(2,2-diphenylethyl)-N-(2-chloro-3-trifluoromethyl)amine (160 mg, 0.409 mmol) and toluene-4-sulfonic acid-(S)-3-hydroxy-butyl ester (100 mg, 0.409 mmol) in acetonitrile (5 mL) was added solid K₂CO₃ (170 mg, 1.23 mmol) and NaI (184 mg 1.23 mol). The reaction mixture was heated to reflux and stirred overnight. The mixture was cooled to RT, filtered, and the filtrate was concentrated. The crude product was purified by preparative HPLC (TMC CombiPrep PDS, 75×30 mm, 25 mL/min, acetonitrile: H₂O, UV detection at 254 nm) to give 110 mg (58% yield) of the title compound as an oil. MS(ESI) 462.0 (M+H⁺).

c) (R)-2-(3-{3-[[2-Chloro-3-(trifluoromethyl)benzyl](2,2-diphenylethyl)amino]-1-methyl-propoxy}phenyl)acetic acid methyl ester To a stirring solution of (3-hydroxy-phenyl)-acetic acid methyl ester (36 mg, 0.217 mmol) in anhydrous toluene (5 mL) was added (S)₄-[N-(2,2-diphenylethyl)-N-(2-chloro-3-trifluoromethyl)amino]-butan-2-ol (100 mg, 0.217 mmol). Polymer bound triphenylphosphine (115 mg, 0.346 mmol, 3 mmol/g, Fluka Chemie) was then added, and the mixture was stirred for 15 minutes. The reaction mixture was then cooled to 0° C. and diisopropylazodicarboxylate (54 mg, 0.269 mmol) was added in a dropwise fashion. The reaction mixture was stirred overnight at room temperature. The reaction mixture was next filtered and the remaining solid was washed with toluene. The filtrate was concentrated and the crude product was purified by preparative HPLC (TMC CombiPrep PDS, 75×30 mm, 25 mL/min, A: acetonitrile B: H₂O, A: 85 to 100% during 10 min, UV detection at 254 nm) to give 56 mg (42% yield) of title compound as a viscous oil. MS(ESI) 610.0(M⁺).

EXAMPLE 5

(R)-2-(3-{3-[[2-Chloro-3-(trifluoromethyl)benzyl](2,2-diphenylethyl)amino]-1-methyl-propoxy}-phenyl)acetic acid hydrochloride salt

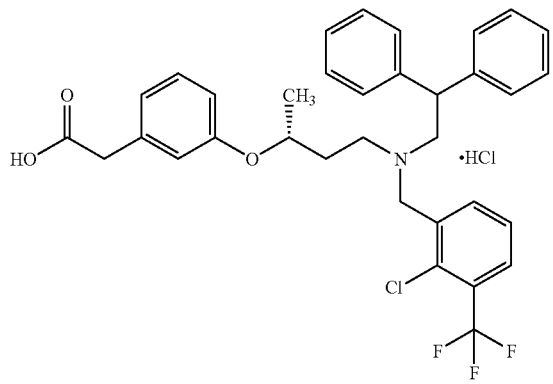

Following the procedure of Example 2 except (R)-2-(3-{3-[[2-chloro-3-(trifluoromethyl)benzyl](2,2-diphenylethyl)amino]-1-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid 48 mg (98% yield). MS(ESI) 596.0(M⁺).

EXAMPLE 6

(S)-2-(3-{3-[[2-Chloro-3-(trifluoromethyl)benzyl](2,2-diphenylethyl)amino]-1-methyl-propoxy}-phenyl) acetic acid hydrochloride salt

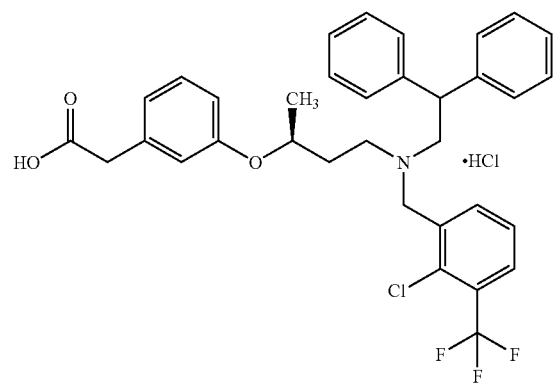

Following the procedure of Example 4 and 5 except (R)-1,3-butanediol was used in step 4(a) instead of (S)-1,3-butanediol, the title compound was isolated to give a white solid 86 mg (25% overall). MS(ESI) 596.0(M⁺).

EXAMPLE 7

(R)-2-(3-{3-[[2-Chloro-3-(trifluoromethyl)benzyl](2,2-diphenylethyl)amino]-3-methyl-propoxy}phenyl) acetic acid hydrochloride salt

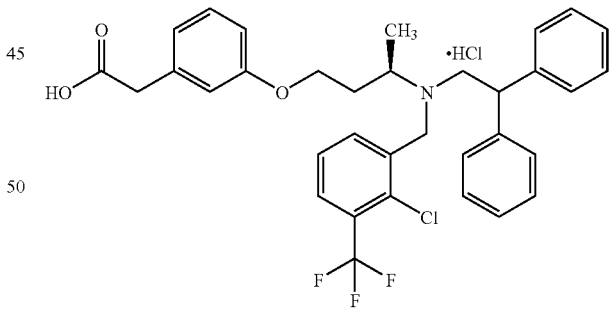

a) (S)-[3-(3-Hydroxy-butoxy)-phenyl]-acetic acid methyl ester

To a stirring solution of (3-hydroxy-phenyl)-acetic acid methyl ester (0.93 g, 0.0056 mole) and toluene-4-sulfonic acid-(S)-3-hydroxy-butyl ester (1.5 g, 0.0061 mole) in anhydrous DMF (10 mL) was added Cs₂CO₃ (2.0 g, 0.006 mole). The reaction was heated to 100° C. and stirred for 4 hours. The mixture was cooled to RT and filtered. The filtrate was poured into H₂O (50 mL) and extracted three times with EtOAc. The combined organic layers were dried over sodium sulfate, filtered, and concentrated. The crude product was subjected to column chromatography over silica gel (silica gel 60, EM Science) using 30% EtOAc:hexane as eluent to afford 0.59 g (44% yield) of the title compound as an oil: MS (ESI) 239.0 (M+H$^+$).

b) (S)-{3-[3-(Toluene-4-sulfonyloxy)-butoxy]-phenyl}-acetic acid methyl ester

To a stirring solution of (S)-[3-(3-hydroxy-butoxy)-phenyl]-acetic acid methyl ester (589 mg, 2.47 mmol) and triethylamine (376 mg, 3.71 mmol) in dichloromethane (10 mL) at 0° C. was added p-toluenesulfonyl chloride (944 mg, 4.95 mmol). The reaction was then stirred at RT for 30 min. and refluxed overnight. The reaction mixture was poured into H$_2$O (40 mL) and extracted three times with dichloromethane. The combined organic extracts were dried over sodium sulfate, filtered, and concentrated. The crude product was purified by column chromatography over silica gel (silica gel 60, EM Science) using 15% EtOAc:hexane as eluent to afford 0.61 g (63% yield) of the title compound as an oil: MS (ESI) (M+H$^+$).

c) (R)-2-(3-{3-[(2,2-Diphenylethyl)amino]-3-methyl-propoxy}-phenyl)acetic acid methyl ester To a stirring solution of 2,2-diphenethylamine (151 mg, 0.765 mmol) and (S)-{3-[3-(toluenesulfonyloxy)-butoxy]-phenyl}-acetic acid methyl ester (300 mg, 0.765 mmol) in acetonitrile (5 mL) was treated with solid K$_2$CO$_3$ (317 mg, 2.30 mmol). The reaction was heated to reflux and stirred for 48 hours. Upon cooling to room temperature, the reaction was filtered, washed with acetonitrile, and the filtrate was concentrated. The crude product was purified by column chromatography over silica gel (silica gel 60, EM Science) using 50% EtOAc:hexane as eluent to afford 200 mg (63% yield) of the title compound as an oil: MS (ESI) 418.2 (M+H$^+$).

d) (R)-2-(3-{3-[[2-Chloro-3-(trifluoromethyl)benzyl](2,2-diphenylethyl)amino]-3-methyl-propoxy}-phenyl)acetic acid methyl ester To a stirring solution of (R)-2-(3-{3-(2,2-diphenylethyl)amino]-3-methyl-propoxy}phenyl)acetic acid methyl ester (150 mg, 0.359 mmol) and 2-chloro-3-trifluoromethylbenzaldehyde (164 mg, 0.79 mmol) in dichloromethane (5 ml) was added sodium triacetoxyborohydride (168 mg, 0.79 mmol) and acetic acid (10 drops). The reaction mixture was stirred at RT for three days. Solvent was next removed, the residue was dissolved in EtOAc, and then washed with saturated aqueous NaHCO$_3$. The EtOAc layer was dried over Na$_2$SO$_4$, filtered, and concentrated. The crude mixture was purified by preparative HPLC (TMC CombiPrep PDS, 75×30 mm, 25 mL/min, acetonitrile: H$_2$O, UV detection at 254 nm) to give 140 mg (64%) of the title compound as a viscous oil. MS(ESI) 610.0(M$^+$).

e) (R)-2-(3-{3-[[2-Chloro-3-(trifluoromethyl)benzyl](2,2-diphenylethyl)amino]-3-methyl-propoxy}-phenyl)acetic acid hydrochloride salt Following the procedure of Example 2 except (R)-2-(3-{3-[[2-chloro-3-(trifluoromethyl)benzyl](2,2-diphenylethyl) amino]-3-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid (100 mg, 89%). MS(ESI) 596.0 (M$^+$).

EXAMPLE 8

(S)-2-(3-{3-[[2-Chloro-3-(trifluoromethyl)benzyl](2,2-diphenylethyl)amino]-3-methyl-propoxy}-phenyl) acetic acid hydrochloride salt

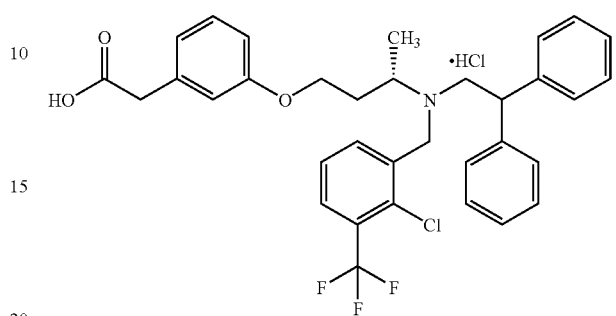

Following the procedure of Example 7(a)-(e) except toluene-4-sulfonic acid-(R)-3-hydroxy-butyl ester was used instead of toluene-4-sulfonic acid-(S)-3-hydroxy-butyl ester in step 7(a), the title compound was isolated to give a white solid, 120 mg (11% overall). MS(ESI) 596.0 (M$^+$).

EXAMPLE 9

3-{3-[[2-Chloro-3-(trifluoromethyl)benzyl](2,2-diphenylethyl)amino]-propoxy}-4-methyl-benzoic acid hydrochloride salt

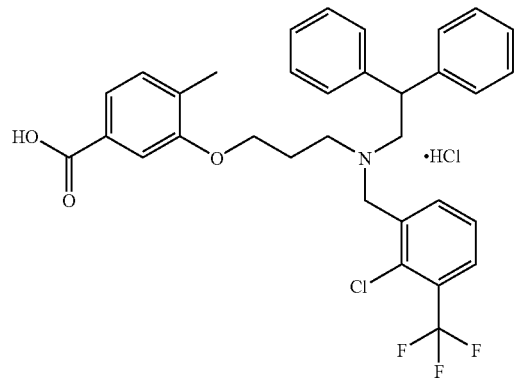

a) N-(2,2-Diphenylethyl)-N-(3-hydroxy-propyl)-N-(2-chloro-3-trifluoromethyl-benzyl)amine To a stirring solution of 3-bromo-propanol (77 ul, 0.84 mmol) in acetonitrile (10 ml) was added NaI (0.25 g, 1.7 mmol) and K$_2$CO$_3$ (0.23 g, 1.7 mmol). The mixture was stirred at 85° C. for 1 h, and then N-(2,2-diphenylethyl)-N-(2-chloro-3-trifluoromethyl-benzyl)amine (0.43 g, 1.12 mmol) was added. The reaction mixture was heated at 85° C. overnight. Solvent was removed, the residue was washed with H$_2$O, and extracted twice with EtOAc. The EtOAc extracts were dried over Na$_2$SO$_4$, filtered, and concentrated. The crude mixture was purified by preparative HPLC (TMC CombiPrep PDS, 75×30 mm, 25 mL/min, acetonitrile:H$_2$O, UV detection at 254 nm) to give 225 mg (60%) of the title compound as a white solid. MS (ESI) 448.0 (M+H$^+$).

b) 3-Hydroxy-4-methyl-benzoic acid methyl ester

To a stirring solution of 3-hydroxy-4-methyl-benzoic acid (2.0 g, 13.1 mmol) in methanol (MeOH, 50 ml) was added conc. $H_2SO_4$ (1.5 ml). The mixture was refluxed overnight, and then concentrated. The crude ester was dissolved in EtOAc (50 ml), and washed with $H_2O$ (50 mL). The organic layer was dried over $Na_2SO_4$, filtered, and concentrated. The title compound was isolated to give a white solid (2.1 g, 98% yield). $^1$H-NMR (400 MHz, $CDCl_3$) δ 2.32 (s, 3H), 3.93 (s, 3H), 7.19 (d, 1H, J=7.7 Hz), 7.52 (d, 1H, J=7.7 Hz), and 7.64 (s, 1H).

c) 3-{3-[[2-Chloro-3-(trifluoromethyl)benzyl](2,2-diphenylethyl)amino]-propoxy}-4-methyl-benzoic acid methyl ester To a stirring solution of 3-hydroxy-4-methyl-benzoic acid methyl ester (102 mg, 0.61 mmol) in anhydrous toluene (5 mL) was added N-(2,2-diphenylethyl)-N-(3-hydroxy-propyl)-N-(2-chloro-3-trifluoromethyl-benzyl)amine (211 mg, 0.47 mmol). Polymer bound triphenylphosphine (250 mg, 0.75 mmol, 3 mmol/g, Fluka Chemie) was then added, and the mixture stirred for 15 minutes. The reaction mixture was then cooled to 0° C. and diisopropylazodicarboxylate (115 ul, 0.58 mmol) was added in a dropwise fashion. After stirring at room temperature overnight, the crude reaction mixture was filtered and the resulting solid was washed with toluene. The filtrate was concentrated and the crude product was purified by preparative HPLC (TMC CombiPrep PDS, 75×30 mm, 25 mL/min, acetonitrile: $H_2O$, UV detection at 254 nm) to give 150 mg (54% yield) of the title compound as a viscous oil. MS(ESI) 596.0($M^+$).

d.) 3-{3-[[2-Chloro-3-(trifluoromethyl)benzyl](2,2-diphenylethyl)amino]-propoxy}-4-methyl-benzoic acid hydrochloride salt Following the procedure of Example 2 except 3-{3-[[2-chloro-3-(trifluoromethyl)benzyl](2,2-diphenylethyl)amino]-propoxy}-4-methyl-benzoic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid (106 mg, 91% yield). MS(ESI) 582.0 ($M^+$).

EXAMPLE 10

(R)-2-(3-{3-[[2-Fluoro-3-(trifluoromethyl)benzyl](2,2-diphenylethyl)amino]-2-methyl-propoxy}-phenyl) acetic acid hydrochloride salt

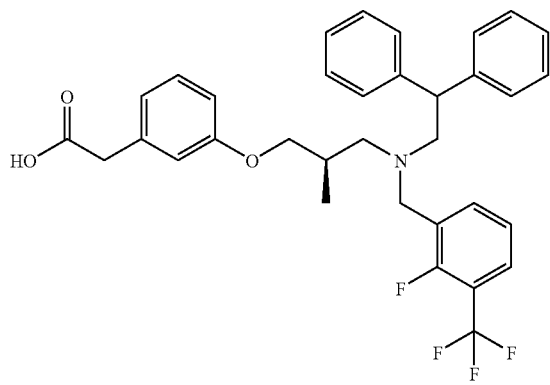

a) (R)-2-(3-{3-[(2,2-diphenylethyl)amino]2-methyl-propoxy}-phenyl)acetic acid methyl ester To a stirring solution of (S)-[3-(2-methyl-3-bromopropoxy)phenyl]acetic acid methyl ester (2.68 g, 8.90 mmol) and 2,2-diphenethylamine (1.75 g, 8.90 mmol) in acetonitrile (15 mL) was added solid $K_2CO_3$ (3.69 g, 26.7 mmol) and NaI (4.00 g, 26.7 mmol). The reaction was heated to reflux and stirred overnight. Upon cooling to RT, the reaction was filtered, washed with acetonitrile, and the filtrate was concentrated. The crude product was purified by flash silica gel chromatography (3:2 hexane:EtOAc) to provide the title compound as a white powder, 1.60 g (43%). MS (ESI) 418.4 ($M+H^+$).

b) (R)-2-(3-{3-[(2,2-diphenylethyl)amino]2-methyl-propoxy}-phenyl)acetic acid

Following the procedure of Example 2, except using (R)-2-(3-{3-[(2,2-diphenylethyl)amino]2-methyl-propoxy}-phenyl)acetic acid methyl ester instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid, 1.6 g (100% yield). MS(ESI) 404.2 ($M+H^+$).

c) (R)-2-(3-{3-[[2-Fluoro-3-(trifluoromethyl)benzyl](2,2-diphenylethyl)amino]-2-methyl-propoxy}-phenyl)acetic acid hydrochloride salt Following the procedure of Example 7(d) except (R)-2-(3-{3-[(2,2-diphenylethyl)amino]2-methyl-propoxy}phenyl) acetic acid and 2-fluoro-3-trifluoromethylbenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The resulting amine/carboxylic acid was dissolved in $Et_2O$ (diethylether) and acidified with 1.0 M $HCl/Et_2O$. The reaction mixture was concentrated in vacuo and dried under reduced pressure to give the title compound as a white solid, 73 mg (68%). MS (ESI) 580.4 ($M+H^+$).

EXAMPLE 11

(R)-2-(3-{3-[[3-(trifluoromethyl)-4-fluoro-benzyl](2,2-diphenylethyl)amino]-2-methyl-propoxy}phenyl) acetic acid hydrochloride salt

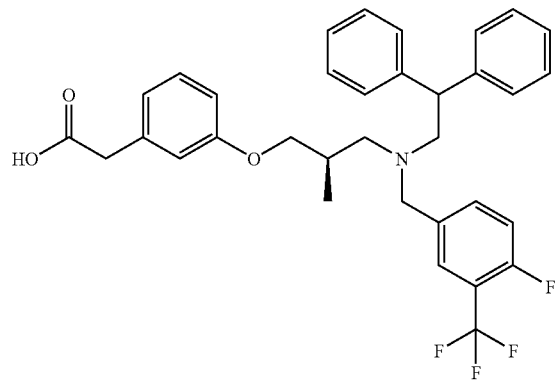

Following the procedure of Example 7(d) except (R)-2-(3-{3-[(2,2-diphenylethyl)amino]2-methyl-propoxy}phenyl) acetic acid and 3-trifluoromethyl-4-fluoro-benzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The resulting amine/carboxylic acid was dissolved in Et₂O (diethylether) and acidified with 1.0 M HCl/Et₂O. The reaction mixture was concentrated in vacuo and dried under reduced pressure to give the title compound as a white solid, 72 mg (67%). MS (ESI) 580.4 (M+H⁺).

EXAMPLE 12

(R)-2-(3-{3-[[6-Methyl-pyridin-2-ylmethyl](2,2-diphenylethyl)amino]-2-methyl-propoxy}-phenyl)acetic acid hydrochloride salt

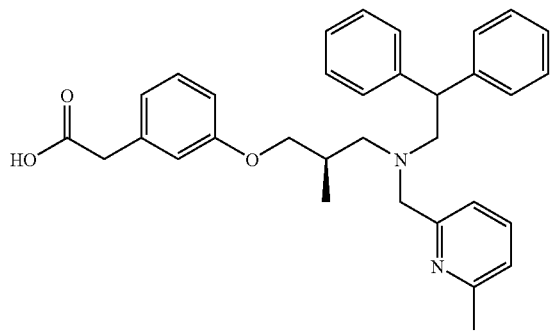

Following the procedure of Example 7(d) except (R)-2-(3-{3-[(2,2-diphenylethyl)amino]2-methyl-propoxy}-phenyl) acetic acid and 6-methyl-2-pyridinecarboxaldehyde were used instead of (R)-2-(3-{3-(2,2-diphenylethyl)amino]-3-methyl-propoxy}phenyl)acetic acid methyl ester and 2-chloro-3-trifluoromethylbenzaldehyde in step (d) the corresponding carboxylic acid was obtained. The resulting amine/carboxylic acid was dissolved in Et₂O (diethylether) and acidified with 1.0 M HCl/Et₂O. The reaction mixture was concentrated in vacuo and dried under reduced pressure to give the title compound as a white solid, 89 mg (95%). MS (ESI) 509.4 (M+H⁺).

EXAMPLE 13

(R)-2-(3-{3-[[2,4-dimethoxy-benzyl](2,2-diphenyl-ethyl)amino]-2-methyl-propoxy=phenyl)acetic acid hydrochloride salt

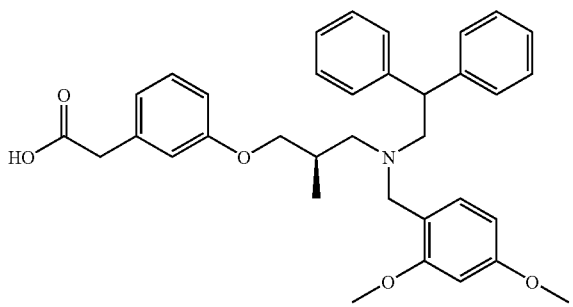

Following the procedure of Example 7(d) except (R)-2-(3-{3-[(2,2-diphenylethyl)amino]2-methyl-propoxy}phenyl) acetic acid and 2,4-dimethoxybenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The resulting amine/carboxylic acid was dissolved in Et₂O (diethylether) and acidified with 1.0 M HCV Et₂O. The reaction mixture was concentrated in vacuo and dried under reduced pressure to give the title compound as a white solid, 85 mg (83%). MS (ESI) 554.6 (M+H⁺).

EXAMPLE 14

(R)-2-(3-{3-[[4-Methoxy-benzyl](2,2-diphenylethyl)amino]-2-methyl-propoxy}-phenyl)acetic acid hydrochloride salt

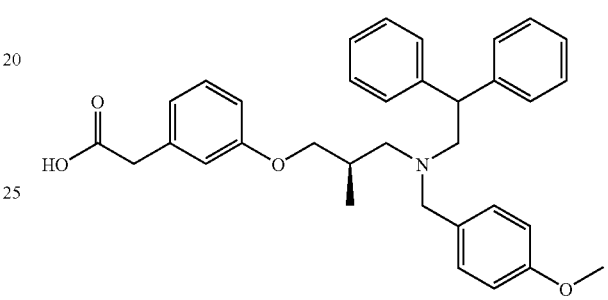

Following the procedure of Example 7(d) except (R)-2-(3-{3-[(2,2-diphenylethyl)amino]2-methyl-propoxy}phenyl) acetic acid and 4-methoxybenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The resulting amine/carboxylic acid was dissolved in Et₂O (diethylether) and acidified with 1.0 M HCl/Et₂O. The reaction mixture was concentrated in vacuo and dried under reduced pressure to give the title compound as a white solid, 94 mg (97%). MS (ESI) 524.4 (M+H⁺).

EXAMPLE 15

(R)-2-(3-{3-[[2-Fluoro-4-methoxy-benzyl](2,2-diphenylethyl)amino]-2-methyl-propoxy}-phenyl)acetic acid hydrochloride salt

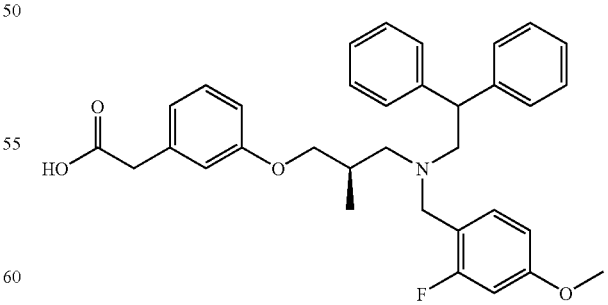

Following the procedure of Example 7(d) except (R)-2-(3-{3-[(2,2-diphenylethyl)amino]2-methyl-propoxy}-phenyl) acetic acid and 2-fluoro-4-methoxybenzaldehyde were used instead of (R)-2-(3-{3-(2,2-diphenylethyl)amino]-3-methyl-propoxy}-phenyl)acetic acid methyl ester and 2-chloro-3- trifluoromethylbenzaldehyde in step (d) the corresponding carboxylic acid was obtained. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 98 mg (98%). MS (ESI) 542.4 (M+H$^+$).

EXAMPLE 16

(R)-2-(3-{3-[[3-Fluoro-4-methoxy-benzyl](2,2-diphenylethyl)amino]-2-methyl-propoxy}-phenyl)acetic acid hydrochloride salt

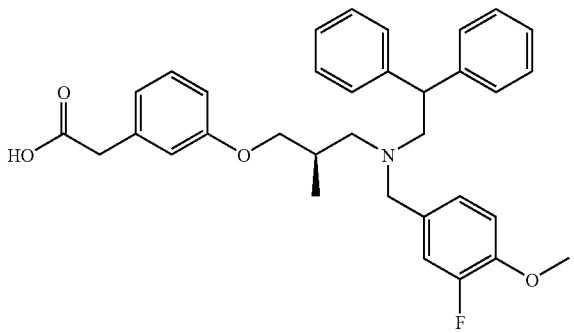

Following the procedure of Example 7(d) except (R)-2-(3-{3-[(2,2-diphenylethyl)amino]2-methyl-propoxy}-phenyl) acetic acid (Example 30-Step (a-b)) and 3-fluoro-4-methoxy-benzaldehyde were used instead of (R)-2-(3-{3-[(2,2-diphenylethyl)amino]-3-methyl-propoxy}phenyl)acetic acid methyl ester and 2-chloro-3-trifluoromethylbenzaldehyde in step (d) the corresponding carboxylic acid was obtained. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 98 mg (97%). MS (ESI) 542.4 (M+H$^+$).

EXAMPLE 17

(R)-2-(3-{3-[[2,4-dimethoxybenzyl](2,2-diphenylethyl)amino]-1-methyl-propoxy}-phenyl)acetic acid hydrochloride salt

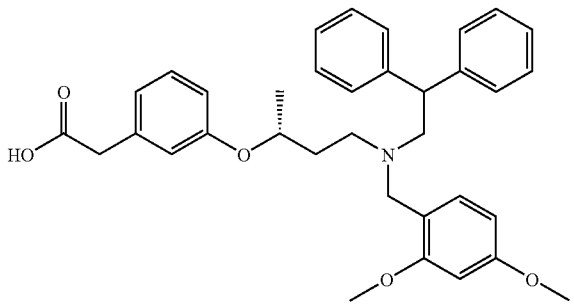

a) (S)-4-[N-(2,2-Diphenylethyl)-amino]-butan-2-ol

To a stirring solution of N-(2,2-diphenylethyl)-amine (1.50 g, 7.61 mmol) and toluene-4-sulfonic acid-(S)-3-hydroxy-butyl ester (1.86 g, 7.61 mmol) [Example 4(a)] in acetonitrile (15 mL) was added solid K$_2$CO$_3$ (3.15 g, 22.84 mmol) and NaI (3.42 g, 22.84 mmol). The reaction mixture was heated to reflux and stirred overnight. The mixture was cooled to RT, filtered, and the filtrate was concentrated. The crude product was purified by preparative HPLC (TMC CombiPrep PDS, 75×30 mm, 25 mL/min, acetonitrile: H$_2$O, UV detection at 254 nm) to give 2.18 g (100% yield) of the title compound as an oil. MS(ESI) 270.2 (M+H$^+$).

b) (R)-2-(3-{3-[(2,2-diphenylethyl)amino]-1-methyl-propoxy}-phenyl)acetic acid methyl ester Following the procedure of Example 2(c) except (S)-4-[N-(2,2-Diphenylethyl)-amino]-butan-2-ol was used instead of (S)-4-[N-(2,2-diphenylethyl)-N-(2-chloro-3-trifluoromethyl)amino]-butan-2-ol in step (c) the title compound was obtained as a white powder, 1.46 g (47%). MS (ESI) 418.4 (M+H$^+$).

c) (R)-2-(3-{3-[(2,2-diphenylethyl)amino]-1-methyl-propoxy}-phenyl)acetic acid

Following the procedure of Example 2 except (R)-2-(3-{3-[(2,2-diphenylethyl)amino]1-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated (as the free base) to give a white solid, 1.4 g (100% yield). MS(ESI) 404.2 (M+H$^+$).

d) (R)-2-(3-{3-[[2,4-dimethoxybenzyl](2,2-diphenylethyl)amino]-1-methyl-propoxy}-phenyl)acetic acid hydrochloride salt Following the procedure of Example 7(d) except (R)-2-(3-{3-[(2,2-diphenylethyl)amino]-1-methyl-propoxy}-phenyl) acetic acid and 2,4-dimethoxybenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The free base was dissolved in Et$_2$O (diethylether) and acidified with 1.0 M HCl/Et$_2$O. The reaction mixture was concentrated in vacuo and dried under reduced pressure to give the title compound as a white solid, 73 mg (71%). MS (ESI) 554.6 (M+H$^+$).

EXAMPLE 18

(R)-2-(3-{3-[[4-Methoxybenzyl](2,2-diphenylethyl)amino]-1-methyl-propoxy}phenyl)acetic acid hydrochloride salt

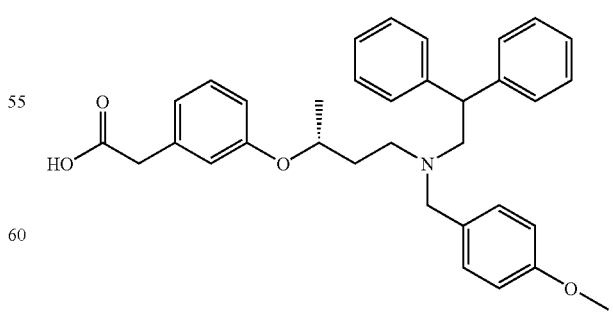

Following the procedure of Example 7(d) except (R)-2-(3-{3-[(2,2-diphenylethyl)amino]-1-methyl-propoxy}-phenyl) acetic acid and 4-methoxybenzaldehyde were used instead of (R)-2-(3-{3-(2,2-diphenylethyl)amino]-3-methyl-propoxy}phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 78 mg (80%). MS (ESI) 524.6 (M+H$^+$).

EXAMPLE 19

(R)-2-(3-{3-[[2-Fluoromethoxybenzyl](2,2-diphenylethyl)amino]-1-methyl-propoxy}phenyl)acetic acid hydrochloride salt

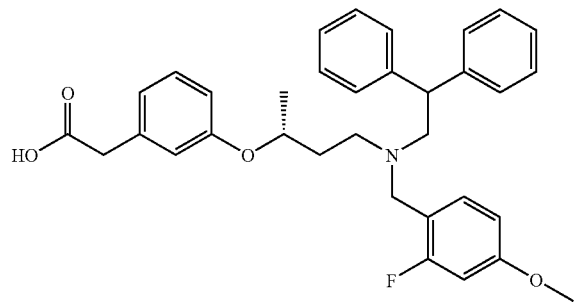

Following the procedure of Example 7(d) except (R)-2-(3-{3-[(2,2-diphenylethyl)amino]-1-methyl-propoxy}phenyl)acetic acid and 2-fluoro-4-methoxybenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 88 mg (87%). MS (ESI) 542.4 (M+H$^+$).

EXAMPLE 20

(R)-2-(3-{3-[[3-trifluoromethylbenzyl](2,2-diphenylethyl)amino]-1-methyl-propoxy}-phenyl)acetic acid hydrochloride salt

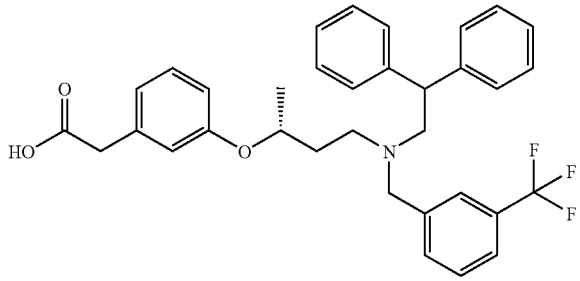

Following the procedure of Example 7(d) except (R)-2-(3-{3-[(2,2-diphenylethyl)amino]-1-methyl-propoxy}-phenyl) acetic acid and 3-trifluoromethylbenzaldehyde were used instead of (R)-2-(3(3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 75 mg (72%). MS (ESI) 562.2 (M+H$^+$).

EXAMPLE 21

(R)-2-(3-{3-[[2-fluoro-3-(trifluoromethyl)benzyl](2,2-diphenylethyl)amino]-1-methyl-propoxy}-phenyl)acetic acid hydrochloride salt

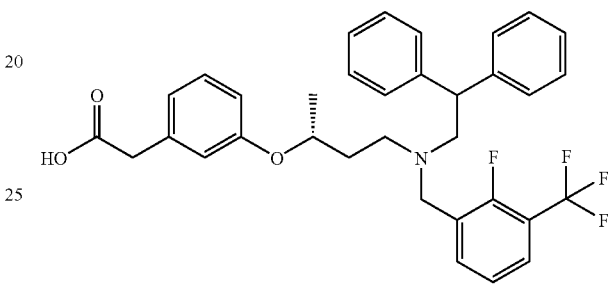

Following the procedure of Example 7(d) except (R)-2-(3-{3-[(2,2-diphenylethyl)amino]-1-methyl-propoxy}-phenyl) acetic acid and 2-fluoro-3-(trifluoromethyl)benzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 90 mg (84%). MS (ESI) 580.6 (M+H$^+$).

EXAMPLE 22

(R)-2-(3-{3-[[3-(trifluoromethyl)-4-fluoro-benzyl](2,2-diphenylethyl)amino]-1-methyl-propoxy}-phenyl) acetic acid hydrochloride salt

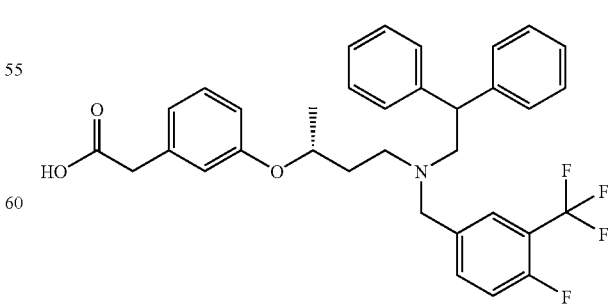

Following the procedure of Example 7(d) except (R)-2-(3-{3-[(2,2-diphenylethyl)amino]-1-methyl-propoxy}-phenyl)

acetic acid and 3-(trifluoromethyl)-4-fluoro-benzaldehyde were used instead of (R)-2-(3-{3-(2,2-diphenylethyl)amino]-3-methyl-propoxy}phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 95 mg (88%). MS (ESI) 580.6 (M+H$^+$).

EXAMPLE 23

(R)-2-(3-{3-[[3-fluoro-4-methoxybenzyl](2,2-diphenylethyl)amino]-1-methyl-propoxy}phenyl)acetic acid hydrochloride salt

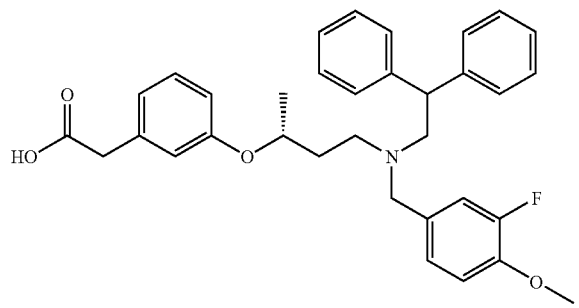

Following the procedure of Example 7(d) except (R)-2-(3-{3-[(2,2-diphenylethyl)amino]-1-methyl-propoxy}-phenyl) acetic acid and 3-fluoro-4-methoxybenzaldehyde were used instead of (R)-2-(3-{3-(2,2-diphenylethyl)amino]-3-methyl-propoxy}-phenyl)acetic acid methyl ester and 2-chloro-3-trifluoromethylbenzaldehyde in step (d) the corresponding carboxylic acid was obtained. The crude product was purified by preparative HPLC (TMC CombiPrep PDS, 75×30 mm, 25 mL/min, acetonitrile: H$_2$O, UV detection at 254 nm) to afford the free base. The resulting amine/carboxylic acid was dissolved in Et$_2$O (diethylether) and acidified with 1.0 M HCl/Et$_2$O. The reaction mixture was concentrated in vacuo and dried under reduced pressure to give the title compound as a white solid, 100 mg (99%). MS (ESI) 542.4 (M+H$^+$).

EXAMPLE 24

(R)-2-(3-{3-[[2-Chlorobenzyl](2,2-diphenylethyl)amino]-3-methyl-propoxy}-phenyl)acetic acid hydrochloride salt

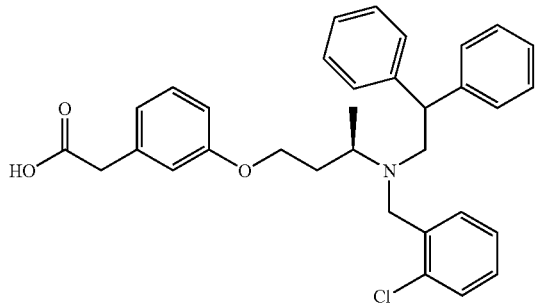

Following the procedure of Example 7(a)-(e) except 2-chlorobenzaldehyde was used instead of 2-chloro-3-trifluoromethylbenzaldehyde in step (d) the corresponding carboxylic acid was obtained as a white solid, 80 mg (11%). MS (ESI) 528.4 (M$^+$).

EXAMPLE 25

(R)-2-(3-{3-[[3-Trifluoromethylbenzyl](2,2-diphenylethyl)amino]-3-methyl-propoxy}-phenyl)acetic acid hydrochloride salt

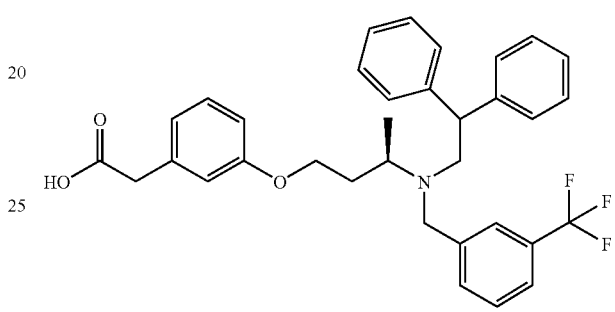

Following the procedure of Example 7(a)-(e) except 3-trifluoromethylbenzaldehyde was used instead of 2-chloro-3-trifluoromethylbenzaldehyde in step (d) the corresponding carboxylic acid was obtained as a white solid, 76 mg (10%). MS (ESI) 562.2 (M+H$^+$).

EXAMPLE 26

(R)-2-(3-{3-[[2-Fluoro-(3-trifluoromethyl)benzyl](2,2-diphenylethyl)amino]-3-methyl-propoxy}-phenyl)acetic acid hydrochloride salt

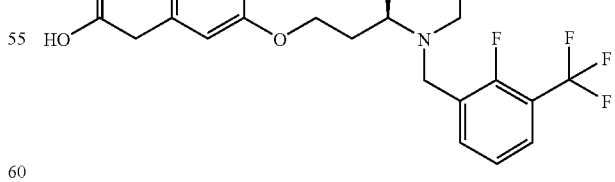

Following the procedure of Example 7(a)-(e) except 2-fluoro-3-trifluoromethylbenzaldehyde was used instead of 2-chloro-3-trifluoromethylbenzaldehyde in step (d) the corresponding carboxylic acid was obtained as a white solid, 82 mg (10%). MS (ESI) 580.4 (M+H$^+$).

EXAMPLE 27

(R)-2-(3-{3-[[3-Trifluoromethyl-4-fluoro-benzyl](2,2-diphenylethyl)amino]-3-methyl-propoxy}-phenyl)acetic acid hydrochloride salt

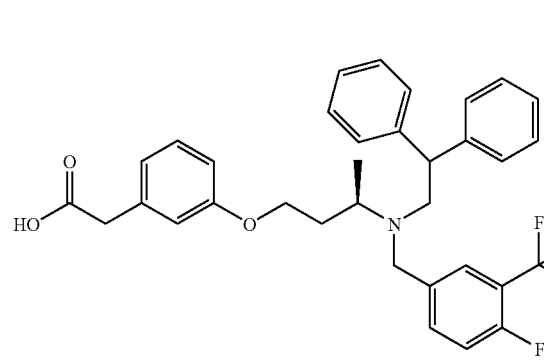

Following the procedure of Example 7(a)-(e) except 3-trifluoromethyl-4-fluoro-benzaldehyde was used instead of 2-chloro-3-trifluoromethylbenzaldehyde in step (d) the corresponding carboxylic acid was obtained as a white solid, 90 mg (12%). MS (ESI) 580.4 (M+H$^+$).

EXAMPLE 28

(R)-2-(3-{3-[[2,4-Dimethoxybenzyl](2,2-diphenylethyl)amino]-3-methyl-propoxy}-phenyl)acetic acid hydrochloride salt

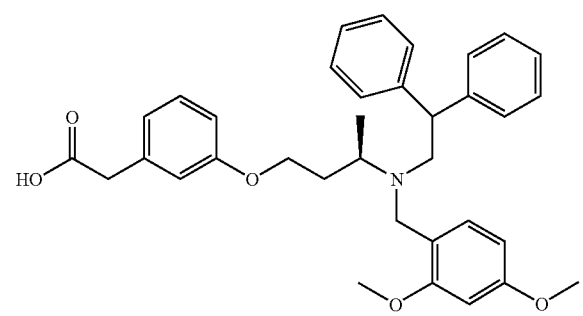

Following the procedure of Example 7(a)-(e) except 2,4-dimethoxybenzaldehyde was used instead of 2-chloro-3-trifluoromethylbenzaldehyde in step 7(d) the corresponding carboxylic acid was obtained as a white solid, 87 mg (11%). MS (ESI) 554.4 (M+H$^+$).

EXAMPLE 29

(R)-2-(3-{3-[[4-Methoxybenzyl](2,2-diphenylethyl)amino]-3-methyl-propoxy}-phenyl)acetic acid hydrochloride salt Following the procedure of Example 7(a)-(e) except 4-Methoxybenzaldehyde was used instead of 2-chloro-3-trifluoromethylbenzaldehyde in step (d) the corresponding carboxylic acid was obtained as a white solid, 76 mg (11%). MS (ESI) 524.4 (M+H$^+$).

EXAMPLE 30

(R)-2-(3-{3-[[2-Fluoro-4-methoxybenzyl](2,2-diphenylethyl)amino]-3-methyl-propoxy}-phenyl)acetic acid hydrochloride salt

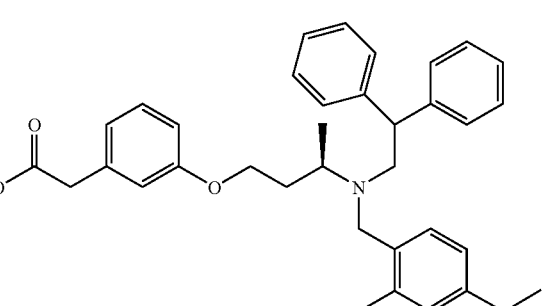

Following the procedure of Example 7(a)-(e) except 2-fluoro-4-methoxybenzaldehyde was used instead of 2-chloro-3-trifluoromethylbenzaldehyde in step (d) the corresponding carboxylic acid was obtained as a white solid, 89 mg (12%). MS (ESI) 542.4 (M+H$^+$).

EXAMPLE 31

(R)-2-(3-{3-[[2-Chloro-3,4-dimethoxybenzyl](2,2-diphenylethyl)amino]-3-methyl-propoxy}-phenyl)acetic acid hydrochloride salt

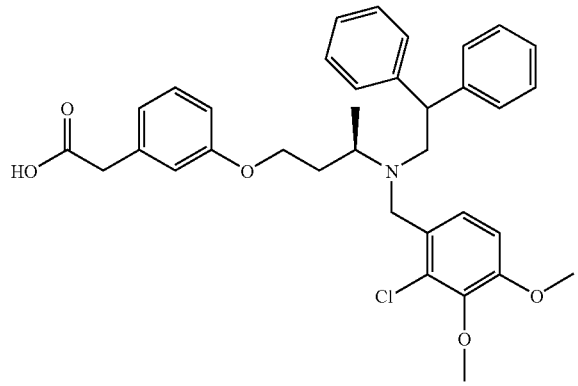

Following the procedure of Example 7(a)-(e) except 2-chloro-3,4-dimethoxybenzaldehyde was used instead of 2-chloro-3-trifluoromethylbenzaldehyde in step (d) the corresponding carboxylic acid was obtained as a white solid, 93 mg (11%). MS (ESI) 588.2 (M+H$^+$).

EXAMPLE 32

(R)-2-(3-{3-[[3-Fluoromethoxybenzyl](2,2-diphenylethyl)amino]-3-methyl-propoxy}-phenyl)acetic acid hydrochloride salt

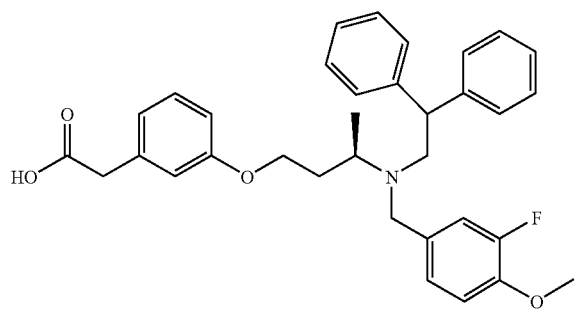

Following the procedure of Example 7(a)-(e) except 3-fluoro-4-methoxybenzaldehyde was used instead of 2-chloro-3-trifluoromethylbenzaldehyde in step (d) the corresponding carboxylic acid was obtained as a white solid, 86 mg (11%). MS (ESI) 542.2 (M+H$^+$).

EXAMPLE 33

(3-{3-[[2,2-(Bis-(4-fluoro-phenyl)-ethyl]-(2-chloro-3-(trifluoromethyl)-benzyl)-amino]-propoxy}-phenyl)-acetic acid hydrochloride salt

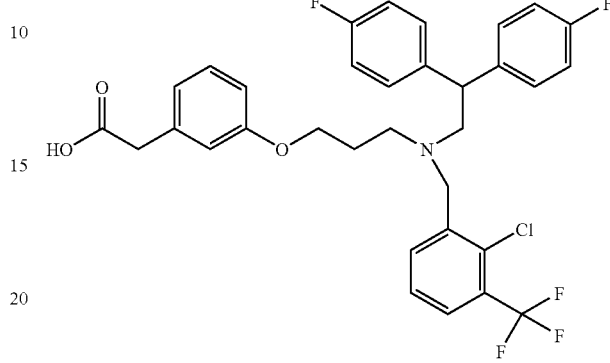

a) 1-Methoxy-2,2-bis(4-fluoro-phenyl)-propene

To a stirring solution of THF (300 mL) at room temperature was added methoxymethyltriphenylphosphonium chloride (16.5 g, 48.1 mmol) and sodium tert-butoxide (4.6 g, 48.1 mmol). The orange-red solution was stirred for 1 h, and then bis(4-fluoro)-benzophenone (7.0 g, 32.1 mmol) was added and the mixture was heated at 60° C. for 3 h. The reaction mixture was cooled to room temperature and filtered through a fritted funnel. The filtrate was concentrated down and dissolved in diethyl ether. The resulting precipitate was filtered off, and the ethereal filtrate was concentrated (this process was repeated until triphenylphosphine oxide stopped precipitating out of ether solution). The crude product was then subjected to flash silica gel chromatograpy (1% Et$_2$O:hexane to 5% Et$_2$O:hexane) to afford the title compound as a white solid, 4.38 g (55%). MS (ESI) 247.0 (M+H$^+$).

b) Bis-(4-fluoro-phenyl)-acetaldehyde

To a stirring solution of 1-methoxy-2,2-bis(4-fluoro-phenyl)-propene (0.22 g, 0.81 mmol) in 2 mL of glacial acetic acid was added perchloric acid (70%, 0.2 mL). After stirring for 1 h at RT, the reaction mixture was diluted with water and extracted with EtOAc. The organic layer was washed with saturated NaHCO$_3$, water, brine, dried over Na$_2$SO$_4$ and concentrated in vacuo to give an oil, 0.18 g (96%). The aldehyde was used in the next step without further purification.

c) [3-(3-t-Butoxycarbonylamino-propoxy)-phenyl]-acetic acid methyl ester

To a stirring mixture of (3-hydroxy-phenyl)-acetic acid methyl ester (1.66 g, 10 mmol), triphenylphosphine (3.15 g, 12 mmol) and THF (30 mL) at 0° C. was added tert-Butyl N-(3-hydroxypropyl)-carbamate (2.05 mL, 12 mmol). Next DIAD (2.36 mL, 12 mmol) was added dropwise over 10 min. After stirring overnight at RT the reaction mixture was concentrated and the residue was purified by normal phase HPLC (10 to 60% EtOAc:hexane). The title compound was obtained as an oil (2.55 g, 79%). MS (ESI): 324.2 (M+H$^+$)

d) [3-(3-Amino-propoxy)-phenyl]-acetic acid methyl ester hydrochloride

To a stirring mixture of [3-(3-t-Butoxycarbonylamino-propoxy)-phenyl]-acetic acid methyl ester (1.35 g, 4.18 mmol) in MeOH (5 mL) was added HCl (5 mL, 4 M solution in dioxane). The mixture was stirred overnight at RT and concentrated. Toluene was added and the solution was evaporated to facilitate H₂O removal via azeotrope evaporation (under reduced pressure). Ether was added and evaporated under (under reduced pressure) to afford the title compound as a white solid (0.75 g, 69%). MS (ESI): 224.2 (M+H⁺)

e) (3-{3-[2,2-Bis-(4-fluoro-phenyl)-ethylamino]-propoxy}-phenyl)-acetic acid methyl ester.

To a stirring solution of [3-(3-Amino-propoxy)-phenyl]-acetic acid methyl ester hydrochloride (0.26 g, 1 mmol), bis-(4-fluoro-phenyl)-acetaldehyde (0.255 g, 1.1 mmol) in 10 mL of MeOH were added glacial acetic acid (0.3 mL), sodium acetate (0.087 g, 1.0 mmol) and sodium cyanoborohydride (0.070 g, 1.11 mmol). After stirring for 2 h at RT, the reaction mixture was concentrated.

The resulting residue was partitioned between EtOAc and saturated NaHCO₃ and extracted. The organic layer was washed with water, brine, dried over MgSO₄, and filtered. After concentration of the filtrate in vacuo, the crude product was purified by column chromatography over silica gel (silica gel 60, EM Science) using 1% MeOH-0.5% conc. NH₄OH-dichloromethane to give 0.185 g of an oil (42%). MS (ESI): 440.2 (M+H⁺).

f) (3-{3-[[2,2-(Bis-(4-fluoro-phenyl)-ethyl]-(2-chloro-3-trifluoromethyl-benzyl)-amino]propoxy}-phenyl)-acetic acid methyl ester Following the procedure of Example 7 (d), except (3-{3-[2,2-bis-(4-fluoro-phenyl)-ethylamino]-propoxy}-phenyl)-acetic acid methyl ester was used instead of (R)-2-(3-{3-(2,2-diphenylethyl)amino]-3-methyl-propoxy}-phenyl)acetic acid methyl ester in step (d) the title compound was prepared as a white solid (55%). MS (ESI) 632.4 (M+H⁺).

g) (3-{3-[[2,2-(Bis-(4-fluoro-phenyl)-ethyl]-(2-chloro-3-trifluoromethyl-benzyl)-amino]-propoxy}-phenyl)-acetic acid hydrochloride Following the procedure of Example 2 except (3-{3-[[2,2-(Bis-(4-fluoro-phenyl)-ethyl]-(2-chloro-3-trifluoromethyl-benzyl)-amino]-propoxy}-phenyl)-acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester the title compound was prepared as a white solid (89%). MS (ESI) 618.0 (M+H⁺).

EXAMPLE 34

(3-{3-[[2,2-(Bis-(3-fluoro-phenyl)-ethyl]-(2-chloro-3-(trifluoromethyl)-benzyl)-amino]-propoxy}-phenyl)-acetic acid hydrochloride salt

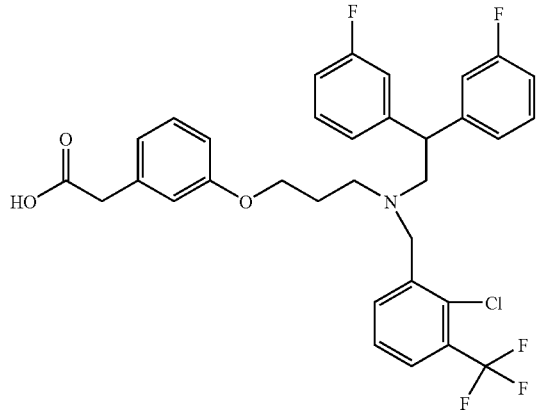

a) (3-{3-[2,2-Bis-(3-fluoro-phenyl)-ethylamino]-propoxy}-phenyl)-acetic acid methyl ester.

Following the procedure of Example 33 (a-e) above, except bis(3-fluoro)-benzophenone was used in step (a) instead of bis(4-fluoro)-benzophenone the title compound was prepared as a white solid (23%). MS (ESI) 440.4 (M+H⁺).

b) (3-{3-[[2,2-(Bis-(3-fluoro-phenyl)-ethyl]-(2-chloro-3-trifluoromethyl-benzyl)-amino]-propoxy}-phenyl)-acetic acid methyl ester Following the procedure of Example 7(d), except (3-{3-[2,2-Bis-(3-fluoro-phenyl)-ethylamino]-propoxy}-phenyl)-acetic acid methyl ester was used instead of (R)-2-(3-{3-(2,2-diphenylethyl)amino]-3-methyl-propoxy}-phenyl)acetic acid methyl ester in step (d) the title compound was prepared as a white solid (35%). MS (ESI) 632.2 (M+H⁺).

c) (3-{3-[[2,2-(Bis-(4-fluoro-phenyl)-ethyl]-(2-chloro-3-trifluoromethyl-benzyl)-amino]-propoxy}-phenyl)-acetic acid hydrochloride Following the procedure of Example 2 except (3-{3-[[2,2-(Bis-(4-fluoro-phenyl)-ethyl]-(2-chloro-3-trifluoromethyl-benzyl)-amino]-propoxy}-phenyl)-acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester the title compound was prepared as a white solid (78%). MS (ESI) 618.2 (M+H⁺).

EXAMPLE 35 rac-(3-{3-[[2-Phenyl-2-(o-chloro-phenyl)-ethyl]-(2-chloro-3-(trifluoromethyl)-benzyl)-amino]-propoxy}-phenyl)-acetic acid hydrochloride salt

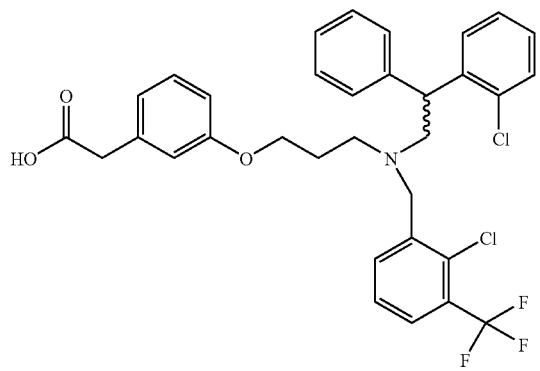

a) rac-(3-{3-[2-phenyl-2-(o-chloro-phenyl)-ethylamino]-propoxy}-phenyl)-acetic acid methyl ester.

Following the procedure of Example 33 (a-e) above, except (2-chloro-phenyl)-2-phenyl-acetaldehyde was used in step (a) instead of bis(4-fluoro)-benzophenone the title compound was prepared as a white solid (23%). MS (ESI) 438.2 (M+H⁺).

b) (3-{3-[[2-phenyl-2-(o-chloro-phenyl)-ethyl]-(2-chloro-3-(trifluoromethyl)-benzyl)-amino]-propoxy}-phenyl)-acetic acid methyl ester Following the procedure of Example 7(d), except rac-(3-{3-[2-phenyl-2-(o-chloro-phenyl)-ethylamino]-propoxy}-phenyl)-acetic acid methyl ester was used instead of (R)-2-(3-{3-(2,2-diphenylethyl)amino]-3-methyl-propoxy}-phenyl)acetic acid methyl ester in step (d) the title compound was prepared as a white solid (40%). MS (ESI) 630.2 (M+H⁺).

c) (3-{3-[[2-phenyl-2-(o-chloro-phenyl)-ethyl]-(2-chloro-3-(trifluoromethyl)-benzyl)-amino]-propoxy}-phenyl)-acetic acid hydrochloride Following the procedure of Example 2 except (3-{3-[[2-phenyl-2-(o-chloro-phenyl)-ethyl]-(2-chloro-3-(trifluoromethyl)-benzyl)-amino]-propoxy}-phenyl)-acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester the title compound was prepared as a white solid (87%). MS (ESI) 616.0 (M+H$^+$).

EXAMPLE 36

Preparation of 2-(3-{3-[(2-Chloro-3-trifluoromethyl-benzyl)-2,2-diphenylethyl-amino]-propoxy}-phenyl)-butyric acid hydrochloride salt

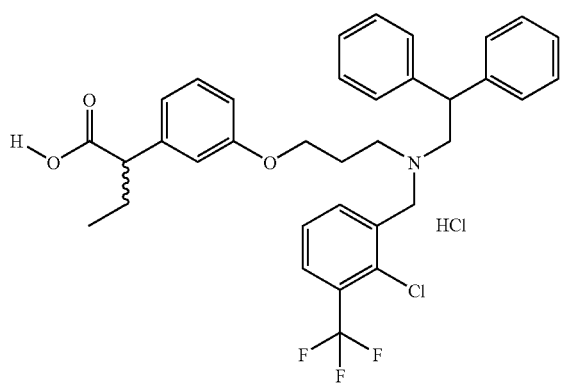

a) 2-(3-{3-[(2-Chloro-3-trifluoromethyl-benzyl)-2,2-diphenylethyl-amino]-propoxy}-phenyl)-butyric acid To a solution of (3-{3-[(2-chloro-3-trifluoromethyl-benzyl)-2,2-diphenylethyl-amino]-propoxy}-phenyl)-acetic acid (70 mg, 0.12 mmol) in dry THF (50 mL) was added lithium diisopropylamide (0.17 mL, 0.35 mmol) dropwise with cooling to −78° C. After the reaction mixture was stirred at −78° C. for an additional 1 h, iodoethane (40 μl) was added. The reaction was warmed to RT over 4 h followed by quenching with saturated ammonium chloride (10 mL). Solvent was removed and the residue was partitioned between water and ethyl acetate. The combined organic layers were washed with brine, dried over sodium sulfate, and concentrated under vacuum. The residue was purified by silica gel column chromatograph (EtOAc:Hexane/20:80) to give the title compound as an oil (37 mg, 50%). MS m/e 609.2 (M+H)$^+$.

b) 2-(3-{3-[(2-Chloro-3-trifluoromethyl-benzyl)-2,2-diphenylethyl-amino]-propoxy}-phenyl)-hexanoic acid hydrochloride salt To a solution of 2-(3-{3-[(2-Chloro-3-trifluoromethyl-benzyl)-2,2-diphenylethyl-amino]-propoxy}-phenyl)-hexanoic acid in diethyl ether was added HCl in diethyl ether (1.0 M) to precipitate the amine salt. The suspension was filtered and dried to give the title compound as a white solid (30 mg, 80%). MS m/e 609.2 (M+H)$^+$.

EXAMPLE 37

2-(3-{3-[(2-Chloro-3-trifluoromethyl-benzyl)-2,2-diphenylethyl-amino]-propoxy}-phenyl)-pentanoic acid hydrochloride salt

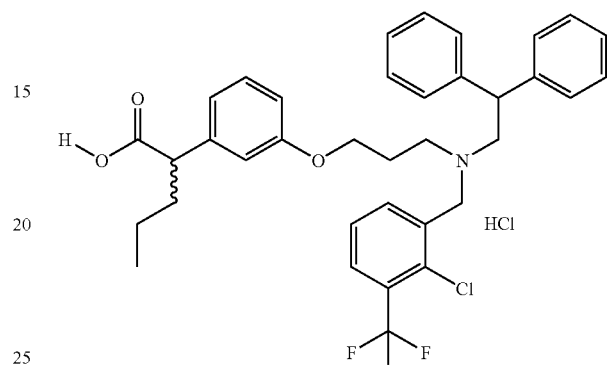

Following the procedure of Example 36 (part a and b) except substituting iodopropane for iodoethane, the title compound was obtained as a white solid (20 mg, 13%). MS (ESI): 625.2 (M+H)$^+$

EXAMPLE 38

2-(3-{3-[(2-Chloro-3-trifluoromethyl-benzyl)-2,2-diphenylethyl-amino]-propoxy}-phenyl)-hexanoic acid hydrochloride salt

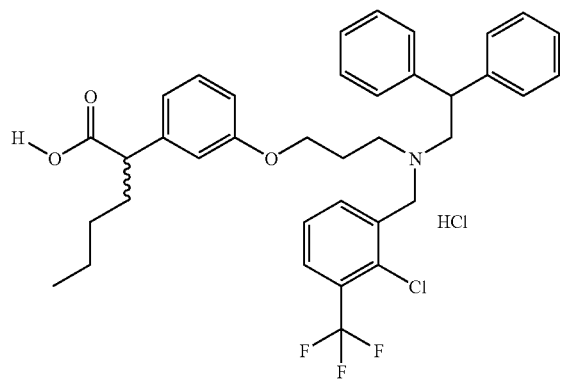

Following the procedure of Example 36 (part a and b) except substituting iodobutane for iodoethane, the title compound was obtained as a white solid (25 mg, 33%). MS (ESI): 638.2 (M+H)$^+$

EXAMPLE 39

2-(3-{3-[(2-Chloro-3-trifluoromethyl-benzyl)-2,2-diphenylethyl-amino]-propoxy}-phenyl)-4-methyl-pentanoic acid hydrochloride salt

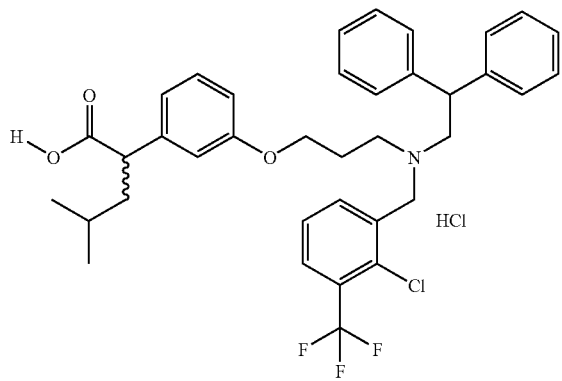

Following the procedure of Example 36 (part a and b) except substituting 1-iodo-2-methyl-propane for iodoethane, the title compound was obtained as a white solid (15 mg, 25%). MS (ESI): 638.2 (M+H)$^+$

EXAMPLE 40

2-(3-{3-[(2-Chloro-3-trifluoromethyl-benzyl)-2,2-diphenylethyl-amino]-propoxy}-phenyl)-2-ethyl-butyric acid methyl ester

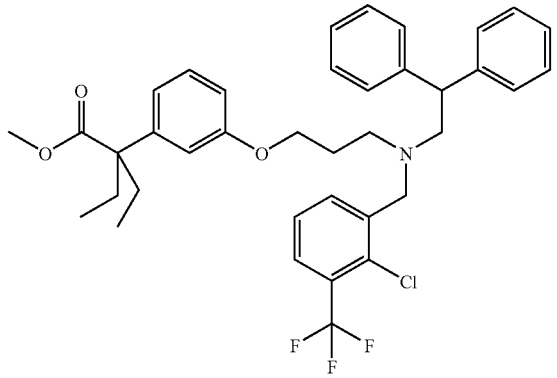

a) (3-{3-[(2-Chloro-3-trifluoromethyl-benzyl)-2,2-diphenylethyl-amino]-propoxy}phenyl)-acetic acid methyl ester To a solution of (3-{3-[(2-Chloro-3-trifluoromethyl-benzyl)-2,2-diphenylethyl-amino]-propoxy}-phenyl)-acetic acid (0.5 g, 3.7 mmol) in methanol (300 mL) was added concentrated HCl (10 mL). After the resulting mixture was heated to reflux for 2 h solvent was removed under vacuum. The residue was dissolved in water and neutralized to pH=7. The aqueous layer was extracted with ethyl acetate. The combined organic layers were washed with saturated sodium bicarbonate, brine, dried over sodium sulfate, and concentrated to give the title compound as colorless oil (0.5 g, 90%). MS m/e 596.6 (M+H)$^+$.

b) 2-(3-{3-[(2-Chloro-3-trifluoromethyl-benzyl)-2,2-diphenylethyl-amino]-propoxy}-phenyl)-2-ethyl-butyric acid methyl ester To a solution of (3-{3-[(2-Chloro-3-trifluoromethyl-benzyl)-2,2-diphenylethyl-amino]-propoxy}-phenyl)-acetic acid methyl ester (70 mg, 0.12 mmol) in dry THF (50 mL) was added lithium diisopropylamide (1.7 mL, 1.2 mmol) dropwise with cooling to −78° C. After the reaction mixture was stirred at −78° C. for an additional 1 h, iodoethane (0.4 mL) was added. The reaction was warmed to RT over 4 h followed by quenching with saturated ammonium chloride (10 mL). Solvent was removed and the residue was partitioned between water and ethyl acetate. The combined organic layers were washed with brine, dried over sodium sulfate, and concentrated. The residue was purified by silica gel column chromatograph (EtOAc:Hexane/20:80) to give the title compound as an oil (37 mg, 50%). MS m/e 652.2 (M+H)$^+$.

EXAMPLE 41

2-(3-{3-[(2-Chloro-3-trifluoromethyl-benzyl)-2,2-diphenylethyl-amino]-propoxy}-phenyl)-2-ethyl-butyric acid hydrochloride salt

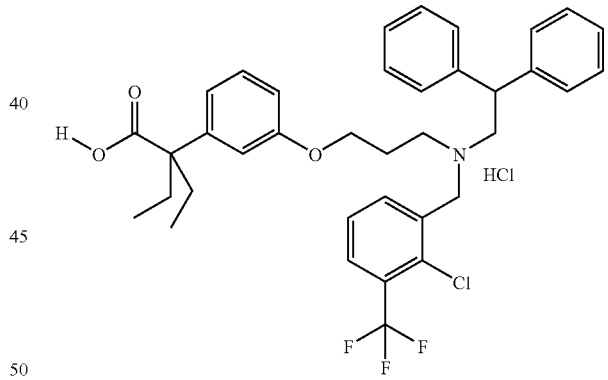

A solution of 2-(3-{3-[(2-chloro-3-trifluoromethyl-benzyl)-2,2-diphenylethyl-amino]-propoxy}-phenyl)-2-ethyl-butyric acid methyl ester (30 mg, 0.05 mmol) in DMF (9 mL) was treated with LiCl (20 mg, 0.46 mmol). The resulting reaction mixture was heated to reflux overnight and concentrated. The crude product was purified by HPLC (YMC CombiPrep ODS-A, 50×20 mm, 20 mL/min, A:acetonitrile B:water, A: 60 to 100% during 10 min, UV detection at 254 nm) to give the title compound, the free amine as an oil (15 mg, 45%). To a solution of the free amine in diethyl ether was added HCl in diethyl ether (1.0 M) to precipitate the amine salt. The suspension was filtered and dried to give the title compound as a white solid. MS m/e 638.2 (M+H)$^+$.

EXAMPLE 42

2-(3-{(R)-3-[(2-Chloro-3-trifluoromethyl-benzyl)-2,2-diphenylethyl-amino]-butoxy}-phenyl)-2-methyl-propionic acid

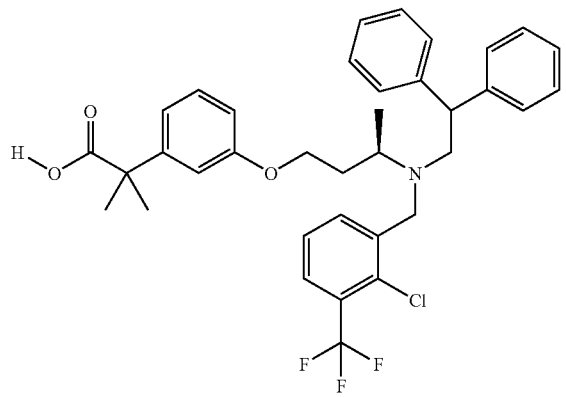

Following the procedure of Example 40 and 41 except using (3-{(R)-3-[(2-chloro-3-trifluoromethyl-benzyl)-2,2-diphenylethyl-amino]-butoxy}-phenyl)-acetic acid as the starting material, the title compound was obtained as a free amine oil (20 mg, 15%). MS (ESI): 637.2 (M+H)+.

EXAMPLE 43

3-{3-[(2-Chloro-3-trifluoromethyl-benzyl)-2,2-diphenylethyl-amino]-propoxy}-benzoic acid methyl ester hydrochloride salt

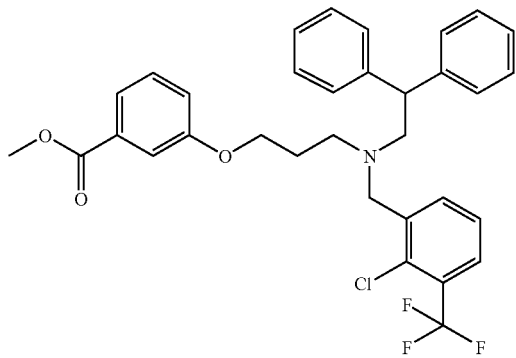

To a solution of 3-[(2-chloro-3-trifluoromethyl-benzyl)-2,2-diphenylethyl-amino]-propan-1-ol (0.60 g, 1.34 mmol) in toluene (4 mL) at RT was added 3-hydroxy-benzoic acid methyl ester (0.22 g, 1.45 mmol). The mixture was treated with polymer bound triphenylphosphine (0.82 g, 2.50 mmol, 3 mmol/g, Fluka Chemie) (0.71 g, 2.14 mmol, 3 mmol/g, Fluka Chemie). After 15 minutes of stirring, the mixture was treated with DIAD (0.33 mL, 1.67 mmol) and was stirred overnight at RT. The reaction mixture was filtered, concentrated and purified via preparative HPLC (TMC CombiPrep PDS, 75×30 mm, 25 mL/min, acetonitrile:H₂O, UV detection at 254 nm) to yield the title compound (0.25 g, 32%); MS (ES+) m/e 583 [M+H]+.

EXAMPLE 44

3-{3-[(2-Chloro-3-trifluoromethyl-benzyl)-2,2-diphenylethyl-amino]-propoxy}-benzoic acid hydrochloride salt

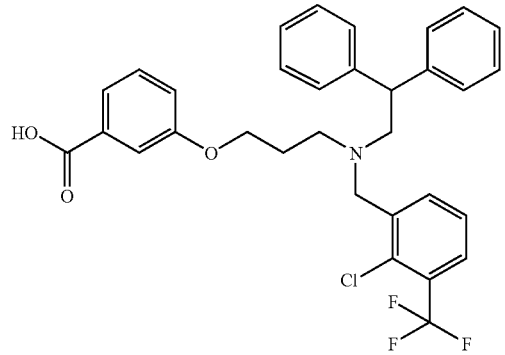

To a solution of 3-{3-[(2-chloro-3-trifluoromethyl-benzyl)-2,2-diphenylethyl-amino]-propoxy}-benzoic acid methyl ester (0.200 g, 0.344 mmol) in THF (7.5 mL) and H₂O (2.5 mL) at RT LiOH.H₂O (0.029 g, 0.688 mmol) was added. The mixture was stirred overnight at RT. The mixture was then treated with more LiOH.H₂O (0.058 g, 1.376 mmol) and heated at 50° C. overnight. The completed reaction was cooled to 0° C. and was quenched with a minimal amount of H₂O. The mixture was the acidified to a pH=2 with concentrated HCl. The mixture was then extracted three times with EtOAc and was dried, filtered and concentrated to afford a foam that was purified via preparative HPLC (TMC CombiPrep PDS, 75×30 mm, 25 mL/min, acetonitrile:H₂O, UV detection at 254 nm) to yield the title compound (0.14 g, 72%); MS (ES+) m/e 569 [M+H]+.

EXAMPLE 45

2-Bromo-5-{3-[(2-chloro-3-trifluoromethyl-benzyl)-2,2-diphenylethyl-amino]-propoxy}-benzoic acid hydrochloride salt

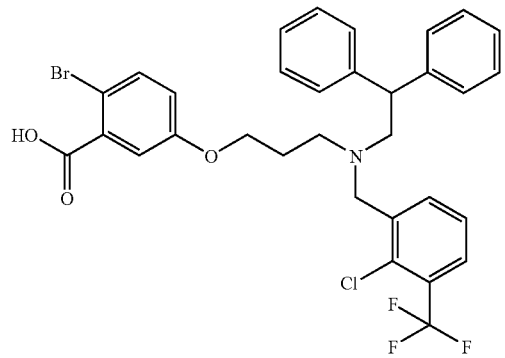

a) 2-Bromo-5-hydroxy-benzoic acid methyl ester

To a solution of 2-bromo-5-methoxy-benzoic acid methyl ester (2.0 g, 8.2 mmol) in dichloromethane (80 mL) at −78° C. under Argon, was added BBr₃ (18 mL, 18.0 mmol) slowly with stirring. After stirring overnight, the reaction was not complete, so an additional BBr₃ (1.5 eq.) was added and the reaction was stirred overnight. The reaction mixture was then cooled to 0° C., MeOH and NaHCO$_3$ was added. The layers were separated. The organic layer was dried over MgSO$_4$, filtered, and concentrated. The oil was purified via normal-phase HPLC (1% MeOH/CH$_2$Cl$_2$) to yield the title compound (1.096 g, 58%); MS (ES+) m/e 232 [M+H]$^+$.

b) 2-Bromo-5-{3-[(chloro-trifluoromethyl-benzyl)-diphenylethyl-amino]-propoxy}-benzoic acid methyl ester Following the procedure of Example 43 except 2-bromo-5-hydroxy-benzoic acid methyl ester for added 3-hydroxy-benzoic acid methyl ester, the title compound was obtained as a clear oil (66%). MS(ES+) m/e 662 [M+H]$^+$ c) 2-Bromo-5-{3-[(2-chloro-3-trifluoromethyl-benzyl)-2,2-diphenylethyl-amino]-propoxy}-benzoic acid To a solution of 2-bromo-5-{3-[(2-chloro-3-trifluoromethyl-benzyl)-2,2-diphenylethyl-amino]-propoxy}-benzoic acid methyl ester (0.30 g, 0.45 mmol) in a 1:1 solution of THF:H$_2$O, 1N solution of LiOH in H$_2$O (1.2 eq.) was added and the mixture was stirred overnight at RT. Then, LiOH.H$_2$O (5 eq.) and KOH (5 eq.) was added and the reaction mixture was stirred over the weekend. Followed the same workup and purification procedures as Example 44. MS(ES+) m/e 648 [M+H]$^+$

EXAMPLE 46

(2-Bromo-5-{3-[(2-chloro-3-trifluoromethyl-benzyl)-2,2-diphenylethyl-amino]-propoxy}-phenyl)-acetic acid hydrochloride salt

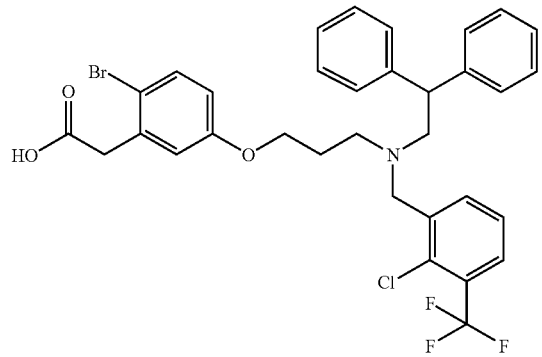

a) (2-Bromo-5-{3-[(2-chloro-3-trifluoromethyl-benzyl)-2,2-diphenylethyl-amino]-propoxy}-phenyl)-acetic acid methyl ester To a solution of 2-bromo-5-{3-[(chloro-trifluoromethyl-benzyl)-diphenylethyl-amino]-propoxy}-benzoic acid (0.20 g, 0.351 mmol) in toluene (2 mL) at ambient temperature under Argon, SOCl$_2$ (0.046 mL, 0.631 mmol) was added. The reaction mixture was heated at 95° C. for 3 h and purged with Argon. TMSCHN$_2$ (0.946 mL, 0.946 mmol) was added and the mixture stirred until the bubbling ceased. The reaction mixture was concentrated, dissolved in MeOH (2 mL), and silver benzoate (cat. amt.) was added. After the reaction mixture was heated to 50° C. for 0.5 h, the mixture was filtered, concentrated, and purified via preparative HPLC (TMC CombiPrep PDS, 75x30 mm, 25 mL/min, acetonitrile:H$_2$O, UV detection at 254 nm) to yield the title compound (0.109 g, 51%). MS (ES+) m/e 676 [M+H]$^+$.

b) (2-Bromo-5-{3-[(2-chloro-3-trifluoromethyl-benzyl)-2,2-diphenylethyl-amino]-propoxy}-phenyl)-acetic acid (2-bromo-5-{3-[(2-chloro-3-trifluoromethyl-benzyl)-2,2-diphenylethyl-amino]-propoxy}-phenyl)-acetic acid methyl ester (0.096 g, 0.161 mmol) was dissolved in a 1:1 solution of THF:1N solution of LiOH in H$_2$O (8 mL) and the mixture was stirred overnight at RT. To the mixture, KOH (5 eq.) was added and the reaction was heated at 50° C. over 48 h. Followed the same workup and purification procedures as Example 44. MS (ES+) m/e 662 [M+H]$^+$

EXAMPLE 47

N-(2-Phenyl-2-cyclopentylethyl)-N-(2-chloro-3-trifluoromethylbenzyl)-3-(3-carboxymethylenephenoxy)propylamine

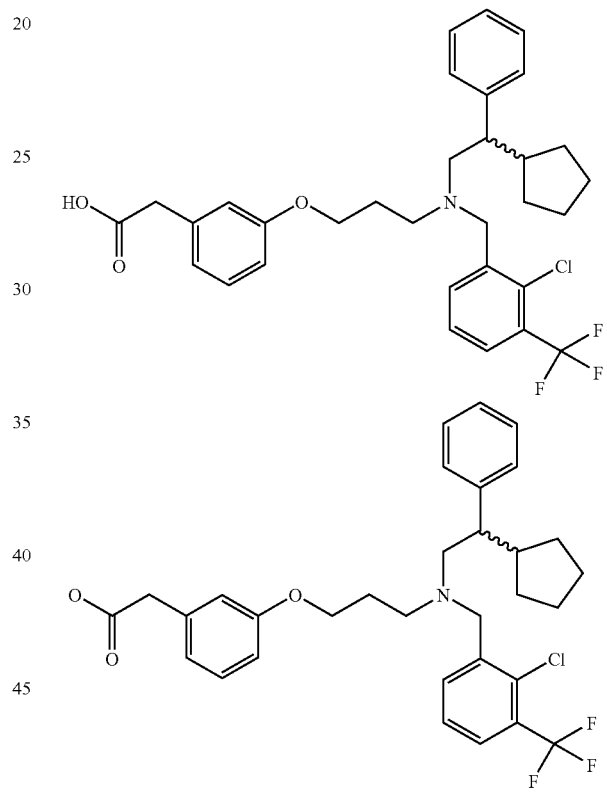

a) Methyl 3-(3-chloropropyloxy)-phenyl acetate

A solution of methyl 3-hydroxyphenylacetate (2.55 g, 15.4 mmol) and 3-chloro-1-propanol (1.45 g, 15.4 mmol) in THF (25 mL) was treated with Ph$_3$P (4.04 g, 15.4 mmol) and diisopropylazodicarboxylate (3.42 g, 16.9 mmol), and the mixture was stirred for 18 h. The reaction was diluted with H$_2$O and extracted with Et$_2$O. The extracts were washed with 0.1N NaOH, 0.1N HCl, and H$_2$O. The extracts were dried and the solvent was removed. Purification via silica gel column chromatography with 10% EtOAc:hexane yielded the titled compound (1.94 g, 52%). MS (ESI) 243 (M+H$^+$).

b) Methyl 3-(3-iodopropyloxy)-phenyl acetate

A solution of methyl 3-(3-chloropropyloxy)-phenyl acetate (1.92 g, 7.9 mmol) in acetone (50 mL) was treated with NaI (3.6 g, 24 mmol), and the mixture was refluxed for 24 h. The reaction was diluted with H$_2$O and extracted with Et$_2$O. The extracts were washed with H$_2$O, aqueous NaHSO$_3$, dried, and concentrated to afford the title compound (2.48 g, 94%). MS (ESI) 335 (M+H⁺).

c) 2-Cyclopentylphenylacetic acid amide

A solution of 2-cyclopentylphenylacetic acid (2.3 g, 11.3 mmol) and benzene (25 mL) containing 1 drop of DMF was treated with oxalyl chloride (2.0 mL), heated to 50° C. for 2 h, cooled, and concentrated. The residue was dissolved in acetone (8 mL) and slowly added to a stirred mixture of 28% NH₄OH (10 mL) and acetone (10 mL) at 0° C. The mixture was stirred for 1 h, the precipitated solid was filtered, washed with water, dried, and concentrated to yield the titled compound (1.93 g, 84%). MS (ESI) 204 (M+H⁺).

d) 2-Cyclopentylphenethylamine

A solution of 2-cyclopentylphenylacetic acid amide (1.28 g, 6.3 mmol) in THF (10 mL) was treated with 1N BH₃ (25 mL) (in THF) and the solution was refluxed for 8 h. The reaction was cooled, 6 N HCl (20 mL) was added, and the mixture was refluxed for 2 h. The mixture was cooled, diluted with H₂O, and washed with Et₂O. The aqueous layer was basified and extracted with Et₂O. The extracts were washed with water, dried, and concentrated to give the titled compound (0.44 g, 35%). MS (ESI) 190 (M+H⁺).

e) N-(2-Phenyl-2-cyclopentylethyl)-2-chloro-3-trifluoromethylbenzylamine.

A solution of 2-cyclopentylphenethylamine (202 mg, 1.07 mmol) and 2-chloro-3-trifluoromethylbenzaldehyde (222 mg, 1.07 mmol) in 10 mL of MeOH was treated with a crystal of p-toluenesulfonic acid and stirred for 1 hour. The reaction was diluted with water, basified with NaHCO₃, and extracted with Et₂O. The extracts were washed with H₂O, dried, and concentrated. The residue was dissolved in 10 mL of MeOH and treated with an excess of NaBH₄. After 1 h, the reaction was diluted with H₂O and extracted with Et₂O. The extracts were washed with H₂O, dried, and concentrated to yield the titled compound (355 mg, 87%). MS (ESI) 382 (M+H⁺).

f) N-(2-Phenyl-2-cyclopentylethyl)-N-(2-chloro-3-trifluoromethylbenzyl)-3-(3-carbomethoxymethylenephenoxy) propylamine A solution of N-(2-Phenyl-2-cyclopentylethyl)-2-chloro-3-trifluoromethylbenzylamine (218 mg, 0.57 mmol), methyl 3-(3-iodopropyloxy)-phenyl acetate (181 mg, 0.54 mmol), and MeCN (6 mL) was treated with K₂CO₃ (75 mg, 0.54 mmol), and the mixture was refluxed for 12 h. The reaction was diluted with H₂O and extracted with Et₂O. The extracts were washed with H₂O, dried, and the solvent evaporated. The residue was purified via silica gel column chromatography eluted with 10% EtOAc:hexane to give the titled compound (159 mg, 50%). MS (ESI) 588 (M+H⁺).

g) N-(2-Phenyl-2-cyclopentylethyl)-N-(2-chloro-3-trifluoromethylbenzyl)-3-(3-carboxymethylenephenoxy)propylamine A solution of N-(2-phenyl-2-cyclopentylethyl)-N-(2-chloro-3-trifluoromethylbenzyl)-3-(3-carbomethoxymethylenephenoxy)propylamine (159 mg, 0.27 mmol) in MeOH (5 mL), THF (1 mL), H₂O (1 mL), and 2.5 N NaOH (2.5 mL) was heated to 50° C. for 1 h. The reaction was cooled, diluted with H₂O, acidified to pH=5.5, and extracted with EtOAc. The extracts were washed with H₂O, dried, and concentrated to yield the titled compound (93 mg, 70%). MS (ESI) 575 (M+H⁺).

EXAMPLE 48

N-(2,2-Diphenylethyl)-N-(2-chloro-3-trifluoromethylbenzyl)-3-(3-carboxyphenoxy)propylamine hydrochloride salt

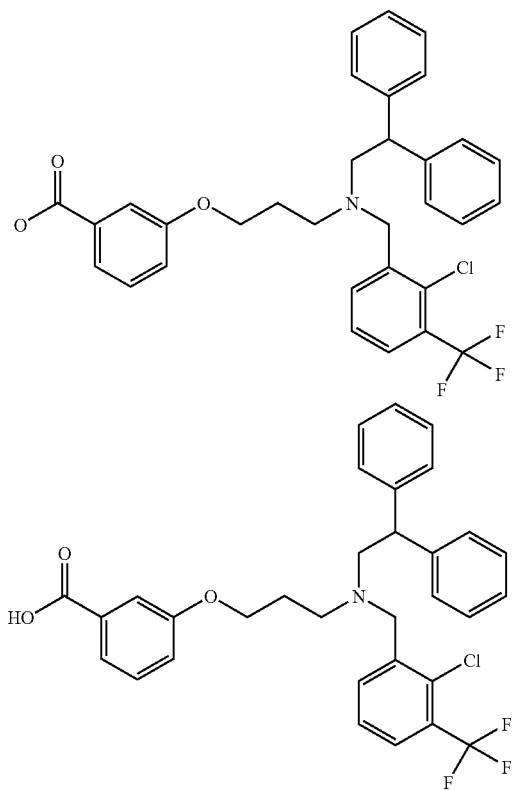

a) N-(2,2-Diphenylethyl)-N-(2-chloro-3-trifluoromethylbenzyl)-3-(3-carbomethoxyphenoxy)propylamine A solution of N-(2,2-diphenylethyl)-N-(2-chloro-3-trifluoromethylbenzyl)-3-hydroxypropylamine (186 mg, 0.42 mmol) and methyl 3-hydroxybenzoate (63 mg, 0.42 mmol) in 15 mL of THF was treated with Ph₃P (110 mg, 0.42 mmol) and diisopropylazodicarboxylate (93 mg, 0.46 mmol). The reaction was stirred for 18 h, diluted with H₂O, and extracted with Et₂O. The extracts were washed with H₂O, dried, and the solvent evaporated. The residue was purified via silica gel column chromatography eluted with 10% EtOAc:hexane to yield the titled product, (64 mg, 26%). MS (ESI) 583 (M+H⁺).

b) N-(2,2-Diphenylethyl)-N-(2-chloro-3-trifluoromethylbenzyl)-3-(3-carboxyphenoxy)propylamine, hydrochloride A solution of N-(2,2-diphenylethyl)-N-(2-chloro-3-trifluoromethylbenzyl)-3-(3-carbomethoxyphenoxy)propylamine (65 mg, 0.11 mmol) in MeOH (5 mL), H₂O (1 mL), and 2.5N NaOH (0.5 mL) was heated at 50° C. for 3 h. The reaction was cooled, diluted with H₂O, acidified with 3N HCl to pH=4, and extracted with EtOAc. The extracts were dried and the solvent removed. The residue was dissolved in Et₂O and treated with 4N HCl in dioxane. The precipatated solid was filtered, washed with Et₂O, dried, and concentrated to yield the titled compound (27 mg, 42%). MS (ESI) 569 (M+H⁺).

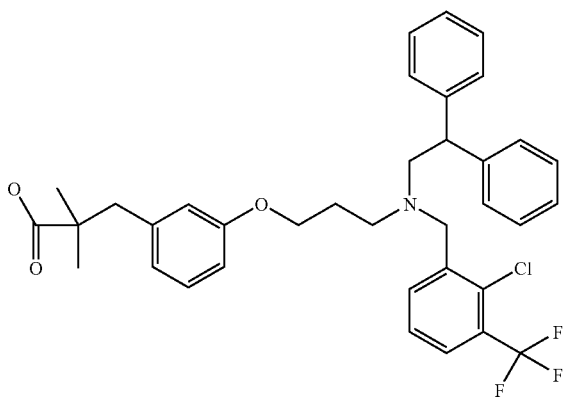

EXAMPLE 49

N-(2,2-Diphenylethyl)-N-(2-chloro-3-trifluoromethylbenzyl)-2,2-dimethyl-3-(3-aminopropoxy)phenylpropionic acid

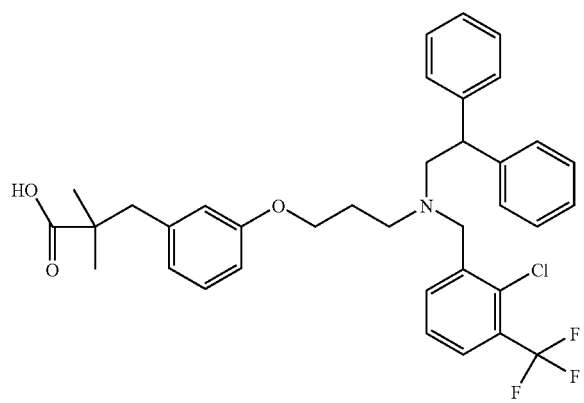

a) 2,2-Dimethyl-3-(3-benzyloxyphenyl)propionic acid

A solution of diisopropylamine (1.55 mL, 11.9 mmol) and THF (20 mL) was cooled to −78° C. and treated with n-BuLi (6.5 mL, 10.4 mmol) (1.6 M in hexane). After 10 minutes, a solution of isobutyric acid (436 mg, 4.96 mmol) in THF (3 mL) followed by HMPA (1.74 mL, 10 mmol) was added to the reaction mixture. The reaction was warmed to 23° C., then heated at 55° C. for 0.5 h. The reaction was cooled to −78° C. and a solution of 3-benzyloxybenzyl chloride (1.15 g, 4.96 mmol) in THF (6 mL) was added. The reaction was warmed to 23° C. for 30 minutes and then heated at 55° C. for 30 minutes. The reaction was cooled, diluted with $H_2O$, acidified with 3N HCl, and extracted with $Et_2O$. The extracts were washed with $H_2O$ (3×), dried, and concentrated to yield the titled compound as a white powder (1.2 g, 85%). MS (ESI) 285 (M+H$^+$).

b) Methyl 2,2-dimethyl-3-(3-benzyloxyphenyl)propionate

A solution of 2,2-dimethyl-3-(3-benzyloxyphenyl)propionic acid (400 mg, 1.4 mmol) in MeOH (20 mL) and conc. $H_2SO_4$ (0.5 mL) was refluxed for 18 h. The reaction was cooled, diluted with $H_2O$, and extracted with $Et_2O$. The extracts were washed with $H_2O$, aqueous $NaHCO_3$ (3×), dried, and concentrated. Purification via silica gel column chromatography eluted with $CH_2Cl_2$:hexane:MeOH (50:50:1) gave the titled compound (208 mg, 50%). MS (ESI) 299 (M+H$^+$).

c) Methyl 2,2-dimethyl-3-(3-hydroxyphenyl)propionate

A solution of methyl 2,2-dimethyl-3-(3-benzyloxyphenyl)propionate (208 mg, 0.7 mmol) in MeOH (10 mL) and 1N HCl (1 mL) was treated with 10% Pd/C (100 mg) and hydrogenated on a Parr shaker with 50 psi $H_2$ pressure for 1 h. The catalyst was filtered. The filtrate was concentrated, diluted with $H_2O$, and extracted with $Et_2O$. The extracts were washed with $H_2O$, dried, and concentrated to yield the titled product (140 mg, 97%). MS (ESI) 209 (M+H$^+$).

d) Methyl N-(2,2-diphenylethyl)-N-(2-chloro-3-trifluoromethylbenzyl)-2,2-dimethyl-3-(3-aminopropoxy)phenylpropionate A solution of methyl 2,2-dimethyl-3-(3-hydroxyphenyl)propionate (135 mg, 0.65 mmol) and N-(2,2-diphenylethyl)-N-(2-chloro-3-trifluoromethylbenzyl)-3-hydroxypropylamine (290 mg, 0.65 mmol) in THF (8 mL) was treated with $Ph_3P$ (170 mg, 0.65 mmol), diisopropylazodicarboxylate (135 mg, 0.65 mmol), and stirred for 16 h. The reaction was diluted with $H_2O$ and extracted with $Et_2O$. The extracts were washed with $H_2O$, dried, and concentrated. Purification via silica gel column chromatography eluted with 30% EtOAc:hexane yielded the titled compound (200 mg, 50%). MS (ESI) 639 (M+H$^+$).

e) N-(2,2-Diphenylethyl)-N-(2-chloro-3-trifluoromethylbenzyl)-2,2-dimethyl-3-(3-aminopropoxy)phenylpropionic acid A solution of methyl N-(2,2-diphenylethyl)-N-(2-chloro-3-trifluoromethylbenzyl)-2,2-dimethyl-3-(3-aminopropoxy)phenylpropionate (195 mg, 0.3 mmol) in MeOH (10 mL), $H_2O$ (1 mL), and 2.5N NaOH (2 mL) was refluxed for 5 h. The reaction was cooled, diluted with $H_2O$, and acidified with 3N HCl to pH=5.1. The mixture was extracted with EtOAc, the extracts were washed with $H_2O$, dried, and concentrated to yield the titled compound (172 mg, 92%). MS (ESI) 625 (M+H$^+$).

EXAMPLE 50

(3-{(R)-[(2,2-Diphenyl-ethyl)-(4-isopropyl-benzyl)-amino]-2-methyl-propoxy}-phenyl)-acetic acid

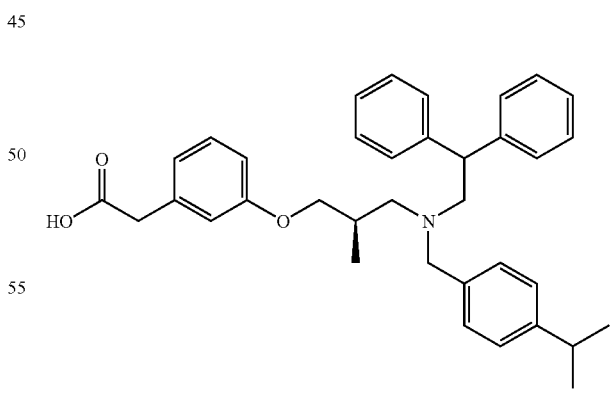

To a solution of {3-[(R)-3-(2,2-diphenyl-ethylamino)-2-methyl-propoxy]-phenyl}-acetic acid methyl ester (100 mg, 240 µmol) in methanol (1 mL) was added acetic acid (10% by volume) followed by 4-isopropyl-benzaldehyde (106 mg, 719 µmol) and sodium cyanoborohydride (44.5 mg, 719 µmol). After the resulting mixture was stirred for 18 h at RT, water was added to the reaction mixture. The solution was made basic by the addition of sodium hydroxide and heated for 30 min. The sample concentrated and was purified by preparative HPLC (TMC CombiPrep PDS, 75×30 mm, 25 mL/min, acetonitrile: H₂O, UV detection at 254 nm) to give the title compound as a solid (49.9 mg, 39%). MS (ESI) 535 (M+H)⁺.

EXAMPLE 51

(3-Chloro-4-{3-[(2-chloro-3-trifluoromethyl-benzyl)-2,2-diphenylethyl-amino]-propoxy}-phenyl)-acetic acid methyl ester

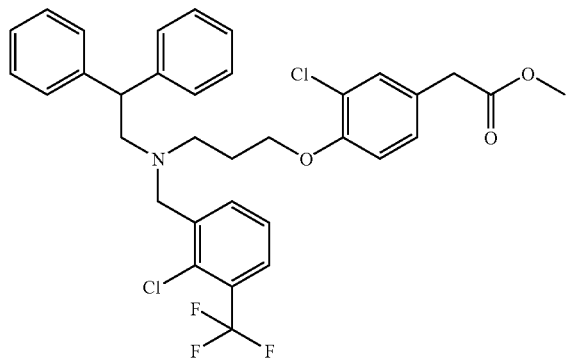

a) (3-Chloro-4-hydroxy-phenyl)-acetic acid methyl ester.

To a solution of (3-chlorohydroxy-phenyl)-acetic acid (0.689 g, 3.7 mmol) and MeOH (30 mL), 1 N HCl (4 mL) was added and the reaction mixture was stirred overnight at 55° C. The mixture was concentrated. H₂O was added and the mixture was extracted with EtOAc. The organic layer was washed with brine, dried over Na₂SO₄, filtered, and concentrated to yield the product as a clear oil (0.435 g, 59%): MS(ES) m/e 201.2 [M+H]⁺.

b) (3-Chloro-4-{3-[(2-chloro-3-trifluoromethyl-benzyl)-2,2-diphenylethyl-amino]-propoxy}-phenyl)-acetic acid methyl ester Following the procedure of Example 43 except (3-chloro-4-hydroxy-phenyl)-acetic acid methyl ester was used instead of 3-hydroxy-benzoic acid methyl ester, the title compound was obtained as a clear oil (64.5 mg, 54%). MS(ES) m/e 630.2 [M+H]⁺.

EXAMPLE 52

(3-Chloro-4-{3-[(2-chloro-3-trifluoromethyl-benzyl)-2,2-diphenylethyl-amino]-propoxy}phenyl)-acetic acid hydrochloride salt

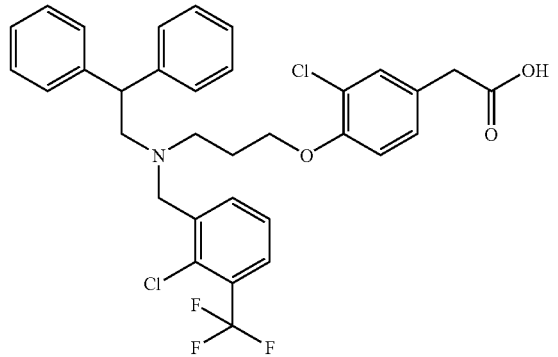

To a solution of (3-chloro-4-{3-[(2-chloro-3-trifluoromethyl-benzyl)-2,2-diphenylethyl-amino]-propoxy}-phenyl)-acetic acid methyl ester (42.8 mg, 0.068 mmol) and THF (2.5 mL) and H₂O (0.8 mL), LiOH (3.4 mg, 0.14 mmol) was added and the reaction mixture was stirred for 12 h. The mixture was concentrated and H₂O was added. The mixture was acidified with 1N HCl, extracted several times with EtOAc, and concentrated. The resulting oil was diluted in Et₂O and acidified with 1.0 M HCl/Et₂O. The mixture was then concentrated to give the product as a white solid (38.9 mg, 88%). MS(ES) m/e 616.2 [M+H]⁺.

EXAMPLE 53

2-(3-{3-[(2-Chloro-3-trifluoromethyl-benzyl)-2,2-diphenylethyl-amino]-propoxy}-phenyl)-2-methyl-propionic acid hydrochloride salt (a) and 2-(3-{3-[(2-Chloro-3-trifluoromethyl-benzyl)-2,2-diphenylethyl-amino]-propoxy}-phenyl)-propionic acid hydrochloride salt (b)

a

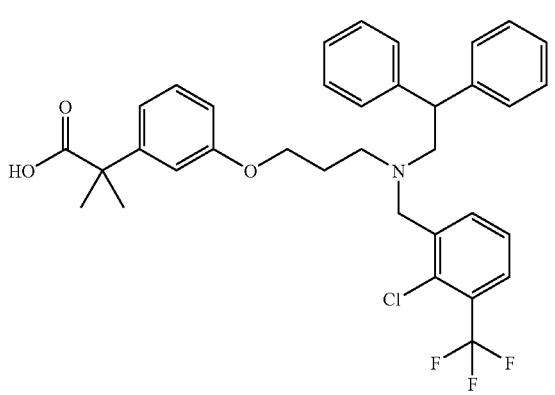

b

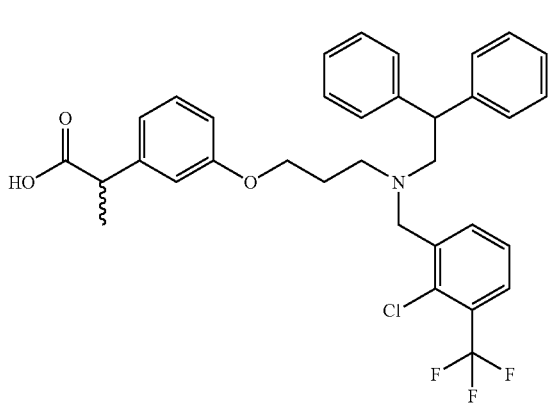

NaH (95%) (102.1 mg, 4.25 mmol) was added to solution of (3-{3-[(2-chloro-3-trifluoromethyl-benzyl)-2,2-diphenyl-ethyl-amino]-propoxy}-phenyl)-acetic acid methyl ester (963.7 mg 1.62 mmol) in anhydrous THF (20 mL). The resulting suspension was stirred vigorously for 15 min at RT, then heated at reflux. Methyl iodide (400 μL, 6.47 mmol) was added and refluxing was continued for 18 h. The mixture was concentrated, water (10 mL) was added to the residue, and 6 N HCl was added to adjust the pH=34. The mixture was extracted with Et₂O (set aside), then EtOAc (set aside). After evaporating each extract, separately, the ethereal extract provided a syrup (454.9 mg) consisting of a mixture of unreacted starting material, a, b, and the methyl ester of a. The ethyl acetate extract provided a syrup (474.3 mg) consisting of a mixture of unreacted staring material, a, and b. The syrup from the ethyl acetate extract was chromatographed on a Chromatotron (Analtech Rotor Silica Gel, GF, $F_{254}$, 2000μ) eluting with n-hexane:ethyl acetate (9:1) to provide a as a syrup, then eluting with n-hexane:ethyl acetate (8:2) to provide b as syrup. Treatment of the samples with Et₂O HCl afforded 45 mg (4.5% yield) of a as an amorphous solid, MS (ESI) 610.4 (M+H)⁺, and 35 mg (3.6% yield) of b as a crystalline solid, mp183-186° C. MS (ESI) 596.4 (M+H)⁺.

The above description fully discloses how to make and use the present invention. However, this invention is not limited to the particular embodiments described hereinabove, but includes all modification thereof within the scope of the appended claims and their equivalents. Those skilled in the art will recognize through routine experimentation that various changes and modifications can be made without departing from the scope of this invention. The various references to journals, patents and other patent applications that are cited herein are incorporated by reference herein as though fully set forth.

What is claimed is:
1. A compound of Formula I:

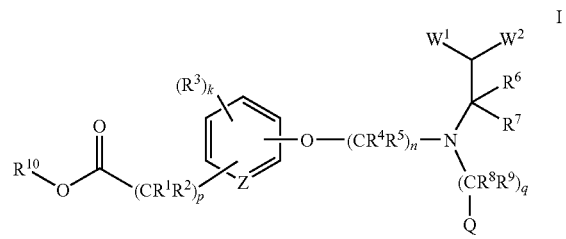

wherein:
Z is CH or $CR^3$; wherein k is 0-4;
p is 0-8;
n is 2-8;
q is 0 or 1;
Q is $C_3$-$C_8$ cycloalkyl or phenyl; wherein said $C_3$-$C_8$ cycloalkyl, or phenyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, —$C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-$OC(O)NR^{12}R^{13}$, —$C_0$-$C_6$ alkyl-$OC(O)OR^{14}$, —$C_0$-$C_6$ alkyl-$NR^{12}C(O)OR^{14}$, —$C_0$-$C_6$ alkyl-$NR^{12}C(O)NR^{12}R^{13}$, and —$C_0$-$C_6$ alkyl-$NR^{12}COR^{14}$, where

---

SEQUENCE LISTING

<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Modified polyhistidine tag

<400> SEQUENCE: 1

Met Lys Lys Gly His His His His His His Gly
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Biotinylated peptide comprising amino acids
      675-699 or SRC-1

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25 said $C_1$-$C_6$ alkyl is optionally unsubstituted or substituted by one or more halo substituents;

$W^1$ and $W^2$ are each independently $C_3$-$C_8$ cycloalkyl or aryl;

each $R^1$ and $R^2$ is independently selected from H, $C_1$-$C_6$ alkyl, —OH, —O—$C_1$-$C_6$ alkyl, —SH, and —S—$C_1$-$C_6$ alkyl;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-$C_3$-$C_7$ cycloalkyl, —$C_0$-$C_6$ alkyl-$CO_2R^{11}$, —$C_0$-$C_6$ alkyl-C(O)$SR^{11}$, —$C_0$-$C_6$ alkyl-$CONR^{12}R^{13}$, —$C_0$-$C_6$ alkyl-$COR^{14}$, —$C_0$-$C_6$ alkyl-$NR^{12}R^{13}$, —$C_0$-$C_6$ alkyl-$SR^{11}$, —$C_0$-$C_6$ alkyl-$OR^{11}$, —$C_0$-$C_6$ alkyl-$SO_3H$, —$C_0$-$C_6$ alkyl-$SO_2NR^{12}R^{13}$, —$C_0$-$C_6$ alkyl-$SO_2R^{11}$, —$C_0$-$C_6$ alkyl-$SOR^{14}$, —$C_0$-$C_6$ alkyl-$OCOR^{14}$, —$C_0$-$C_6$ alkyl-OC(O)$NR^{12}R^{13}$, —$C_0$-$C_6$ alkyl-OC(O)$OR^{14}$, —$C_0$-$C_6$ alkyl-$NR^{12}$C(O)$OR^{14}$, —$C_0$-$C_6$ alkyl-$NR^{12}$C(O)$NR^{12}R^{13}$, and —$C_0$-$C_6$ alkyl-$NR^{12}COR^{14}$, wherein said $C_1$-$C_6$ alkyl is optionally unsubstituted or substituted by one or more halo substituents;

each $R^4$ and $R^5$ is independently H or $C_1$-$C_4$ alkyl;

$R^6$ and $R^7$ are each independently H or $C_1$-$C_4$ alkyl;

$R^8$ and $R^9$ are each independently H or $C_1$-$C_4$ alkyl;

$R^{10}$ is H, $C_1$-$C_8$ alkyl, $C_3$-$C_8$ alkenyl, $C_3$-$C_8$ alkynyl, —$C_0$-$C_6$ alkyl-Ar, or —$C_0$-$C_6$ alkyl-$C_3$-$C_7$ cycloalkyl;

$R^{11}$ is H, $C_1$-$C_6$ alkyl, $C_3$-$C_6$ alkenyl, $C_3$-$C_6$ alkynyl, —$C_0$-$C_6$ alkyl-Ar, or —$C_0$-$C_6$ alkyl-$C_3$-$C_7$ cycloalkyl;

each $R^{12}$ and each $R^{13}$ are independently selected from H, $C_1$-$C_6$ alkyl, $C_3$-$C_6$ alkenyl, $C_3$-$C_6$ alkynyl, —$C_0$-$C_6$ alkyl-Ar, and —$C_0$-$C_6$ alkyl-$C_3$-$C_7$ cycloalkyl; and $R^{14}$ is $C_1$-$C_6$ alkyl, $C_3$-$C_6$ alkenyl, $C_3$-$C_6$ alkynyl, —$C_0$-$C_6$ alkyl-Ar, or —$C_0$-$C_6$ alkyl-$C_3$-$C_7$ cycloalkyl;

provided that $R^{10}$ is not H or methyl when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;

or a pharmaceutically acceptable salt thereof.

2. The compound according to claim 1, wherein p is 0 or 1.

3. The compound according to claim 1, wherein $R^1$ and $R^2$ are each H, or one of $R^1$ or $R^2$ is H and the other of $R^1$ or $R^2$ is $C_1$-$C_4$ alkyl or both $R^1$ and $R^2$ are $C_1$-$C_3$ alkyl.

4. The compound according to claim 1, wherein $R^1$ and $R^2$ are each H, or one of $R^1$ or $R^2$ is H and the other of $R^1$ or $R^2$ is methyl, ethyl, propyl, butyl, or sec-butyl, or $R^1$ and $R^2$ are both methyl or ethyl.

5. The compound according to claim 1, wherein $R^{10}$ is H or $C_1$-$C_4$ alkyl.

6. The compound according to claim 1, wherein Z is CH.

7. The compound according to claim 1, wherein k is 0 or 1.

8. The compound according to claim 1, wherein $R^3$ is selected from halo, $C_1$-$C_4$ alkyl and $C_1$-$C_4$ alkoxy.

9. The compound according to claim 1, wherein n is 2-4.

10. The compound according to claim 1, wherein n is 3.

11. The compound according to claim 1, wherein q is 1.

12. The compound according to claim 1, wherein $R^6$, $R^7$, $R^8$ and $R^9$ are each H.

13. The compound according to claim 1, wherein Q is a substituted phenyl group having one, two, or three substituents independently selected from halo, $C_1$-$C_4$ alkoxy and $C_1$-$C_4$ alkyl.

14. The compound according to claim 1, wherein Q is a substituted phenyl group having two substituents independently selected from —F, —Cl, —$CF_3$, —$OCH_3$, and —CH($CH_3$)$_2$.

15. The compound according to claim 1, wherein Q is a 2-chloro-3-(trifluoromethyl)phenyl group.

16. The compound according to claim 1, wherein $W^1$ and $W^2$ are each aryl or one of $W^1$ or $W^2$ is aryl and the other of $W^1$ or $W^2$ is cyclopentyl.

17. The compound according to claim 1, wherein $W^1$ and $W^2$ are each independently selected from unsubstituted cyclopentyl, unsubstituted phenyl and mono-substituted phenyl, where the phenyl is substituted by halo.

18. The compound according to claim 1, wherein $W^1$ and $W^2$ are both unsubstituted phenyl, or one of $W^1$ or $W^2$ is unsubstituted phenyl and the other of $W^1$ or $W^2$ is cyclopentyl, or $W^1$ and $W^2$ are both fluoro-substituted phenyl or one of $W^1$ or $W^2$ is unsubstituted phenyl and the other of $W^1$ or $W^2$ is chloro-substituted phenyl.

19. A compound of Formula II:

wherein:

Z is CH;

Q is phenyl; wherein said phenyl is optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{11}$, —$C_0$-$C_6$ alkyl-C(O)$SR^{11}$, —$C_0$-$C_4$ alkyl-$CONR^{12}R^{13}$, —$C_0$-$C_4$ alkyl-$COR^{14}$, —$C_0$-$C_4$ alkyl-$NR^{12}R^{13}$, —$C_0$-$C_4$ alkyl-$SR^{11}$, —$C_0$-$C_4$ alkyl-$OR^{11}$, —$C_0$-$C_4$ alkyl-$SO_3H$, —$C_0$-$C_4$ alkyl-$SO_2NR^{12}R^{13}$, —$C_0$-$C_4$ alkyl-$SO_2R^{11}$, —$C_0$-$C_4$ alkyl-$SOR^{14}$, —$C_0$-$C_4$ alkyl-$OCOR^{14}$, —$C_0$-$C_4$ alkyl-OC(O)$NR^{12}R^{13}$, —$C_0$-$C_4$ alkyl-OC(O)$OR^{14}$, —$C_0$-$C_4$ alkyl-$NR^{12}$C(O)$OR^{14}$, —$C_0$-$C_4$ alkyl-$NR^{12}$C(O)$NR^{12}R^{13}$, and —$C_0$-$C_4$ alkyl-$NR^{12}COR^{14}$, where said $C_1$-$C_6$ alkyl is optionally unsubstituted or substituted by one or more halo substituents, p is 0-4;

k is 0, 1 or 2;

n is 2-4;

q is 0 or 1;

$W^1$ and $W^2$ are each independently $C_3$-$C_6$ cycloalkyl or aryl;

each $R^1$ and $R^2$ is independently selected from H, $C_1$-$C_4$ alkyl, —OH, —O—$C_1$-$C_4$ alkyl, —SH, and —S—$C_1$-$C_4$ alkyl;

each $R^3$ is the same or different and is independently selected from halo, cyano, $C_1$-$C_6$ alkyl, —$C_0$-$C_4$ alkyl-$NR^{12}R^{13}$, —$C_0$-$C_4$ alkyl-$OR^{11}$, —$C_0$-$C_4$ alkyl-$SO_2NR^{12}R^{13}$, and —$C_0$-$C_4$ alkyl-$CO_2H$, wherein said $C_1$-$C_6$ alkyl is optionally unsubstituted or substituted by one or more halo substituents;

each $R^4$ and $R^5$ is independently H or $C_1$-$C_4$ alkyl;

$R^6$ and $R^7$ are each independently H or $C_1$-$C_4$ alkyl;

$R^8$ and $R^9$ are each independently H or $C_1$-$C_4$ alkyl;

$R^{10}$ is H, $C_1$-$C_6$ alkyl, —$C_0$-$C_4$ alkyl-Ar, or —$C_0$-$C_4$ alkyl-$C_3$-$C_6$ cycloalkyl;

$R^{11}$ is H, $C_1$-$C_6$ alkyl, —$C_0$-$C_4$ alkyl-Ar, or —$C_0$-$C_4$ alkyl-$C_3$-$C_7$ cycloalkyl;

each $R^{12}$ and each $R^{13}$ are independently selected from H, $C_1$-$C_6$ alkyl, —$C_0$-$C_4$ alkyl-Ar, and —$C_0$-$C_4$ alkyl-$C_3$-$C_7$ cycloalkyl; and $R^{14}$ is $C_1$-$C_6$ alkyl, —$C_0$-$C_4$ alkyl-Ar, or —$C_0$-$C_4$ alkyl-$C_3$-$C_7$ cycloalkyl;

provided that $R^{10}$ is not H or methyl when p is 1 and $R^1$ and $R^2$ are each H, k is 0, n is 3 and each $R^4$ and $R^5$ are H, q is 1 and $R^8$ and $R^9$ are each H, Q is unsubstituted phenyl or 4-methoxyphenyl or 2-chloro-3-trifluoromethyl-phenyl, $R^6$ and $R^7$ are each H, $W^1$ is unsubstituted phenyl and $W^2$ is unsubstituted phenyl or unsubstituted cyclohexyl;

or a pharmaceutically acceptable salt thereof.

20. The compound according to claim 1, wherein $R^4$, $R^5$, $R^6$, $R^7$, $R^8$ and $R^9$ are each H; at least one of $R^1$ or $R^2$ is methyl, ethyl, propyl butyl or sec-butyl or both of $R^1$ and $R^2$ are methyl or ethyl; $R^{10}$ is H or methyl; Q is 2-chloro-3-(trifluoromethyl)phenyl; $W^1$ and $W^2$ are both unsubstituted phenyl, or one of $W^1$ or $W^2$ is unsubstituted phenyl and the other of $W^1$ or $W^2$ is cyclopentyl, or $W^1$ and $W^2$ are both fluoro-substituted phenyl or one of $W^1$ or $W^2$ is unsubstituted phenyl and the other of $W^1$ or $W^2$ is chloro-substituted phenyl; Z is CH; p is 0, 1 or 2; n is 3; q is 1; k is 0 or 1 and $R^3$ is Cl, Br or methyl; or a pharmaceutically acceptable salt thereof.

21. The compound according to claim 1, wherein $R^6$, $R^7$, $R^8$ and $R^9$ are each H; $R^1$ and $R^2$ are each independently H or methyl; at least one $R^4$ $R^5$ is methyl; $R^{10}$ is H or methyl; Q is a substituted phenyl group containing one, two, or three substituents selected from —F, —Cl, —$CF_3$, —$OCH_3$, and —$CH(CH_3)_2$; $W^1$ and $W^2$ are unsubstituted phenyl; Z is CH; p is 1; n is 3; q is 1; and k is 0; or a pharmaceutically acceptable salt thereof.

22. A pharmaceutical composition comprising a compound according to claim 1 and a pharmaceutically acceptable carrier or diluent.

23. A compound according to claim 1 wherein at least one of $R^4$, $R^5$, $R^6$, $R^7$, $R^8$ or $R^9$ is defined as follows:
wherein at least one $R^4$ or $R^5$ is $C_1$-$C_4$ alkyl; or
at least one of $R^6$ of $R^7$ is $C_1$-$C_4$ alkyl; or
both of $R^8$ or $R^9$ are independently $C_1$-$C_4$ alkyl.

24. A compound according to claim 1 wherein at least one $R^4$ or $R^5$ is methyl.

25. A compound according to claim 1 wherein:
any one of $R^4$ or $R^5$ is not H or
any one of $R^6$ or $R^7$ is not H or
$R^8$ and $R^9$ are each $C_1$-$C_4$ alkyl when
Z is CH or $CR^3$ and k is 0-4;
p is 0-8;
n is 2-8;
q is 0 or 1;
Q is optionally unsubstituted or substituted $C_3$-$C_8$ cycloalkyl or phenyl;
$W^1$ and $W^2$ are each independently optionally unsubstituted or substituted $C_3$-$C_8$ cycloalkyl or aryl;
each $R^1$ and $R^2$ is independently selected from H, $C_1$-$C_6$ alkyl, —OH, —O—$C_1$-$C_6$ alkyl, —SH, and —S—$C_1$-$C_6$ alkyl;
each $R^3$ is the same or different and is independently selected from halo, cyano, nitro, —$CONR^{12}R^{13}$, —$COR^{14}$, —$SR^{11}$, —$SO_2R^{11}$, —$SOR^{14}$, —$OCOR^{14}$ and optionally unsubstituted or substituted $C_1$-$C_6$ alkyl, $C_3$-$C_6$ alkenyl, —$C_0$-$C_6$ alkyl-$CO_2R^{11}$, or —$C_0$-$C_6$ alkyl-$NR^{12}R^{13}$.

26. A compound according to claim 1, selected from:
(R)-2-(3-{3-[[2-Chloro-3-(trifluoromethyl)benzyl](2,2-diphenylethyl)amino]-2-methyl-propoxy}-phenyl)acetic acid methyl ester,
(R)-2-(3-{3-[[2-Chloro-3-(trifluoromethyl)benzyl](2,2-diphenylethyl)amino]-2-methyl-propoxy}-phenyl)acetic acid hydrochloride salt,
(S)-2-(3-{3-[[2-Chloro-3-(trifluoromethyl)benzyl](2,2-diphenylethyl)amino]-2-methyl-propoxy}-phenyl)acetic acid hydrochloride salt,
(R)-2-(3-{3-[[2-Chloro-3-(trifluoromethyl)benzyl](2,2-diphenylethyl)amino]-1-methyl-propoxy}-phenyl)acetic acid methyl ester,
(R)-2-(3-{3-[[2-Chloro-3-(trifluoromethyl)benzyl](2,2-diphenylethyl)amino]-1-methyl-propoxy}-phenyl)acetic acid hydrochloride salt,
(S)-2-(3-{3-[[2-Chloro-3-(trifluoromethyl)benzyl](2,2-diphenylethyl)amino]-1-methyl-propoxy}-phenyl)acetic acid hydrochloride salt,
(R)-2-(3-{3-[[2-Chloro-3-(trifluoromethyl)benzyl](2,2-diphenylethyl)amino]-3-methyl-propoxy}-phenyl)acetic acid hydrochloride salt,
(S)-2-(3-{3-[[2-Chloro-3-(trifluoromethyl)benzyl](2,2-diphenylethyl)amino]-3-methyl-propoxy}-phenyl)acetic acid hydrochloride salt, and
3-{3-[[2-Chloro-3-(trifluoromethyl)benzyl](2,2-diphenylethyl)amino]-propoxy}-4-methyl-benzoic acid hydrochloride salt.

27. A compound according to claim 1, selected from:
(R)-2-(3-{3-[[2-fluoro-3-(trifluoromethyl)benzyl](2,2-diphenylethyl)amino]-2-methyl-propoxy}-phenyl)acetic acid;
(R)-2-(3-{3-[[3-(trifluoromethyl)-4-fluoro-benzyl](2,2-diphenylethyl)amino]-2-methyl-propoxy}-phenyl)acetic acid;
(R)-2-(3-{3-[[2,4-dimethoxy-benzyl](2,2-diphenylethyl)amino]-2-methyl-propoxy}-phenyl)acetic acid;
(R)-2-(3-{3-[[4-methoxy-benzyl](2,2-diphenylethyl)amino]-2-methyl-propoxy}-phenyl)acetic acid;
(R)-2-(3-{3-[[2-fluoro-4-methoxy-benzyl](2,2-diphenylethyl)amino]-2-methyl-propoxy}-phenyl)acetic acid;
(R)-2-(3-{3-[[3-fluoro-4-methoxy-benzyl](2,2-diphenylethyl)amino]-2-methyl-propoxy}-phenyl)acetic acid;
(R)-2-(3-{3-[[2,4-dimethoxybenzyl](2,2-diphenylethyl)amino]-1-methyl-propoxy}-phenyl)acetic acid;
(R)-2-(3-{3-[[4-methoxybenzyl](2,2-diphenylethyl)amino]-1-methyl-propoxy}-phenyl)acetic acid;
(R)-2-(3-{3-[[2-fluoro-4-methoxybenzyl](2,2-diphenylethyl)amino]-1-methyl-propoxy}-phenyl)acetic acid;
(R)-2-(3-{3-[[3-trifluoromethylbenzyl](2,2-diphenylethyl)amino]-1-methyl-propoxy}-phenyl)acetic acid;
(R)-2-(3-{3-[[2-fluoro-3-(trifluoromethyl)benzyl](2,2-diphenylethyl)amino]-1-methyl-propoxy}-phenyl)acetic acid;
(R)-2-(3-{3-[[3-(trifluoromethyl)-4-fluoro-benzyl](2,2-diphenylethyl)amino]-1-methyl-propoxy}-phenyl)acetic acid;
(R)-2-(3-{3-[[3-fluoro-4-methoxybenzyl](2,2-diphenylethyl)amino]-1-methyl-propoxy}-phenyl)acetic acid;
(R)-2-(3-{3-[[2-chlorobenzyl](2,2-diphenylethyl)amino]-3-methyl-propoxy}-phenyl)acetic acid;
(R)-2-(3-{3-[[3-trifluoromethylbenzyl](2,2-diphenylethyl)amino]-3-methyl-propoxy}-phenyl)acetic acid;

(R)-2-(3-{3-[[2-fluoro-(3-trifluoromethyl)benzyl](2,2-diphenylethyl)amino]-3-methyl-propoxy}-phenyl)acetic acid;

(R)-2-(3-{3-[[3-trifluoromethyl-4-fluoro-benzyl](2,2-diphenylethyl)amino]-3-methyl-propoxy}-phenyl)acetic acid;

(R)-2-(3-{3-[[2,4-dimethoxybenzyl](2,2-diphenylethyl)amino]-3-methyl-propoxy}-phenyl)acetic acid;

(R)-2-(3-{3-[[4-methoxybenzyl](2,2-diphenylethyl)amino]-3-methyl-propoxy}-phenyl)acetic acid;

(R)-2-(3-{3-[[2-fluoro-4-methoxybenzyl](2,2-diphenylethyl)amino]-3-methyl-propoxy}-phenyl)acetic acid;

(R)-2-(3-{3-[[2-chloro-3,4-dimethoxybenzyl](2,2-diphenylethyl)amino]-3-methyl-propoxy}-phenyl)acetic acid;

(R)-2-(3-{3-[[3-fluoro-4-methoxybenzyl](2,2-diphenylethyl)amino]-3-methyl-propoxy}-phenyl)acetic acid;

(3-{(R)-[(2,2-diphenyl-ethyl)-(4-isopropyl-benzyl)-amino]-methyl-propoxy}-phenyl)-acetic acid;

(3-{3-[[2,2-(bis-(4-fluoro-phenyl)-ethyl]-(2-chloro-3-(trifluoromethyl)-benzyl-amino]-propoxy}-phenyl)-acetic acid;

(3-{3-[[2,2-(bis-(3-fluoro-phenyl)-ethyl]-(2-chloro-3-(trifluoromethyl)-benzyl)-amino]-propoxy}-phenyl)-acetic acid;

rac-(3-{3-[[2-phenyl-2-(o-chloro-phenyl)-ethyl]-(2-chloro-3-(trifluoromethyl)-benzyl)-amino]-propoxy}-phenyl)-acetic acid;

2-(3-{3-[(2-chloro-3-trifluoromethyl-benzyl)-2,2-diphenylethyl-amino]-propoxy}-phenyl)-butyric acid;

2-(3-{3-[(2-chloro-3-trifluoromethyl-benzyl)-2,2-diphenylethyl-amino]-propoxy}-phenyl)-pentanoic acid;

2-(3-{3-[(2-chloro-3-trifluoromethyl-benzyl)-2,2-diphenylethyl-amino]-propoxy}-phenyl)-hexanoic acid;

2-(3-{3-[(2-chloro-3-trifluoromethyl-benzyl)-2,2-diphenylethyl-amino]-propoxy}-phenyl)-4-methyl-pentanoic acid;

2-(3-{3-[(2-chloro-3-trifluoromethyl-benzyl)-2,2-diphenylethyl-amino]-propoxy}-phenyl)-2-ethyl-butyric acid methyl ester;

2-(3-{3-[(2-chloro-3-trifluoromethyl-benzyl)-2,2-diphenylethyl-amino]-propoxy}-phenyl)-2-ethyl-butyric acid;

2-(3-{(R)-3-[(2-chloro-3-trifluoromethyl-benzyl)-2,2-diphenylethyl-amino]-butoxy}-phenyl)-2-methyl-propionic acid;

N-(2-phenyl-2-cyclopentylethyl)-N-(2-chloro-3-trifluoromethylbenzyl)-3-(3-carboxymethylenephenoxy)propylamine;

N-(2,2-diphenylethyl)-N-(2-chloro-3-trifluoromethylbenzyl)-2,2-dimethyl-3-(3-aminopropoxy)phenylpropionic acid; and 2-(3-{3-[(2-chloro-3-trifluoromethyl-benzyl)-2,2-diphenylethyl-amino]-propoxy}-phenyl)-2-methyl-propionic acid;

or a pharmaceutically acceptable salt thereof.

* * * * *